US012653813B2

(12) United States Patent
Zhou et al.

(10) Patent No.: US 12,653,813 B2
(45) Date of Patent: Jun. 16, 2026

(54) THIADIAZOLONE DERIVATIVES, COMPOSITIONS AND USES THEREOF

(71) Applicant: Danatlas Pharmaceuticals Co., Ltd., Beijing (CN)

(72) Inventors: Wenlai Zhou, Beijing (CN); Jincong Zhuo, Beijing (CN); Yao Zhang, Beijing (CN)

(73) Assignee: DANATLAS PHARMACEUTICALS CO., LTD., Beijing (CN)

( * ) Notice: Subject to any disclaimer, the term of this patent is extended or adjusted under 35 U.S.C. 154(b) by 0 days.

(21) Appl. No.: 19/356,058

(22) Filed: Oct. 11, 2025

(65) Prior Publication Data

US 2026/0034113 A1 Feb. 5, 2026

Related U.S. Application Data

(63) Continuation of application No. PCT/CN2024/087388, filed on Apr. 12, 2024.

(30) Foreign Application Priority Data

Apr. 13, 2023 (WO) ............... PCT/CN2023/087991
Jun. 20, 2023 (WO) ............... PCT/CN2023/101401
Sep. 21, 2023 (WO) ............... PCT/CN2023/120470

(51) Int. Cl.
| | |
|---|---|
| *A61K 31/444* | (2006.01) |
| *A61K 31/433* | (2006.01) |
| *A61K 31/4439* | (2006.01) |
| *C07D 417/12* | (2006.01) |
| *C07D 417/14* | (2006.01) |

(52) U.S. Cl.
CPC .......... *A61K 31/444* (2013.01); *A61K 31/433* (2013.01); *A61K 31/4439* (2013.01); *C07D 417/12* (2013.01); *C07D 417/14* (2013.01)

(58) Field of Classification Search
CPC .................................... A61K 31/444
See application file for complete search history.

(56) References Cited

U.S. PATENT DOCUMENTS

2017/0267662 A1 9/2017 Inoue et al.

FOREIGN PATENT DOCUMENTS

| WO | 2016098005 A1 | 6/2016 |
|---|---|---|
| WO | WO2016098005 * | 6/2016 |
| WO | 2020243459 A1 | 12/2020 |
| WO | 2022118210 A1 | 6/2022 |
| WO | 2022259204 A1 | 12/2022 |

OTHER PUBLICATIONS

International Search Report and Written Opinion of ISA received in the counterpart international application PCT/CN2024/087388 mailed on Aug. 3, 2024.
Safiye Sag Erdem et al., Investigation on the aromaticity of 1,3,4-thiadiazole-2-thione and its oxygen analogs including their tautomeric forms, Journal of Molecular Structure: THEOCHEM 726 (2005) 233-243.

* cited by examiner

*Primary Examiner* — Rei Tsang Shiao
(74) *Attorney, Agent, or Firm* — Kilpatrick Townsend & Stockton LLP

(57) ABSTRACT

The disclosure relates to thiadiazolone derivatives as shown in Formula (I), to pharmaceutical compositions comprising them, to a process for their preparation, and their use as therapeutic agents.

(I)

30 Claims, No Drawings

THIADIAZOLONE DERIVATIVES, COMPOSITIONS AND USES THEREOF

CROSS REFERENCES TO RELATED APPLICATIONS

The present application is a continuation application of Internation Patent Application No. PCT/CN2024/087388, filed on Apr. 12, 2024, which claims the benefit of the priority of International Application No. PCT/CN2023/087991, filed Apr. 13, 2023, International Application No. PCT/CN2023/101401, filed Jun. 20, 2023, International Application No. PCT/CN2023/120470, filed Sep. 21, 2023, each of which is hereby incorporated in its entirety.

TECHNICAL FIELD

The present disclosure relates to thiadiazolone derivatives as PolQ inhibitors and pharmaceutical compositions thereof. The present disclosure also relates to methods for preparing the thiadiazolone derivatives and their uses in the treatment of a PolQ-mediated disease, e.g., cancers containing DNA repair defects.

BACKGROUND

DNA damage repair processes are critical for genome maintenance and cell viability. Double strand breaks (DSBs) can be repaired by one of three main pathways: homologous recombination (HR), non-homologous end-joining (NHEJ) and alternative NHEJ (alt-NHEJ). An alternative end joining (alt-NHEJ), also known as microhomology-mediated end-joining (MMEJ) pathway, is commonly considered as a "backup" DSB repair pathway when NHEJ or HR are compromised (Truong et al., PNAS 2013, 110 (19), 7720-7725).

An aberrant DNA damage response (DDR) often can sensitize cancer cells to specific types of DNA damage, thus, defective DDR can be developed into targeted cancer therapies. Targeting DNA repair deficiencies has become a proven and effective strategy in cancer treatment. For example, the success of poly (ADP-ribose) polymerase (PARP) inhibitors in treating BRCA-deficient breast, ovarian, prostate and pancreatic cancers (Audeh M. W., et al., Lancet (2010); 376 (9737): 245-51).

Numerous genetic, cell biological and biochemical studies have demonstrated that DNA polymerase theta (PolQ, UniProtKB-O75417 (DPOLQ_HUMAN) is a key protein involved in MMEJ (Kent et al., Nature Structural & Molecular Biology (2015), 22(3), 230-237, Mateos-Gomez et al., Nature (2015), 518(7538), 254-257).

PolQ is distinct among human DNA polymerases, comprising an N-terminal helicase domain (SF2 HEL308-type) and a C-terminal low-fidelity DNA polymerase domain (A-type) (Wood & Doublie DNA Repair (2016), 44, 22-32). In homologous recombination deficient (HRD) cells, PolQ can carry out error-prone DNA synthesis at DNA damage sites through alt-NHEJ pathway. It has been shown that the helicase domain of PolQ mediates the removal of RPA protein from ssDNA ends and stimulates annealing. This anti-recombinase activity of PolQ promotes the alt-NHEJ pathway. In addition, the helicase domain of PolQ contributes to microhomology-mediated strand annealing (Chan S H et al., PLoS Genet. (2010); 6: e1001005; and Kawamura K et al., Int. J. Cancer (2004); 109: 9-16). PolQ can promote end joining in alt-NHEJ pathway by employing this annealing activity when ssDNA overhangs contain >2 bp of microhomology (Kent T., et al., Elife (2016); 5: e13740), and Kent T., et al., Nat. Struct. Mol. Biol. (2015); 22: 230-237). This reannealing activity is obtained through coupled actions of Rad51 interaction followed by ATPase-mediated displacement of Rad51 from DSB damage sites. Once annealed, the polymerase domain extends the ssDNA ends and fills the remaining gaps.

The expression of PolQ is low in normal cells but significantly over-expressed in subsets of HRD ovarian, uterine and breast cancers with associated poor prognosis (Higgins et al., Oncotarget (2010), 1, 175-184, Lemee et al., PNAS (2010), 107(30), 13390-13395, Ceccaldi et al., (2015), supra). Secondly, recent studies suggest that cancer cells with deficiency in HR, NHEJ or ATM are highly dependent on PolQ expression (Ceccaldi R., et al., Nature (2015); 518: 258-62, Mateos-Gomez P A et al., Nature (2015); 518: 254-57, and Wyatt D. W., et al., Mol. Cell (2016); 63: 662-73). Finally, PolQ inhibition could conceivably prevent the MMEJ-dependent functional reversion of BRCA1- or BRCA2-mutations that underlies the emergence of cisplatin and PARPi resistance in tumors (Zatreanu D., et al., Nature Communications (2021) 12: 3636). Therefore, PolQ is an attractive target for novel synthetic lethal therapy in cancers containing DNA repair defects. And the novel compounds of the present disclosure have pharmacological properties.

SUMMARY

The present disclosure relates to, inter alia, a compound of Formula (I), (I)

or a pharmaceutically acceptable salt, solvate, tautomer, stereoisomer, atropisomer, isotopic variant, prodrug or deuterated compound thereof, wherein the variables are as defined below.

In another aspect, provided herein is a pharmaceutical composition comprising the compound of Formula (I), or a pharmaceutically acceptable salt, solvate, tautomer, stereoisomer, atropisomer, isotopic variant, prodrug or deuterated compound thereof and at least one pharmaceutically acceptable excipient.

In another aspect, provided herein is a method of inhibiting PolQ comprising:

contacting PolQ with the compound of Formula (I), or a pharmaceutically acceptable salt, solvate, tautomer, stereoisomer, atropisomer, isotopic variant, prodrug or deuterated compound thereof.

In another aspect, provided herein is a method of treating cancers comprising administering to a patient a therapeutically effective amount of the compound of formula (I), or a pharmaceutically acceptable salt, solvate, tautomer, stereoisomer, atropisomer, isotopic variant, prodrug or deuterated compound thereof.

The details of one or more embodiments are set forth in the description below. Other features, objects, and advantages will be apparent from the description and from the claims.

DETAILED DESCRIPTION

The present disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

Before the present invention is further described, it is to be understood that the invention is not limited to the particular embodiments set forth herein, and it is also to be understood that the terminology used herein is for the purpose of describing particular embodiments only, and is not intended to be limiting.

The present disclosure relates to, inter alia, a compound of Formula (I), (I)

or a pharmaceutically acceptable salt, solvate, tautomer, stereoisomer, atropisomer, isotopic variant, prodrug or deuterated compound thereof, wherein:

ring A is $C_3$-$C_{14}$ cycloalkyl, 4-14 membered heterocycloalkylene, $C_6$-$C_{14}$ arylene or 5-14 membered heteroarylene;

ring B is partially unsaturated 5-14 membered heterocycloalkylene, $C_6$-$C_{14}$ arylene or 5-14 membered heteroarylene;

m is 0, 1, 2, 3, 4 or 5;

n is 0, 1, 2, 3, 4 or 5;

each $R^1$ is independently H, D, halogen, —CN, —NO$_2$, N$_3$, —SF$_5$, oxo, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl, —NR$^C$R$^D$, —OR$^A$, —SR$^A$, —NR$^C$OR$^A$, —C(O)R$^B$, —C(O)NR$^C$R$^D$, —C(O)OR$^A$, —OC(O)R$^B$, —NR$^C$C (O)R$^B$, —S(O)R$^B$, —S(O)$_2$R$^B$, —S(O)NR$^C$R$^D$, —NRCS(O)$_2$R$^D$, —S(O)$_2$NR$^C$R$^D$, —NR$^C$S(O)$_2$ NR$^C$R$^D$, —NR$^C$S(O)(=NR$^B$)R$^B$, —SiR$^G$R$^H$R$^I$, —B(OR$^C$)(OR$^D$), —P(O)R$^E$R$^F$, —P(O)OR$^E$OR$^F$, —OP(O)OR$^E$OR$^F$; wherein, the $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl is optionally substituted with 1, 2, 3, 4 or 5 substituent(s) independently selected from $R^{1A}$; or two $R^1$ together with the atom(s) to which they are attached form oxo, $C_3$-$C_7$ cycloalkyl or 4-7 membered heterocycloalkyl; wherein, the $C_3$-$C_7$ cycloalkyl or 4-7 membered heterocycloalkyl is optionally substituted with 1, 2, 3, 4 or 5 substituent(s) independently selected from $R^{1A}$;

each $R^{1A}$ is independently D, halogen, —CN, —NO$_2$, —N$_3$, oxo, —OR$^a$, —NR$^C$R$^d$, —C(O)NR$^C$R$^d$, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl, or 5-6 membered heteroaryl; wherein, the $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl, or 5-6 membered heteroaryl is optionally substituted with D, halogen, —CN, —OH, —NH$_2$, oxo, —NR$^C$R$^d$, —OR$^a$, —SR$^a$, $C_1$-$C_6$ alkyl, $C_1$-$C_6$ haloalkyl;

each $R^2$ is independently H, D, —CN, —NO$_2$, —N$_3$, oxo, —SF$_5$, halogen, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, —NR$^C$R$^D$, —OR$^A$, —SR$^A$, —NR$^C$OR$^A$, —C(O)R$^B$, —C(O)NR$^C$R$^D$, —C(O)OR$^A$, —OC(O)R$^B$, —NR$^C$C (O)R$^B$, —S(O)R$^B$, —S(O)$_2$R$^B$, —S(O)NR$^C$R$^D$, —NRCS(O)$_2$R$^D$, —S(O)$_2$NR$^C$R$^D$, —NR$^C$S(O)$_2$ NR$^C$R$^D$, —NRCS(O)(=NR$^B$)R$^B$, —SiR$^G$R$^H$R$^I$, —B(OR$^C$)(OR$^D$), —P(O)R$^E$R$^F$, —P(O)OR$^E$OR$^F$, —OP(O)OR$^E$OR$^F$; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl is optionally substituted with 1, 2, 3, 4 or 5 substituent(s) independently selected from $R^{2A}$; or two $R^2$ together with the atom(s) to which they are attached form oxo, $C_3$-$C_7$ cycloalkyl, 4-7 membered heterocycloalkyl; wherein, the $C_3$-$C_7$ cycloalkyl, 4-7 membered heterocycloalkyl is optionally substituted by 1, 2, 3 or 4 substituents independently selected from $R^{2A}$;

each $R^{2A}$ is independently D, halogen, —CN, —OH, —NH$_2$, —NO$_2$, —SF$_5$, oxo, $C_1$-$C_4$ alkyl, $C_2$-$C_4$ alkenyl, $C_2$-$C_4$ alkynyl, $C_3$-$C_6$ cycloalkyl, 4-6 membered heterocycloalkyl, phenyl, 5-6 membered heteroaryl, —NR$^C$R$^d$, —OR$^a$, —SR$^a$, —C(O)R$^b$, —C(O)NR$^C$R$^d$, —C(O)OR$^a$, —OC(O)R$^b$, —OC(O)NR$^C$R$^d$, —NR$^C$C (O)R$^b$, —NR$^C$C(O)NR$^C$R$^d$, —NR$^C$C(O)OR$^a$, —S(O) (=NR$^b$)R$^b$, —S(O)R$^b$, —S(O)NR$^C$R$^d$, —S(O)$_2$R$^b$, —NR$^C$S(O)$_2$R$^d$, —S(O)$_2$NR$^C$R$^d$, —NR$^C$S(O)$_2$NR$^C$R$^d$, or —NR$^C$S(O)(=NR$^b$)R$^b$; wherein, the $C_1$-$C_4$ alkyl, $C_2$-$C_4$ alkenyl, $C_2$-$C_4$ alkynyl, $C_3$-$C_6$ cycloalkyl, 4-6 membered heterocycloalkyl, phenyl, 5-6 membered heteroaryl is optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl;

$R^3$ is $C_1$-$C_{10}$ alkyl, $C_2$-$C_{10}$ alkenyl, $C_2$-$C_{10}$ alkynyl, $C_3$-$C_{14}$ cycloalkyl, 4-14 membered heterocycloalkyl, $C_6$-$C_{14}$ aryl, 5-14 membered heteroaryl; wherein, the $C_1$-$C_{10}$ alkyl, $C_2$-$C_{10}$ alkenyl, $C_2$-$C_{10}$ alkynyl, $C_3$-$C_{14}$ cycloalkyl, 4-14 membered heterocycloalkyl, $C_6$-$C_{14}$ aryl, 5-14 membered heteroaryl is optionally substituted by 1, 2, 3, 4 or 5 substituent(s) independently selected from $R^4$;

each $R^4$ is independently H, D, halo, —CN, —NO$_2$, —N$_3$, oxo, —NR$^C$R$^D$, —OR$^A$, —SR$^A$, —NR$^C$OR$^A$, —C(O) R$^B$, —C(O)NR$^C$R$^D$, —C(O)OR$^A$, —OC(O)R$^B$, —OC (O)NR$^C$R$^D$, —NR$^C$C(O)R$^B$, —NR$^C$C(O)NR$^C$R$^D$, —NR$^C$C(O)OR$^A$, —S(O)R$^B$, —S(O)$_2$R$^B$, —S(O) NR$^C$R$^D$, —NRCS(O)$_2$R$^D$, —S(O)$_2$NR$^C$R$^D$, —NRCS (O)$_2$NR$^C$R$^D$, —NRCS(O)(=NR$^B$)R$^B$, —SiR$^G$R$^H$R$^I$, —B(OR$^C$)(OR$^D$), —P(O)R$^E$R$^F$, $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, or 4-10 membered heterocycloalkyl; wherein, the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, or 4-10 membered heterocycloalkyl is optionally substituted with 1, 2, 3, 4, or 5 substituents independently selected from $R^5$; or two $R^4$ together with the atom(s) to which they are attached form oxo, $C_3$-$C_6$ cycloalkyl, 4-6 membered heterocycloalkyl; each ring is optionally substituted with 1, 2, 3, 4 or 5 substituent(s) independently selected from $R^5$;

each $R^5$ is independently D, —CN, halo, —$NO_2$, —$N_3$, —$SF_5$, oxo, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, optionally substituted 4-6 membered heterocycloalkyl, —$OR^a$, —$SR^a$, —$C(O)R^b$, —$C(O)NR^cR^d$, —$C(O)OR^a$, —$OC(O)R^b$, —$OC(O)NR^cR^d$, —$NR^cR^d$, —$NR^cC(O)R^b$, —$NR^cC(O)NR^cR^d$, —$NR^cC(O)OR^a$, —$S(O)(=NR^b)R^b$, —$S(O)R^b$, —$S(O)NR^cR^d$, —$S(O)_2R^b$, —$NR^cS(O)_2R^d$, —$S(O)_2NR^cR^d$, —$NR^cS(O)_2NR^cR^d$, —$NRS(O)(=NR^b)R^b$, —$SiR^GR^HR^I$, or —$B(OR^C)(OR^D)$; wherein, the optionally substituted substituent is selected from D, halo, CN, OH, $C_1$-$C_4$ alkyl, $C_1$-$C_4$ haloalkyl, —O—$C_1$-$C_4$ alkyl, —$OC_1$-$C_4$ haloalkyl;

each $R^A$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene, —$SiR^GR^HR^I$; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocyclalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, CN, halo, $C_1$-$C_4$ alkyl, $C_1$-$C_4$ haloalkyl, —$C_1$-$C_4$ alkyl-OH, —$C_1$-$C_4$ alkyl-CN, —$C_1$-$C_4$ alkyl-O—$C_1$-$C_4$ alkyl, —$C_1$-$C_4$ alkyl-O—$C_1$-$C_4$ haloalkyl, —$NO_2$, oxo, —$OR^a$, —$SR^a$, —$SF_5$, —$NHOR^a$, —$C(O)R^b$, —$C(O)NR^cR^d$, —$C(O)OR^a$, —$OC(O)R^b$, —$OC(O)NR^cR^d$, —$NR^cR^d$, —$NR^cC(O)R^b$, —$NR^cC(O)NR^cR^d$, —$NR^cC(O)OR^a$, —$B(OR^c)(OR^d)$, —$C(=NR^c)NR^cR^d$, —$NR^dC(=NR^c)NR^cR^d$, —$NR^dC(=NR)R^b$, —$P(O)R^eR^f$, —$P(O)OR^eOR^f$, —$OP(O)OR^eOR^f$, —$S(O)R^b$, —$S(O)NR^cR^d$, —$S(O)_2R^b$, —$NR^cS(O)_2R^b$, —$S(O)_2NR^cR^d$, —$NR^cS(O)_2NR^cR^d$, or —$NR^cS(O)(=NR^b)R^b$;

each $R^B$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, oxo, $C_1$-$C_4$ alkyl, $C_1$-$C_4$ haloalkyl, $C_1$-$C_4$ cyanoalkyl, $C_1$-$C_4$ alkyl-O—$C_1$-$C_4$ alkyl, $C_1$-$C_4$ alkyl-O—$C_1$-$C_4$ haloalkyl, —$SF_5$, —$OR^a$, —$C(O)R^b$, —$OC(O)NR^cR^d$, —$NR^cR^d$, —$NR^cC(O)R^b$, —$NR^cC(O)R^b$, —$NR^cC(O)OR^a$, —$S(O)R^b$, —$S(O)NR^cR^d$, —$S(O)_2R^b$, —$NR^cS(O)_2R^b$, —$S(O)_2NR^cR^d$, —$NR^cS(O)_2NR^cR^d$, or —$B(OR^c)(OR^d)$;

$R^C$ and $R^D$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, CN, halo, oxo, $C_1$-$C_4$ alkyl, $C_1$-$C_4$ haloalkyl, $C_1$-$C_4$ cyanoalkyl, $C_1$-$C_4$ alkyl-O—$C_1$-$C_4$ alkyl, $C_1$-$C_4$ alkyl-O—$C_1$-$C_4$ haloalkyl, —$SF_5$, —$OR^a$, —$OC(O)NR^cR^d$, —$NR^cR^d$, —$NR^cC(O)R^b$, —$S(O)NR^cR^d$, —$S(O)_2R^b$, —$NR^cS(O)_2R^b$, —$S(O)_2NR^cR^d$, —$NR^cS(O)_2NR^cR^d$ or —$B(OR^c)(OR^d)$;

or $R^C$ and $R^D$ together with the N atom to which they are attached form 4-7 membered heterocycloalkyl optionally substituted with 1, 2, 3, 4 or 5 substituent(s) independently selected from D, —OH, oxo, —CN, —$NH_2$, —$NH(C_1$-$C_4$ alkyl), —$N(C_1$-$C_4$ alkyl)$_2$, halo, $C_1$-$C_4$ alkyl, $C_1$-$C_4$ haloalkyl, $C_1$-$C_4$ cyanoalkyl, —$OC_1$-$C_4$ alkyl, or —$OC_1$-$C_4$ haloalkyl;

$R^a$ and $R^{a1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, halo, —OH, —CN, —$NH_2$, —$NH(C_1$-$C_4$ alkyl), —$N(C_1$-$C_4$ alkyl)$_2$, $C_1$-$C_4$ alkyl, —$OC_1$-$C_4$ alkyl, $C_1$-$C_4$ haloalkyl, or —$OC_1$-$C_4$ haloalkyl;

$R^b$ and $R^{b1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —OH, —CN, —$NH_2$, —$NH(C_1$-$C_4$ alkyl), —$N(C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_6$-$C_{10}$ aryl, $C_3$-$C_{10}$ cycloalkyl, 5-10 membered heteroaryl, or 4-10 membered heterocycloalkyl;

$R^c$, $R^d$, $R^c$, $R^{d1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl); wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl) is optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, —C(O)OR$^{a1}$, —C(O)R$^{b1}$, —S(O)$_2$R$^{b1}$, —$C_1$-$C_4$ alkyl-O—$C_1$-$C_4$ alkyl or $C_1$-$C_4$ alkyl-O—$C_1$-$C_4$ alkyl-O—;

or R$^c$ and R$^d$ together with the N atom to which they are attached form a 4-7 membered heterocycloalkyl optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl or $C_1$-$C_4$ alkoxy-$C_1$-$C_4$ alkoxy;

or R$^{c1}$ and R$^{d1}$ together with the N atom to which they are attached form a 4-7 membered heterocycloalkyl optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl or $C_1$-$C_4$ alkoxy-$C_1$-$C_4$ alkoxy;

R$^E$ and R$^e$ are each independently H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

R$^F$ and R$^f$ are each independently H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl; and R$^G$, R$^H$ and R$^I$ are each independently selected from optionally substituted $C_1$-$C_4$ alkyl or optionally substituted phenyl; wherein, the optionally substituted substituent is selected from D, halo, CN, OH, $C_1$-$C_4$ alkyl, $C_1$-$C_4$haloalkyl, —O—$C_1$-$C_4$ alkyl, —OC$_1$-$C_4$haloalkyl.

In some embodiments, ring A is $C_3$-$C_{14}$ cycloalkylene, 4-14 membered heterocycloalkylene, $C_6$-$C_{14}$ arylene or 5-14 membered heteroarylene.

In some embodiments, ring A is $C_3$-$C_{14}$ cycloalkylene.

In some embodiments, ring A is saturated $C_3$-$C_{14}$ cycloalkylene or partially unsaturated $C_3$-$C_{14}$ cycloalkylene.

In some embodiments, ring A is 4-14 membered heterocycloalkylene.

In some embodiments, ring A is saturated 4-14 membered heterocycloalkylene or partially unsaturated 4-14 membered heterocycloalkylene.

In some embodiments, ring A is $C_6$-$C_{14}$ arylene. In some embodiments, ring A is $C_6$-$C_{10}$ arylene.

In some embodiments, ring A is phenyl, naphthalenyl, anthracenyl, phenanthrenyl. In some embodiments, ring A is phenyl.

In some embodiments, ring A is 5-14 membered heteroarylene having 1, 2, 3 or 4 heteroatoms independently selected from N, O and S.

In some embodiments, ring A is 5-10 membered heteroarylene having 1, 2, 3 or 4 heteroatoms independently selected from N, O and S. In certain embodiments, ring A is 5-10 membered heteroarylene having one or two heteroatoms independently selected from N, O, or S. In some embodiments, ring A is 5-6 membered heteroarylene having 1, 2, 3 or 4 heteroatoms independently selected from N, O and S. In certain embodiments, ring A is 6-membered heteroarylene having 1, 2, or 3 heteroatoms independently selected from N. In certain embodiments, ring A is pyridinyl.

In certain embodiments, ring A is phenyl or 6-membered heteroarylene having 1, or 2 heteroatoms independently selected from N.

In some embodiments, ring A is pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c]thiophenyl, indazolyl, benzo[d]imidazolyl, pyrrolo[3,2-b]pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo[3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo[d][1,2,3]triazolyl, pyrazolo[4,3-b]pyridinyl, pyrazolo[4,3-c]pyridinyl, pyrazolo[3,4-c]pyridinyl, pyrazolo[3,4-b]pyridinyl, imidazo[4,5-b]pyridinyl, imidazo[4,5-c]pyridinyl, imidazo[4,5-c]pyridinyl, imidazo[4,5-b]pyridinyl, pyrrolo[3,2-c]pyridazinyl, pyrrolo[3,2-d]pyrimidinyl, pyrrolo[2,3-b]pyrazinyl, pyrrolo[2,3-d]pyridazinyl, pyrrolo[2,3-d]pyrimidinyl, pyrrolo[2,3-c]pyridazinyl, pyrrolo[3,4-c]pyridazinyl, pyrrolo[3,4-d]pyrimidinyl, pyrrolo[3,4-b]pyrazinyl, pyrrolo[3,4-d]pyridazinyl, pyrrolo[3,4-d]pyridazinyl, or 6H-pyrrolo[3,4-c]pyridazinyl.

In certain embodiments, ring A is phenyl or pyridinyl. In certain embodiments, ring A is phenyl or pyridin-4-yl.

In some embodiments, the moiety

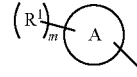

has the structure of $$Y^2 \overset{Y^3}{\underset{Y^1}{\bigcirc}} Y^5;$$

* wherein, $Y^1$, $Y^2$, $Y^3$, $Y^4$, $Y^5$ are each independently selected from N or $CR^1$.

In some embodiments, one of $Y^1$, $Y^2$, $Y^3$, $Y^4$, $Y^5$ is N.

In some embodiments, two of $Y^1$, $Y^2$, $Y^3$, $Y^4$, $Y^5$ are N.

In some embodiments, all of $Y^1$, $Y^2$, $Y^3$, $Y^4$, $Y^5$ are $CR^1$.

In some embodiments, the moiety $$\left( R^1 \right)_m \!\!-\!\! \bigcirc \!\! A \!\! \bigcirc \!\! *$$

has the structure of

*[chemical structures: $R^1$-substituted benzene, pyridine, pyridine, and pyridazine rings, each with attachment point *]*

In some embodiments, the moiety $$\left( R^1 \right)_m \!\!-\!\! \bigcirc \!\! A \!\! \bigcirc \!\! *$$

has the structure of

*[chemical structure: $R^1$-substituted benzene ring with attachment point *]*

In some embodiments, the moiety $$\left( R^1 \right)_m \!\!-\!\! \bigcirc \!\! A \!\! \bigcirc \!\! *$$

has the structure of

*[chemical structure: pyridine ring with $R^1$ substituents and $R^3$ substituent]*

In some embodiments, the moiety $$\left( R^1 \right)_m \!\!-\!\! \bigcirc \!\! A \!\! \bigcirc \!\! *$$

has the structure of

*[chemical structure: pyridine ring with $R^1$ substituents and attachment point *]*

In some embodiments, the moiety $$\left( R^1 \right)_m \!\!-\!\! \bigcirc \!\! A \!\! \bigcirc \!\! *$$

has the structure of

*[chemical structure: pyridazine ring with $R^1$ substituents and attachment point *]*

In certain embodiments, the moiety $$\left( R^1 \right)_m \!\!-\!\! \bigcirc \!\! A \!\! \bigcirc \!\! *$$

has the structure of

In certain embodiments, the moiety $$\left(R^1\right)_m \!\!-\!\! \bigcirc\!\!A \!\!-\!\! *$$

has the structure of

In some embodiments, ring B is partially unsaturated 5-14 membered heterocycloalkylene, $C_6$-$C_{14}$ arylene or 5-14 membered heteroarylene.

In some embodiments, ring B is partially unsaturated 5-14 membered heterocycloalkylene.

In some embodiments, ring B is $C_6$-$C_{14}$ arylene. In some embodiments, ring B is $C_6$-$C_{10}$ arylene. In some embodiments, ring B is phenyl, naphthalenyl, anthracenyl, phenanthrenyl. In some embodiments, ring B is phenyl.

In some embodiments, ring B is 5-14 membered heteroarylene having 1, 2, 3 or 4 heteroatoms independently selected from N, O and S. In some embodiments, ring B is 5-10 membered heteroarylene having 1, 2, 3 or 4 heteroatoms independently selected from N, O and S. In some embodiments, ring B is 5-6 membered heteroarylene having 1, 2, or 3 heteroatoms independently selected from N, O and S. In some embodiments, ring B is 5-6 membered heteroarylene having 1, or 2 heteroatoms independently selected from N, O and S. In some embodiments, ring B is 5-6 membered heteroarylene having 1, or 2 heteroatoms independently selected from N.

In some embodiments, ring B is pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c]thiophenyl, indazolyl, benzo[d]imidazolyl, pyrrolo[3,2-b]pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo[3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo[d][1,2,3]triazolyl, pyrazolo[4,3-b]pyridinyl, pyrazolo[4,3-c]pyridinyl, pyrazolo[3,4-c]pyridinyl, pyrazolo[3,4-b]pyridinyl, imidazo[4,5-b]pyridinyl, imidazo[4,5-c]pyridinyl, imidazo[4,5-c]pyridinyl, imidazo[4,5-b]pyridinyl, pyrrolo[3,2-c]pyridazinyl, pyrrolo[3,2-d]pyrimidinyl, pyrrolo[2,3-b]pyrazinyl, pyrrolo[2,3-d]pyridazinyl, pyrrolo[2,3-d]pyrimidinyl, pyrrolo[2,3-c]pyridazinyl, pyrrolo[3,4-c]pyridazinyl, pyrrolo[3,4-d]pyrimidinyl, pyrrolo[3,4-b]pyrazinyl, pyrrolo[3,4-d]pyridazinyl, pyrrolo[3,4-d]pyrimidinyl, or 6H-pyrrolo[3,4-c]pyridazinyl.

In certain embodiments, ring B is 5- or 6-membered heteroarylene. In certain embodiments, ring A is imidazolyl, pyridinyl, or pyridazinyl. In certain embodiments, ring A is imidazolyl or pyridinyl.

In some embodiments, the moiety has the structure of wherein, the position * is attached to ring A, the position ** is attached to C=O;

$X^1$, $X^2$, $X^3$, $X^4$ are each independently N or $CR^2$;

$X^5$ is $NR^1$, O or S.

In some embodiments, the moiety has the structure of

In some embodiments, one of $X^1$, $X^2$, $X^3$, $X^4$ is N, wherein $X^1$, $X^2$, $X^3$, and $X^4$ are each as defined herein. In certain embodiments, one of $X^1$, $X^2$, $X^3$, and $X^4$ is N; and the remaining three are each independently $CR^2$, wherein $R^2$ is as defined herein. In certain embodiments, two of $X^1$, $X^2$, $X^3$, and $X^4$ are each N; and the remaining two are each independently $CR^2$, wherein $R^2$ is as defined herein. In certain embodiments, $X^1$, $X^2$, $X^3$, and $X^4$ are each independently $CR^2$, wherein $R^2$ is as defined herein.

In certain embodiments, the moiety has the structure of wherein $R^2$, $X^1$, and $X^4$ are each as defined herein.

In certain embodiments, the moiety has the structure of wherein $X^1$, $X^2$, and $X^3$ are each as defined herein. In certain embodiments, one of $X^1$, $X^2$, and $X^3$ is N; and the remaining two are each independently $CR^2$, wherein $R^2$ is as defined herein. In certain embodiments, two of $X^1$, $X^2$, and $X^3$ are N; and the remaining one is $CR^2$, wherein $R^2$ is as defined herein. In certain embodiments, $X^1$, $X^2$, and $X^3$ are each independently $CR^2$, wherein $R^2$ is as defined herein.

In certain embodiments, the moiety has the structure of wherein each $X^1$, $X^3$, and $X^5$ is as defined herein. In certain embodiments, each $X^1$ and $X^3$ is independently $CR^2$; and $X^5$ is $NR^2$, O or S; wherein each $R^2$ is as defined herein. In certain embodiments, $X^1$ is N; $X^3$ is $CR^2$; and $X^5$ is $NR^2$, O or S; wherein each $R^2$ is as defined herein. In certain embodiments, $X^1$ is $CR^2$; $X^3$ is N; and $X^5$ is $NR^2$, O or S; wherein each $R^2$ is as defined herein. In certain embodiments, $X^1$ is N; $X^3$ is N; and $X^5$ is $NR^2$, O or S; wherein $R^2$ is as defined herein.

In some embodiments, the moiety has the structure of

-continued wherein each $R^2$ is as defined herein.

In some embodiments, the moiety has the structure of wherein, each R$^2$ is as defined herein.

In some embodiments, the moiety has the structure of

-continued wherein, each R$^2$ is as defined herein.

In some embodiments, the moiety has the structure of wherein each R$^2$ is as defined herein. In certain embodiments, the moiety has the structure of wherein each $R^2$ is as defined herein. In certain embodiments, the moiety has the structure of wherein each $R^2$ is as defined herein. In certain embodiments, the moiety has the structure of wherein each $R^2$ is as defined herein. In certain embodiments, the moiety has the structure of wherein each $R^2$ is as defined herein. In certain embodiments, the moiety has the structure of wherein each $R^2$ is as defined herein. In certain embodiments, the moiety has the structure of In some embodiments, m is 0.
In some embodiments, m is 1.
In some embodiments, m is 2.
In some embodiments, m is 3.
In some embodiments, m is 4.
In some embodiments, m is 5.
In some embodiments, n is 0.
In some embodiments, n is 1.
In some embodiments, n is 2.
In some embodiments, n is 3.
In some embodiments, n is 4.
In some embodiments, n is 5.
In some embodiments, each $R^1$ is independently H, D, halogen, —CN, —NO$_2$, —N$_3$, —SF$_5$, oxo, C$_1$-C$_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl, —$NR^CR^D$, —$OR^A$, —$SR^A$, —$NR^COR^A$, —$C(O)R^B$, —$C(O)$ $NR^CR^D$, —$C(O)OR^A$, —$OC(O)R^B$, —$NR^CC(O)R^B$, —$S(O)$ $R^B$, —$S(O)_2R^B$, —$S(O)NR^CR^D$, —$NR^CS(O)_2R^D$, —$S(O)_2NR^CR^D$, —$NR^CS(O)_2NR^CR^D$, —$NR^CS(O)$ (=$NR^B)R^B$, —$SiR^GR^HR^I$, —$B(OR^C)(OR^D)$, —$P(O)R^ER^F$, —$P(O)OR^EOR^F$, —$OP(O)OR^EOR^F$; wherein, the $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl is optionally substituted with 1, 2, 3, 4 or 5 substituent(s) independently selected from $R^{1A}$.

In some embodiments, each $R^1$ is independently H, D, halogen, —CN, —$NO_2$, —$N_3$, —$SF_5$, oxo.

In some embodiments, each $R^1$ is independently H. In some embodiments, each $R^1$ is independently D.

In some embodiments, each $R^1$ is independently halogen. In some embodiments, each $R^1$ is independently —F, —Cl, —Br, —I. In some embodiments, each $R^1$ is —F. In some embodiments, each $R^1$ is —Cl. In some embodiments, each $R^1$ is Br. In some embodiments, each $R^1$ is —I.

In some embodiments, each $R^1$ is independently —CN. In some embodiments, each $R^1$ is independently —$NO_2$. In some embodiments, each $R^1$ is independently —$N_3$. In some embodiments, each $R^1$ is independently —$SF_5$. In some embodiments, each $R^1$ is independently oxo.

In some embodiments, each $R^1$ is independently $NR^CR^D$. In some embodiments, for example, each $R^1$ is independently —$NH_2$, —$NHCH_3$, —$NHCH(CH_3)_2$, —$NHCH_3$, —$N(CH_3)_2$, —$N(CH_2CH_3)_2$.

In some embodiments, each $R^1$ is independently $OR^A$. In some embodiments, for example, each $R^1$ is independently —OH, —$OCH_3$, —$OCH_2CH_3$, —$OCH_2CH_2CH_3$, —$OCH(CH_3)_2$, —$OCH_2F$, —$OCHF_2$, —$OCF_3$, —$OCH_2CH_2F$, —$OCH_2CHF_2$, —$OCH_2CF_3$, —$OCH_2CN$, —$OCH_2CONH_2$, —$OCH_2CH_2OCH_3$. In some embodiments, each $R^1$ is independently —$OCH_3$. In some embodiments, each $R^1$ is independently —$OCH_2CH_3$. In some embodiments, each $R^1$ is independently —$OCH(CH_3)_2$. In some embodiments, each $R^1$ is independently —$OCF_3$. In some embodiments, each $R^1$ is independently —$OCHF_2$. In some embodiments, each $R^1$ is independently —$OCH_2F$. In some embodiments, each $R^1$ is independently —$OCF_3$. In some embodiments, each $R^1$ is independently —$OCH_2CH_2F$. In some embodiments, each $R^1$ is independently —$OCH_2CHF_2$. In some embodiments, each $R^1$ is independently —$OCH_2CF_3$. In some embodiments, each $R^1$ is independently —$OCH_2CN$. In some embodiments, each $R^1$ is independently —$OCH_2CONH_2$.

In some embodiments, each $R^1$ is independently —$SR^A$. In some embodiments, each $R^1$ is independently —$SCH_3$. In some embodiments, each $R^1$ is independently —$SCH_2CH_3$.

In some embodiments, each $R^1$ is independently —$C(O)$ $R^B$. In some embodiments, each $R^1$ is independently —CHO, —$C(O)CH_3$, —$C(O)CH_2CH_3$

22

-continued

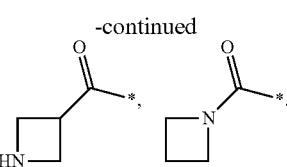

In some embodiments, each $R^1$ is independently —$C(O)$ $NR^CR^D$. In some embodiments, each $R^1$ is independently —$CONH_2$, —$CONHCH_3$, —$CON(CH_3)_2$, In some embodiments, each $R^1$ is independently —$C(O)$ $OR^A$. In some embodiments, each $R^1$ is independently —COOH. In some embodiments, each $R^1$ is independently —$OC(O)R^B$.

In some embodiments, each $R^1$ is independently —$NR^CC(O)R^B$.

In some embodiments, each $R^1$ is independently —$S(O)$ $R^B$. In some embodiments, for example, each $R^1$ is independently —$S(O)CH_3$, —$S(O)CH_2CH_3$, In some embodiments, each $R^1$ is independently —$S(O)_2R^B$. In some embodiments, for example, each $R^1$ is independently —$S(O)_2CH_3$, —$S(O)_2CH_2CH_3$, In some embodiments, each $R^1$ is independently —$S(O)$ $NR^CR^D$. In some embodiments, for example, each $R^1$ is independently —$S(O)_2NH_2$, —$S(O)_2NHCH_3$, —$S(O)_2N(CH_3)_2$.

In some embodiments, each $R^1$ is independently —$NR^CS(O)_2R^D$. In some embodiments, each $R^1$ is independently —$NHS(O)_2CH_3$. In some embodiments, each $R^1$ is independently —$S(O)_2NR^CR^D$. In some embodiments, each $R^1$ is independently —$NR^CS(O)_2NR^CR^D$. In some embodiments, each $R^1$ is independently —$NR^CS(O)(=NR^B)R^B$.

In some embodiments, each $R^1$ is independently —$SiR^GR^HR^I$. In some embodiments, each $R^1$ is independently —$B(OR^C)(OR^D)$. In some embodiments, each $R^1$ is independently —$P(O)R^ER^F$. In some embodiments, each $R^1$ is independently —$P(O)(CH_3)_2$. In some embodiments, each $R^1$ is independently —$P(O)OR^EOR^F$. In some embodiments, each $R^1$ is independently —$OP(O)OR^EOR^F$.

In some embodiments, each $R^1$ is independently $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl; wherein, the $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, phenyl or 5-6 membered heteroaryl is optionally substituted with 1, 2, 3, 4 or 5 substituent(s) independently selected from $R^{1A}$.

In some embodiments, each $R^1$ is independently $C_1$-$C_6$ alkyl optionally substituted with 1, 2, 3, 4 or 5 substituent(s) independently selected from $R^{1A}$.

In some embodiments, each $R^1$ is independently —$CD_3$, —$CH_3$, —$CH_2CH_3$, n-propyl, i-propyl, n-butyl, i-butyl, t-butyl, —$CH_2F$, —$CHF_2$, —$CF_3$, —$CH_2CH_2F$, —$CH_2CHF_2$, —$CH_2CF_3$, —$CH_2OH$, —$CH(OH)CH_3$, —$CH_2CH_2OH$, —$CH_2OCH_3$, —$CH_2OCHF_2$, —$CH_2OCH_2F$, —$CH_2OCF_3$, —$CH(OCH_3)CH_3$, —$CH_2CH_2NH_2$, —$CH(NH_2)CH_3$, —$CH_2N(CH_3)_2$, —$CH_2CH_2N(CH_3)_2$, —$CH_2CN$, —$CH_2C(O)NH_2$, benzyl.

In some embodiments, each $R^1$ is independently $C_2$-$C_6$ alkenyl optionally substituted with 1, 2, 3, 4 or 5 substituent (s) independently selected from $R^{1A}$. In some embodiments, for example, each $R^1$ is independently —$CH=CH_2$, —$CH=CHCH_3$.

In some embodiments, each $R^1$ is independently $C_2$-$C_6$ alkynyl optionally substituted with 1, 2, 3, 4 or 5 substituent (s) independently selected from $R^{1A}$. In some embodiments, for example, each $R^1$ is independently —$C\equiv CH$, —$C\equiv CCH_3$, —$C\equiv CD$, —$C\equiv CCD_3$.

In some embodiments, each $R^1$ is independently $C_3$-$C_6$ cycloalkyl optionally substituted with 1, 2, 3, 4 or 5 substituent(s) independently selected from $R^{1A}$. In some embodiments, each $R^1$ is independently cyclopropyl, cyclobutyl, cyclopentyl, cyclohexyl, each ring is optionally substituted with 1, 2, 3, 4 or 5 substituent(s) independently selected from $R^{1A}$.

In some embodiments, each $R^1$ is independently 4-6 membered heterocycloalkyl having 1 or 2 heteroatom(s) selected from N, O, S and B, and wherein the heteroatoms can be optionally substituted by one or more oxo (e.g., S(O), or $S(O)_2$) optionally substituted with 1, 2, 3, 4 or 5 substituent(s) independently selected from $R^{1A}$.

In some embodiments, each $R^1$ is independently azetidinyl, oxetanyl, thietanyl, pyrrolidinyl, tetrahydrofuranyl, tetrahydrothiophenyl, piperidinyl, tetrahydropyranyl, tetrahydrothiopyranyl, piperazinyl, morpholinyl, or thiomorpholine dioxide, each ring is optionally substituted with 1, 2, 3, 4 or 5 substituent(s) independently selected from $R^{1A}$. In some embodiments, one of $R^1$ In some embodiments, each $R^1$ is independently phenyl optionally substituted with 1, 2, 3, 4 or 5 substituent(s) independently selected from $R^{1A}$. In some embodiments, one of $R^1$ is phenyl.

In some embodiments, each $R^1$ is independently 5-6 membered heteroaryl optionally substituted with 1, 2, 3, 4 or 5 substituent(s) independently selected from $R^{1A}$. In some embodiments, each $R^1$ is independently pyrrolyl, oxazolyl, isoxazolyl, thiadiazolyl, oxadiazolyl, pyridinyl, pyrimidinyl, pyrazinyl; each is optionally substituted with 1, 2, 3, 4 or 5 substituent(s) independently selected from $R^{1A}$. In some embodiments, one of $R^1$ is In certain embodiments, each $R^1$ is independently (i) H, D, halo, or —$OR^A$; or (ii) $C_1$-$C_6$ alkyl, $C_2$-$C_6$ alkynyl; each is optionally substituted with 1, 2, 3, 4, or 5 substituents, each of which is independently $R^{1A}$; wherein $R^A$ and $R^{1A}$ are each as defined herein. In certain embodiments, each $R^1$ is independently (i) H, D, halo, or —$OR^A$; or (ii) $C_1$-$C_6$ alkyl, optionally substituted with 1, 2, 3, 4, or 5 substituents, each of which is independently $R^{1A}$; wherein $R^A$ and $R^{1A}$ are each as defined herein. In certain embodiments, each $R^1$ is independently H, —F, —$C_1$, —$CH_3$, —$CHF_2$, —$CF_3$, —$OCH_3$, —$OCHF_2$, —$OCF_3$, or —$C\equiv CH$. In certain embodiments, each $R^1$ is independently H, —F, —Cl, —$CH_3$, —$CF_3$, or —$OCH_3$.

In certain embodiments, one of the $R^1$ groups is —F. In certain embodiments, one of the $R^1$ groups is —Cl, —$CH_3$, or —$CF_3$. In certain embodiments, one of the $R^1$ groups is —$OCH_3$.

In certain embodiments, three of the $R^1$ groups are not H. In certain embodiments, three of the $R^1$ groups are not H; the first of the three is —F; the second of the three is —Cl, —$CH_3$, or —$CF_3$; and the third of the three is —$OCH_3$. In certain embodiments, three of the $R^1$ groups are not H; the first of the three is —F; the second of the three is —Cl; and the third of the three is —$OCH_3$.

In some embodiments, two $R^1$ together with the atom(s) to which they are attached form oxo, $C_3$-$C_7$ cycloalkyl or 4-7 membered heterocycloalkyl; wherein, the $C_3$-$C_7$ cycloalkyl or 4-7 membered heterocycloalkyl is optionally substituted with 1, 2, 3, 4 or 5 substituent(s) independently selected from $R^{1A}$.

In some embodiments, two $R^1$ together with the atom to which they are attached form oxo.

In some embodiments, two $R^1$ together with the atom(s) to which they are attached form $C_3$-$C_7$ cycloalkyl optionally substituted with 1, 2, 3, 4 or 5 substituent(s) independently selected from $R^{1A}$.

In some embodiments, two $R^1$ together with the atom(s) to which they are attached form 4-7 membered heterocycloalkyl optionally substituted with 1, 2, 3, 4 or 5 substituent(s) independently selected from $R^{1A}$.

In some embodiments, each $R^{1A}$ is independently D, halogen, —CN, —$NO_2$, —$N_3$, oxo, —$OR^a$, —$NR^cR^d$, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl; wherein, the $C_1$-$C_6$ alkyl, $C_2$-$C_6$ alkenyl, $C_2$-$C_6$ alkynyl, $C_3$-$C_6$ cycloalkyl or 4-6 membered heterocycloalkyl is optionally substituted with D, halogen, —CN, —OH, —$NH_2$, oxo, —$NR^cR^d$, —$OR^a$, —$SR^a$, $C_1$-$C_6$ alkyl, $C_1$-$C_6$ haloalkyl.

In some embodiments, each $R^{1A}$ is independently D, halogen, —CN, —$NO_2$, —$N_3$, oxo, —$OR^a$, —$NR^cR^d$. In some embodiments, each $R^{1A}$ is independently D. In some embodiments, each $R^{1A}$ is independently halogen (such as —F, —Cl, —Br, —I). In some embodiments, each $R^{1A}$ is independently —CN. In some embodiments, each $R^{1A}$ is independently —$NO_2$. In some embodiments, each $R^{1A}$ is independently —$N_3$. In some embodiments, each $R^{1A}$ is independently oxo. In some embodiments, each $R^{1A}$ is independently —$OR^a$ (such as —OH, —$OCH_3$, —$OCH_2CH_3$, —$OCH_2CH_2CH_3$, —$OCH(CH_3)_2$, —$OCH_2F$, —$OCHF_2$, —$OCF_3$). In some embodiments, each $R^{1A}$ is independently —$NR^cR^d$ (such as —$NH_2$, —$NHCH_3$, —$N(CH_3)_2$, —$NHCH_2CH_2OH$, —$N(CH_3)CH_2CH_2OH$).

In some embodiments, each $R^{1A}$ is independently $C_1$-$C_6$ alkyl optionally substituted with D, halogen, —CN, —OH, —$NH_2$, oxo, —$NR^cR^d$, —$OR^a$, —$SR^a$.

In some embodiments, each $R^{1A}$ is independently $C_2$-$C_6$ alkenyl optionally substituted with D, halogen, —CN, —OH, —$NH_2$, oxo, —$NR^cR^d$, —$OR^a$, —$SR^a$.

In some embodiments, each $R^{1A}$ is independently $C_2$-$C_6$ alkynyl optionally substituted with D, halogen, —CN, —OH, —$NH_2$, oxo, —$NR^cR^d$, —$OR^a$, —$SR^a$.

In some embodiments, each $R^{1A}$ is independently $C_3$-$C_6$ cycloalkyl (such as $C_3$ cycloalkyl, $C_4$ cycloalkyl, $C_5$ cycloalkyl, $C_6$ cycloalkyl) optionally substituted with D, halogen, —CN, —OH, —$NH_2$, oxo, —$NR^cR^d$, —$OR^a$, —$SR^a$, $C_1$-$C_6$ alkyl, $C_1$-$C_6$ haloalkyl.

In some embodiments, each $R^{1A}$ is independently 4-6 membered heterocycloalkyl optionally substituted with D, halogen, —CN, —OH, —$NH_2$, oxo, —$NR^cR^d$, —$OR^a$, —$SR^a$, $C_1$-$C_6$ alkyl, $C_1$-$C_6$ haloalkyl.

In some embodiments, each $R^2$ is independently H, D, —CN, —$NO_2$, —$N_3$, oxo, —$SF_5$, halogen, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, —$NR^cR^D$, —$OR^A$, —$SR^A$, —$NR^cOR^A$, —$C(O)R^B$, —$C(O)NR^cR^D$, —$C(O)OR^A$, —$OC(O)R^B$, —$NR^cC(O)R^B$, —$S(O)R^B$, —$S(O)_2R^B$, —$S(O)NR^cR^D$, —$NR^cS(O)_2R^D$, —$S(O)_2NR^cR^D$, —$NR^cS(O)_2NR^cR^D$, —$NR^cS(O)(=NR^B)R^B$, —$SiR^GR^HR^I$, —$B(OR^c)(OR^D)$, —$P(O)R^ER^F$, —$P(O)OR^EOR^F$, —$OP(O)OR^EOR^F$; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl is optionally substituted with 1, 2, 3, 4 or 5 substituent(s) independently selected from $R^{2A}$.

In some embodiments, each $R^2$ is independently H, D, —CN, —$NO_2$, —$N_3$, oxo, —$SF_5$, halogen. In some embodiments, each $R^2$ is independently H. In some embodiments, each $R^2$ is independently is D. In some embodiments, each $R^2$ is independently is —CN. In some embodiments, each $R^2$ is independently is —$NO_2$. In some embodiments, each $R^2$ is independently is —$N_3$. In some embodiments, each $R^2$ is independently is —$SF_5$.

In some embodiments, each $R^2$ is independently is halogen. In some embodiments, each $R^2$ is independently is —F, —Cl, —Br or —I. In some embodiments, each $R^2$ is independently —F. In some embodiments, each $R^2$ is independently —Cl. In some embodiments, each $R^2$ is independently —Br. In some embodiments, each $R^2$ is independently —I.

In some embodiments, each $R^2$ is independently is —$NR^cR^D$. In some embodiments, each $R^2$ is independently is —$NH_2$, —$NHCH_3$, —$N(CH_3)_2$, —$NHCH_2CH_3$, —$N(CH_2CH_3)_2$, —$NHCH_2CH_2CH_3$, —$N(CH_2CH_2CH_3)_2$, —$NHCH(CH_3)_2$, —$NHCH_2CH_2OH$.

In some embodiments, each $R^2$ is independently is —$OR^A$. In some embodiments, each $R^2$ is independently —OH, —$OCH_3$, —$OCH_2CH_3$, —$OCH_2CH_2CH_3$, —$OCH(CH_3)_2$, —$OCH_2F$, —$OCHF_2$, $OCF_3$, -continued In some embodiments, each $R^2$ is independently —$SR^A$. In some embodiments, each $R^2$ is independently —SMe.

In some embodiments, each $R^2$ is independently —$NR^cOR^A$. In some embodiments, $R^2$ is —$C(O)R^B$. In some embodiments, $R^2$ is —$C(O)CH_3$, —$C(O)CH_2CH_3$, —$C(O)CH(CH_3)_2$, In some embodiments, each $R^2$ is independently —$C(O)R^B$.

In some embodiments, each $R^2$ is independently —$C(O)NR^cR^D$. In some embodiments, $R^2$ is —$C(O)NH_2$, —$C(O)NHCH_3$, —$C(O)N(CH_3)_2$.

In some embodiments, each $R^2$ is independently —$C(O)OR^A$. In some embodiments, each $R^2$ is independently —$OC(O)R^B$.

In some embodiments, each $R^2$ is independently —$NR^CC$(O)$R^B$. In some embodiments, $R^2$ is —NHC(O)CH$_3$, —NCH$_3$C(O)CH$_3$, In some embodiments, each $R^2$ is independently —S(O)$R^B$. In some embodiments, each $R^2$ is independently —S(O)$_2R^B$. In some embodiments, each $R^2$ is independently —S(O)NR$^C$R$^D$. In some embodiments, each $R^2$ is independently —NR$^C$S(O)$_2$R$^D$. In some embodiments, each $R^2$ is independently —S(O)$_2$NR$^C$R$^D$. In some embodiments, each $R^2$ is independently —NR$^C$S(O)$_2$NR$^C$R$^D$. In some embodiments, each $R^2$ is independently —NR$^C$S(O)(=NR$^B$)R$^B$ In some embodiments, each $R^2$ is independently —SiR$^G$R$^H$R$^I$. In some embodiments, each $R^2$ is independently —B(OR$^C$)(OR$^D$). In some embodiments, each $R^2$ is independently —P(O)R$^E$R$^F$. In some embodiments, each $R^2$ is independently —P(O)OR$^E$OR$^F$. In some embodiments, each $R^2$ is independently —OP(O)OR$^E$OR$^F$.

In some embodiments, each $R^2$ is independently $C_1$-$C_6$ alkyl optionally substituted with 1, 2, 3, 4 or 5 substituent(s) independently selected from $R^{2A}$. In some embodiments, for example, but not limited to, $R^2$ is methyl, ethyl, n-propyl, i-propyl, n-butyl, i-butyl, t-butyl, —CH$_2$F, —CHF$_2$, —CF$_3$, —CH$_2$CH$_2$F, —CH$_2$CHF$_2$, —CH$_2$CF$_3$, —CD$_3$, —CH$_2$OH, —CH$_2$OMe, —CH$_2$CN, -continued In some embodiments, $R^2$ is methyl or CD$_3$.

In some embodiments, each $R^2$ is independently $C_2$-$C_6$ alkenyl optionally substituted with 1, 2, 3, 4 or 5 substituent(s) independently selected from $R^{2A}$.

In some embodiments, each $R^2$ is independently $C_2$-$C_6$ alkynyl optionally substituted with 1, 2, 3, 4 or 5 substituent(s) independently selected from $R^{2A}$. In some embodiments, $R^2$ is In some embodiments, each $R^2$ is independently $C_3$-$C_{10}$ cycloalkyl optionally substituted with 1, 2, 3, 4 or 5 substituent(s) independently selected from $R^{2A}$.

In some embodiments, each $R^2$ is independently saturated $C_3$-$C_{10}$ cycloalkyl or partially unsaturated $C_3$-$C_{10}$ cycloalkyl; each is optionally substituted with 1, 2, 3, 4 or 5 substituent(s) independently selected from $R^{2A}$.

In some embodiments, each $R^2$ is independently cyclopropyl, cyclobutyl, cyclopentyl, cyclohexyl; each is optionally substituted with 1, 2, 3, 4 or 5 substituent(s) independently selected from $R^{2A}$. In some embodiments, one of $R^2$ is In some embodiments, each $R^2$ is independently 4-10 membered heterocycloalkyl optionally substituted with 1, 2, 3, 4 or 5 substituent(s) independently selected from $R^{2A}$.

In some embodiments, each $R^2$ is independently saturated 4-10 membered heterocycloalkyl or partially unsaturated 4-10 membered heterocycloalkyl; each is optionally substituted with 1, 2, 3, 4 or 5 substituent(s) independently selected from $R^{2A}$.

In some embodiments, each $R^2$ is independently azetidinyl, oxetanyl, thietanyl, pyrrolidinyl, imidazolidinyl, pyrazolidinyl; each is optionally substituted with 1, 2, 3, 4 or 5 substituent(s) independently selected from $R^{2A}$. In some embodiments, one of $R^2$ is In some embodiments, each $R^2$ is independently $C_6$-$C_{10}$ aryl optionally substituted with 1, 2, 3, 4 or 5 substituent(s) independently selected from $R^{2A}$. In some embodiments, each $R^2$ is independently phenyl, naphthalenyl; each is optionally substituted with 1, 2, 3, 4 or 5 substituent(s) independently selected from $R^{2A}$.

In some embodiments, each $R^2$ is independently 5-10 membered heteroaryl optionally substituted with 1, 2, 3, 4 or 5 substituent(s) independently selected from $R^{2A}$.

In some embodiments, each $R^2$ is independently pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c]thiophenyl, indazolyl, benzo[d]imidazolyl, pyrrolo[3,2-b]pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo[3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo[d][1,2,3]triazolyl, pyrazolo[4,3-b]pyridinyl, pyrazolo[4,3-c]pyridinyl, pyrazolo[3,4-c]pyridinyl, pyrazolo[3,4-b]pyridinyl, imidazo[4,5-b]pyridinyl, imidazo[4,5-c]pyridinyl, imidazo[4,5-c]pyridinyl, imidazo[4,5-b]pyridinyl, pyrrolo[3,2-c]pyridazinyl, pyrrolo[3,2-d]pyrimidinyl, pyrrolo[2,3-b]pyrazinyl, pyrrolo[2,3-d]pyridazinyl, pyrrolo[2,3-d]pyrimidinyl, pyrrolo[2,3-c]pyridazinyl, pyrrolo[3,4-c]pyridazinyl, pyrrolo[3,4-d]pyrimidinyl, pyrrolo[3,4-b]pyrazinyl, pyrrolo[3,4-d]pyridazinyl, pyrrolo[3,4-d]pyrimidinyl, 6H-pyrrolo[3,4-c]pyridazinyl; each is optionally substituted with 1, 2, 3, 4 or 5 substituent(s) independently selected from $R^{2A}$. In some embodiments, one of $R^2$ is In certain embodiments, each $R^2$ is independently (i) H, D, —CN, or halo; or (ii) $C_1$-$C_6$ alkyl or 5-10 membered heteroaryl, each optionally substituted with 1, 2, 3, 4, or 5 substituents, each of which is independently $R^{2A}$, wherein $R^{2A}$ is as defined herein. In certain embodiments, each $R^2$ is independently (i) H, D, or —CN; or (ii) $C_1$-$C_6$ alkyl or 5-membered heteroaryl, each optionally substituted with 1, 2, 3, 4, or 5 substituents, each of which is independently $R^{2A}$, wherein $R^{2A}$ is as defined herein. In certain embodiments, each $R^2$ is independently H, D, —CN, methyl, or 1-methylpyrazolyl. In certain embodiments, each $R^2$ is independently H or methyl.

In certain embodiments, one of the $R^2$ groups is (i) —CN or halo; or (ii) $C_1$-$C_6$ alkyl or 5-10 membered heteroaryl, each optionally substituted with 1, 2, 3, 4, or 5 substituents, each of which is independently $R^{2A}$, wherein $R^{2A}$ is as defined herein. In certain embodiments, one of the $R^2$ groups is —CN, methyl, or 1-methylpyrazolyl. In certain embodiments, one of the $R^2$ groups is methyl.

In certain embodiments, one of the $R^2$ groups is (i) —CN or halo; or (ii) $C_1$-$C_6$ alkyl or 5-10 membered heteroaryl, each optionally substituted with 1, 2, 3, 4, or 5 substituents, each of which is independently $R^{2A}$, wherein $R^{2A}$ is as defined herein; and the remaining $R^2$ groups are each H. In certain embodiments, one of the $R^2$ groups is —CN, methyl, or 1-methylpyrazolyl; and the remaining $R^2$ groups are each H. In certain embodiments, one of the $R^2$ groups is methyl; and the remaining $R^2$ groups are each H.

In some embodiments, two $R^2$ together with the atom(s) to which they are attached form oxo, $C_3$-$C_7$ cycloalkyl, 4-7 membered heterocycloalkyl; wherein, the $C_3$-$C_7$ cycloalkyl, 4-7 membered heterocycloalkyl is optionally substituted by 1, 2, 3 or 4 substituents independently selected from $R^{2A}$.

In some embodiments, two $R^2$ together with the atom to which they are attached form oxo.

In some embodiments, two $R^2$ together with the atom(s) to which they are attached form $C_3$-$C_7$ cycloalkyl optionally substituted by 1, 2, 3 or 4 substituents independently selected from $R^{2A}$.

In some embodiments, two $R^2$ together with the atom(s) to which they are attached form 4-7 membered heterocycloalkyl optionally substituted by 1, 2, 3 or 4 substituents independently selected from $R^{2A}$.

In some embodiments, each $R^{2A}$ is independently D, halogen, —CN, —OH, —NH$_2$, —NO$_2$, —SF$_5$, oxo, $C_1$-$C_4$ alkyl, $C_2$-$C_4$ alkenyl, $C_2$-$C_4$ alkynyl, $C_3$-$C_6$ cycloalkyl, 4-6 membered heterocycloalkyl, phenyl, 5-6 membered heteroaryl, —NR$^c$R$^d$, —OR$^a$, —SR$^a$, —C(O)R$^b$, —C(O)NR$^c$R$^d$, —C(O)OR$^a$, —OC(O)R$^b$, —OC(O)NR$^c$R$^d$, —NR$^c$C(O)R$^b$, —NR$^c$C(O)NR$^c$R$^d$, —NR$^c$C(O)OR$^a$, —S(O)(=NR$^b$)R$^b$, —S(O)R$^b$, —S(O)NR$^c$R$^d$, S(O)$_2$R$^b$, —NR$^c$S(O)$_2$R$^d$, —S(O)$_2$NR$^c$R$^d$, —NR$^c$S(O)$_2$NR$^c$R$^d$, or —NR$^c$S(O)(=NR$^b$)R$^b$; wherein, the $C_1$-$C_4$ alkyl, $C_2$-$C_4$ alkenyl, $C_2$-$C_4$ alkynyl, $C_3$-$C_6$ cycloalkyl, 4-6 membered heterocycloalkyl is optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently D, halogen, —CN, —OH, —NH$_2$, —NO$_2$, —SF$_5$, oxo.

In some embodiments, each $R^{2A}$ is independently $C_1$-$C_4$ alkyl optionally substituted with D, halogen, —CN, —OH, —NH$_2$, oxo, —NR$^{c1}$R$^{d1}$, —OR$^{a1}$, —SR$^{a1}$, $C_1$-$C_6$alkyl, $C_1$-$C_6$haloalkyl. In some embodiments, each $R^{2A}$ is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$F, —CHF$_2$, —CF$_3$, —CH$_2$CH$_2$F, —CH$_2$CHF$_2$, —CH$_2$CF$_3$, —CF$_2$CH$_3$, —CF$_2$CF$_3$, —CF$_2$CH$_2$CH$_3$, —CH$_2$OH, —CH$_2$CH$_2$OH, —CH(OH)CH$_3$, —CH$_2$CH$_2$CH$_2$OH, —CH(OH)CH$_2$CH$_2$OH, —CH$_2$CN, —CH$_2$CH$_2$CN, —CH$_2$CH$_2$CH$_2$CN.

In some embodiments, each $R^{2A}$ is independently $C_2$-$C_4$ alkenyl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently $C_2$-$C_4$ alkynyl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently $C_3$-$C_6$ cycloalkyl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently 4-6 membered heterocycloalkyl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently phenyl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently 5-6 membered heteroaryl optionally substituted with D, halogen, —CN, —OH, —NH$_2$, oxo, —NR$^{c1}$R$^{d1}$, —OR$^{a1}$, —SR$^{a1}$, $C_1$-$C_6$ alkyl, $C_1$-$C_6$ haloalkyl.

In some embodiments, each $R^{2A}$ is independently —NR$^c$R$^d$. In some embodiments, each $R^{2A}$ is independently —OR$^a$. In some embodiments, each $R^{2A}$ is independently —SR$^a$.

In some embodiments, each $R^{2A}$ is independently —C(O) R$^b$. In some embodiments, each $R^{2A}$ is independently —C(O)NR$^c$R$^d$. In some embodiments, each $R^{2A}$ is independently —C(O)OR$^a$. In some embodiments, each $R^{2A}$ is independently —OC(O)R$^b$. In some embodiments, each $R^{2A}$ is independently —OC(O)NR$^c$R$^d$.

In some embodiments, each $R^{2A}$ is independently —NR$^c$C(O)R$^b$. In some embodiments, each $R^{2A}$ is independently —NR$^c$C(O)NR$^c$R$^d$. In some embodiments, each $R^{2A}$ is independently —NR$^c$C(O)OR$^a$.

In some embodiments, each $R^{2A}$ is independently —S(O) (=NR$^b$)R$^b$. In some embodiments, each $R^{2A}$ is independently —S(O)R$^b$. In some embodiments, each $R^{2A}$ is independently —S(O)NR$^c$R$^d$. In some embodiments, each $R^{2A}$ is independently —S(O)$_2$R$^b$. In some embodiments, each $R^{2A}$ is independently —NR$^c$S(O)$_2$R$^d$. In some embodiments, each $R^{2A}$ is independently —S(O)$_2$NR$^c$R$^d$. In some embodiments, each $R^{2A}$ is independently —NR$^c$S(O)$_2$NR$^c$R$^d$. In some embodiments, each $R^{2A}$ is independently —NR$^c$S(O) (=NR$^b$)R$^b$.

In some embodiments, $R^3$ is $C_1$-$C_{10}$ alkyl, $C_2$-$C_{10}$ alkenyl, $C_2$-$C_{10}$ alkynyl, $C_3$-$C_{14}$ cycloalkyl, 4-14 membered heterocycloalkyl, $C_6$-$C_{10}$ aryl, 5-14 membered heteroaryl; wherein the $C_1$-$C_{10}$ alkyl, $C_2$-$C_{10}$ alkenyl, $C_2$-$C_{10}$ alkynyl, $C_3$-$C_{14}$ cycloalkyl, 4-14 membered heterocycloalkyl, $C_6$-$C_{10}$ aryl, 5-14 membered heteroaryl is optionally substituted by 1, 2, 3, 4 or 5 substituent(s) independently selected from $R^4$.

In some embodiments, $R^3$ is $C_1$-$C_{10}$ alkyl optionally substituted by 1, 2, 3, 4 or 5 substituent(s) independently selected from $R^4$. In some embodiments, $R^3$ is $C_1$-$C_8$ alkyl optionally substituted by 1, 2, 3, 4 or 5 substituent(s) independently selected from $R^4$. In some embodiments, $R^3$ is $C_1$-$C_6$ alkyl optionally substituted by 1, 2, 3, 4 or 5 substituent(s) independently selected from $R^4$.

In some embodiments, $R^3$ is $C_2$-$C_{10}$ alkenyl optionally substituted by 1, 2, 3, 4 or 5 substituent(s) independently selected from $R^4$.

In some embodiments, $R^3$ is $C_2$-$C_{10}$ alkynyl optionally substituted by 1, 2, 3, 4 or 5 substituent(s) independently selected from $R^4$.

In some embodiments, $R^3$ is $C_3$-$C_{14}$ cycloalkyl optionally substituted by 1, 2, 3, 4 or 5 substituent(s) independently selected from $R^4$.

In some embodiments, $R^3$ is 4-14 membered heterocycloalkyl optionally substituted by 1, 2, 3, 4 or 5 substituent(s) independently selected from $R^4$.

In some embodiments, $R^3$ is $C_6$-$C_{14}$ aryl optionally substituted by 1, 2, 3, 4 or 5 substituent(s) independently selected from $R^4$. In some embodiments, $R^3$ is phenyl, naphthalenyl, anthracenyl, phenanthrenyl; each is optionally substituted by 1, 2, 3, 4 or 5 substituent(s) selected from $R^4$.

In some embodiments, $R^3$ is 5-14 membered heteroaryl optionally substituted by 1, 2, 3, 4 or 5 substituent(s) independently selected from $R^4$.

In some embodiments, $R^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$F, —CH$_2$CHF$_2$, —CH$_2$CF$_3$, —CF$_2$CH$_3$, —CH$_2$CH$_2$OH, —CH$_2$CH$_2$CH$_2$OH, —CH$_2$CH(OH)CH$_3$, —CH$_2$CH(OH) CH$_2$CH$_3$, —CH$_2$CH$_2$CH(CH$_3$)OH, —CH$_2$CH$_2$C(CH$_3$)$_2$OH, —CH$_2$CH$_2$CH$_2$CH$_2$OH, —CH$_2$CH$_2$OCH$_3$, —CH$_2$CH$_2$CH$_2$OCH$_3$, —CH$_2$CH$_2$CH$_2$CH$_2$OCH$_3$, —CH$_2$COOH, —CH$_2$CN, —CH$_2$CH$_2$CN, In some embodiments, each $R^4$ is independently H, D, halo, —CN, —NO$_2$, —N$_3$, oxo. In some embodiments, each $R^4$ is independently H. In some embodiments, each $R^4$ is independently D. In some embodiments, each $R^4$ is independently halo (such as —F, —Cl, —Br or —I). In some embodiments, each $R^4$ is independently —CN. In some embodiments, each $R^4$ is independently —NO$_2$. In some embodiments, each $R^4$ is independently —N$_3$.

In some embodiments, one of $R^4$ is —NR$^C$R$^D$. In some embodiments, one of $R^4$ is —NH$_2$, —NHCH$_3$, —N(CH$_3$)$_2$, —NHCH$_2$CH$_3$, —N(CH$_2$CH$_3$)$_2$.

In some embodiments, one of $R^4$ is —OR$^4$. In some embodiments, one of $R^4$ is —OH, —OCH$_3$, —OCH$_2$CH$_3$, —OCH$_2$CH$_2$CH$_3$, —OCH(CH$_3$)$_2$, —OCH$_2$F, —OCHF$_2$, —OCF$_3$, —OCH$_2$CH$_2$F, —OCH$_2$CHF$_2$, —OCH$_2$CF$_3$, —OCF$_2$CF$_3$, —OCH$_2$CH$_2$OH, —OCH$_2$CH$_2$OCH$_3$, —OTBS, —OTMS,

33

In some embodiments, one of $R^4$ is —$SR^A$. In some embodiments, one of $R^4$ is —$NR^C OR^A$.

In some embodiments, one of $R^4$ is $C(O)R^B$. In some embodiments, one of $R^4$ is —$C(O)CH_3$, —$C(O)CH_2CH_3$, —$C(O)CH_2CH_2CH_3$, —$C(O)CH(CH_3)_2$,

34

-continued each ring is optionally substituted with 1, 2, 3, 4 or 5 substituent(s) independently selected from D, —CN, halo, oxo, $C_1$-$C_4$ alkyl, $C_1$-$C_4$haloalkyl, $C_1$-$C_4$ cyanoalkyl, $C_1$-$C_4$ alkyl-O—$C_1$-$C_4$ alkyl, $C_1$-$C_4$ alkyl-O—$C_1$-$C_4$ haloalkyl, —$SF_5$, —$OR^a$, —$C(O)R^b$, —$OC(O)NR^C R^d$, —$NR^C R^d$, —$NR^C C(O)R^b$, —$NR^C C(O)NR^C R^d$, —$NR^C C(O)OR^a$, —$S(O)R^b$, —$S(O)NR^C R^d$, —$S(O)_2R^b$, —$NR^C S(O)_2R^b$, —$S(O)_2NR^C R^d$, —$NR^C S(O)_2NR^C R^d$, or —$B(OR^c)(OR^d)$.

In some embodiments, one of $R^4$ is —$C(O)NR^C R^D$. In some embodiments, one of $R^4$ is —$C(O)NH_2$, —$C(O)NHCH_3$, —$C(O)N(CH_3)_2$, In some embodiments, one of $R^4$ is —$C(O)OR^A$. In some embodiments, one of $R^4$ is —$C(O)OH$, —$C(O)OCH_3$, —$C(O)OCH_2CH_3$.

In some embodiments, one of $R^4$ is —$OC(O)R^B$. In some embodiments, one of $R^4$ is —$OC(O)NR^C R^D$.

In some embodiments, one of $R^4$ is —$NR^C C(O)R^B$. In some embodiments, one of $R^4$ is —$NR^C C(O)NR^C R^D$. In some embodiments, one of $R^4$ is —$NR^C C(O)OR^A$.

In some embodiments, one of $R^4$ is —$S(O)R^B$. In some embodiments, one of $R^4$ is —$S(O)_2R^B$.

In some embodiments, one of $R^4$ is —$S(O)NR^C R^D$. In some embodiments, one of $R^4$ is —$NR^C S(O)_2R^D$. In some embodiments, one of $R^4$ is —$S(O)_2NR^C R^D$. In some embodiments, one of $R^4$ is —$NR^C S(O)_2NR^C R^D$. In some embodiments, one of $R^4$ is —$NR^C S(O)(=NR^B)R^B$.

In some embodiments, one of $R^4$ is —$SiR^G R^H R^I$. In some embodiments, one of $R^4$ is —$B(OR^C)(OR^D)$. In some embodiments, one of $R^4$ is —$P(O)R^E R^F$.

In some embodiments, each $R^4$ is independently $C_1$-$C_6$ alkyl optionally substituted with 1, 2, 3, 4, or 5 substituents independently selected from $R^5$. In some embodiments, each $R^4$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$; each is optionally substituted with 1, 2, 3, 4, or 5 substituents independently selected from $R^5$.

In some embodiments, each $R^4$ is independently $C_2$-$C_6$ alkenyl optionally substituted with 1, 2, 3, 4, or 5 substituents independently selected from $R^5$. In some embodiments, each $R^4$ is independently —$CH=CH_2$, —$CH=CHCH_3$, —$CH_2CH=CH_2$; each is optionally substituted with 1, 2, 3, 4, or 5 substituents independently selected from $R^5$.

In some embodiments, each $R^4$ is independently $C_2$-$C_6$ alkynyl optionally substituted with 1, 2, 3, 4, or 5 substituents independently selected from $R^5$. In some embodiments, each $R^4$ is independently —C≡CH, —C≡CCH$_3$; each is optionally substituted with 1, 2, 3, 4, or 5 substituents independently selected from $R^5$.

In some embodiments, each $R^4$ is independently $C_6$-$C_{10}$ aryl optionally substituted with 1, 2, 3, 4, or 5 substituents independently selected from $R^5$. In some embodiments, each $R^4$ is independently phenyl, naphthalenyl; each is optionally substituted with 1, 2, 3, 4, or 5 substituents independently selected from $R^5$.

In some embodiments, each $R^4$ is independently $C_3$-$C_{10}$ cycloalkyl optionally substituted with 1, 2, 3, 4, or 5 substituents independently selected from $R^5$. In some embodiments, one of $R^4$ is independently cyclopropyl, cyclobutyl, cyclopentyl, cyclohexyl; each is optionally substituted with 1, 2, 3, 4, or 5 substituents independently selected from $R^5$. In some embodiments, one of $R^4$ is independently cyclopropyl, cyclobutyl, cyclopentyl, cyclohexyl, In some embodiments, each $R^4$ is independently 5-10 membered heteroaryl optionally substituted with 1, 2, 3, 4, or 5 substituents independently selected from $R^5$. In some embodiments, one of $R^4$ is pyrrolyl, imidazolyl, oxazolyl, isoxazolyl, thiazolyl, pyrazolyl, 1,2,4-triazolyl, 1,2,3-triazolyl, thiadiazolyl, oxadiazolyl, pyridinyl, pyrimidinyl, pyrazinyl, pyridazinyl, indolyl; each is optionally substituted with 1, 2, 3, 4 or 5 substituents independently selected from $R^5$. In some embodiments, one of $R^4$ is In some embodiments, each $R^4$ is independently 4-10 membered heterocycloalkyl optionally substituted with 1, 2, 3, 4, or 5 substituents independently selected from $R^5$. In some embodiments, one of $R^4$ is azetidinyl, oxetanyl, pyrrolidinyl, tetrahydrofuranyl, tetrahydrothiophenyl, piperidinyl, dioxanyl, tetrahydropyranyl, tetrahydrothiopyranyl, piperazinyl, morpholinyl, azepanyl, diazocanyl, 1,4-diazepanyl; each is optionally substituted with 1, 2, 3, 4, or 5 substituents independently selected from $R^5$. In some embodiments, one of $R^4$ is In some embodiments, two $R^4$ together with the atom(s) to which they are attached form oxo.

In some embodiments, two $R^4$ together with the atom(s) to which they are attached form $C_3$-$C_6$ cycloalkyl, 4-6 membered heterocycloalkyl; each ring is optionally substituted with 1, 2, 3, 4 or 5 substituent(s) independently selected from $R^5$.

In some embodiments, two $R^4$ together with the atom(s) to which they are attached form In some embodiments, each $R^5$ is independently D, —CN, halo, —NO$_2$, —SF$_5$, oxo. In some embodiments, each $R^5$ is independently D. In some embodiments, each $R^5$ is independently —CN. In some embodiments, each $R^5$ is independently halo (such as —F, —Cl, —Br or —I). In some embodiments, each $R^5$ is independently —NO$_2$. In some embodiments, each $R^5$ is independently —SF$_5$. In some embodiments, each $R^5$ is independently oxo.

In some embodiments, each $R^5$ is independently optionally substituted $C_1$-$C_6$ alkyl.

In some embodiments, each $R^5$ is independently optionally substituted $C_2$-$C_6$ alkenyl.

In some embodiments, each $R^5$ is independently optionally substituted $C_2$-$C_6$ alkynyl.

In some embodiments, each $R^5$ is independently optionally substituted $C_3$-$C_6$ cycloalkyl.

In some embodiments, each $R^5$ is independently optionally substituted 4-6 membered heterocycloalkyl.

In some embodiments, each $R^5$ is independently —OR$^a$. In some embodiments, each $R^5$ is independently —SR$^a$.

In some embodiments, each $R^5$ is independently —C(O)R$^b$. In some embodiments, each $R^5$ is independently —C(O)NR$^c$R$^d$. In some embodiments, each $R^5$ is independently —C(O)OR$^a$. In some embodiments, each $R^5$ is independently —OC(O)R$^b$. In some embodiments, each $R^5$ is independently —OC(O)NR$^c$R$^d$.

In some embodiments, each $R^5$ is independently —NR$^c$R$^d$. In some embodiments, one of $R^5$ is —NH$_2$, —NH(CH$_3$), or —N(CH$_3$)$_2$. In some embodiments, each $R^5$ is independently —NR$^c$C(O)R$^b$. In some embodiments, each $R^5$ is independently —NR$^c$C(O)NR$^c$R$^d$. In some embodiments, each $R^5$ is independently —NR$^c$C(O)OR$^a$.

In some embodiments, each $R^5$ is independently —S(O)(=NR$^b$)R$^b$. In some embodiments, each $R^5$ is independently —S(O)R$^b$. In some embodiments, each $R^5$ is independently —S(O)NR$^c$R$^d$. In some embodiments, each $R^5$ is independently —S(O)$_2$R$^b$. In some embodiments, each $R^5$ is independently —NR$^c$S(O)$_2$R$^d$. In some embodiments, each $R^5$ is independently —S(O)$_2$NR$^c$R$^d$. In some embodiments, each $R^5$ is independently —NR$^c$S(O)$_2$NR$^c$R$^d$. In some embodiments, each $R^5$ is independently —NR$^c$S(O)(=NR$^b$)R$^b$.

In some embodiments, each $R^4$ is independently H. In some embodiments, each $R^4$ is independently D.

In some embodiments, each $R^4$ is independently $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocyclalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, $C_1$-$C_4$ alkyl, $C_1$-$C_4$ haloalkyl, $C_1$-$C_4$ alkyl-OH, $C_1$-$C_4$ alkyl-CN, $C_1$-$C_4$ alkyl-O—$C_1$-$C_4$ alkyl, $C_1$-$C_4$ alkyl-O—$C_1$-$C_4$ haloalkyl, —$NO_2$, oxo, —$OR^a$, —$SR^a$, —$SF_5$, —$NHOR^a$, —C(O)$R^b$, —C(O)$NR^cR^d$, —C(O)$OR^a$, —OC(O)$R^b$, —OC(O)$NR^cR^d$, —$NR^cR^d$, —$NR^cC(O)R^b$, —$NR^cC(O)NR^cR^d$, —$NR^cC(O)OR^a$, —B(O$R^c$)(O$R^d$), —C(=$NR^c$)$NR^cR^d$, —$NR^dC$(=$NR^c$)$NR^cR^d$, —$NR^dC$(=$NR^c$)$R^b$, —P(O)$R^eR^f$, —P(O)O$R^e$O$R^f$, —OP(O)O$R^e$-O$R^f$, —S(O)$R^b$, —S(O)$NR^cR^d$, —S(O)$_2R^b$, —$NR^cS(O)_2R^b$, —S(O)$_2NR^cR^d$, —$NR^cS(O)_2NR^cR^d$, or —$NR^cS(O)$(=$NR^b$)$R^b$.

In some embodiments, one of $R^A$ is —Si$R^GR^HR^I$. In some embodiments, one of $R^A$ is -TMS, In some embodiments, each $R^B$ is independently H. In some embodiments, each $R^B$ is independently D.

In some embodiments, each $R^B$ is independently $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, oxo, $C_1$-$C_4$ alkyl, $C_1$-$C_4$haloalkyl, $C_1$-$C_4$ cyanoalkyl, $C_1$-$C_4$ alkyl-O—$C_1$-$C_4$ alkyl, $C_1$-$C_4$ alkyl-O—$C_1$-$C_4$ haloalkyl, —$SF_5$, —$OR^a$, —C(O)$R^b$, —OC(O)$NR^cR^d$, —$NR^cR^d$, —$NR^cC(O)R^b$, —$NR^cC(O)NR^cR^d$, —$NR^cC(O)OR^a$, —S(O)$R^b$, —S(O)$NR^cR^d$, —S(O)$_2R^b$, —$NR^cS(O)_2R^b$, —S(O)$_2NR^cR^d$, $NR^cS(O)_2NR^cR^d$, or —B(O$R^c$)(O$R^d$).

In some embodiments, $R^C$ and $R^D$ are each independently selected from H. In some embodiments, $R^C$ and $R^D$ are each independently selected from D.

In some embodiments, $R^C$ and $R^D$ are each independently selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, oxo, $C_1$-$C_4$ alkyl, $C_1$-$C_4$haloalkyl, $C_1$-$C_4$ cyanoalkyl, $C_1$-$C_4$ alkyl-O—$C_1$-$C_4$ alkyl, $C_1$-$C_4$ alkyl-O—$C_1$-$C_4$ haloalkyl, —$SF_5$, —$OR^a$, —OC(O)$NR^cR^d$, —$NR^cR^d$, —$NR^cC(O)R^b$, —S(O)$NR^cR^d$, S(O)$_2R^b$, —$NR^cS(O)_2R^b$, —S(O)$_2NR^cR^d$, —$NR^cS(O)_2$ $NR^cR^d$, or —B(O$R^c$)(O$R^d$).

In some embodiments, $R^C$ and $R^D$ together with the N atom to which they are attached form a 4-7 membered heterocycloalkyl optionally substituted with 1, 2, 3, 4 or 5 substituent(s) independently selected from D, —OH, oxo, —CN, —$NH_2$, —NH($C_1$-$C_4$ alkyl), —N($C_1$-$C_4$ alkyl)$_2$, halo, $C_1$-$C_4$ alkyl, $C_1$-$C_4$haloalkyl, $C_1$-$C_4$ cyanoalkyl, —O$C_1$-$C_4$ alkyl, or —O$C_1$-$C_4$haloalkyl.

In some embodiments, each $R^a$ is independently H. In some embodiments, each $R^a$ is independently D.

In some embodiments, each $R^a$ is independently $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, halo, —OH, —CN, —$NH_2$, —NH($C_1$-$C_4$ alkyl), —N($C_1$-$C_4$ alkyl)$_2$, $C_1$-$C_4$ alkyl, —O$C_1$-$C_4$ alkyl, $C_1$-$C_4$haloalkyl, or —O$C_1$-$C_4$haloalkyl.

In some embodiments, each $R^{a1}$ is independently H. In some embodiments, each $R^{a1}$ is independently D.

In some embodiments, each $R^{a1}$ is independently $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, halo, —OH, —CN, —$NH_2$, —NH($C_1$-$C_4$ alkyl), —N($C_1$-$C_4$ alkyl)$_2$, $C_1$-$C_4$ alkyl, —O$C_1$-$C_4$ alkyl, $C_1$-$C_4$haloalkyl, or —O$C_1$-$C_4$haloalkyl.

In some embodiments, each $R^b$ is each independently selected from H. In some embodiments, each $R^b$ is each independently selected from D.

In some embodiments, each $R^b$ is each independently selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —OH, —CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl.

In some embodiments, each $R^{b1}$ is each independently selected from H. In some embodiments, each $R^{b1}$ is each independently selected from D.

In some embodiments, each $R^{b1}$ is each independently selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl.

In some embodiments, $R^c$ and $R^d$ are each independently selected from H. In some embodiments, $R^c$ and $R^d$ are each independently selected from D.

In some embodiments, $R^c$ and $R^d$ are each independently selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl); wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl) is optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, —C(O)OR$^{a1}$, —C(O)R$^{b1}$, —S(O)$_2$R$^{b1}$, $C_1$-$C_4$ alkyl-O—$C_1$-$C_4$ alkyl, and $C_1$-$C_4$ alkyl-O—$C_1$-$C_4$ alkyl-O—.

In some embodiments, $R^c$ and $R^d$ together with the N atom to which they are attached form a 4-7 membered heterocycloalkyl optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl, or $C_1$-$C_4$ alkoxy-$C_1$-$C_4$ alkoxy.

In some embodiments, $R^{c1}$ and $R^{d1}$ are each independently selected from H. In some embodiments, $R^{c1}$ and $R^{d1}$ are each independently selected from D.

In some embodiments, $R^{c1}$ and $R^{d1}$ are each independently selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl); wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl) is optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)OR$^{a1}$, C(O)R$^{b1}$, S(O)$_2$R$^{b1}$, $C_1$-$C_4$ alkyl-O—$C_1$-$C_4$ alkyl, and $C_1$-$C_4$ alkyl-O—$C_1$-$C_4$ alkyl-O—.

In some embodiments, $R^{c1}$ and $R^{d1}$ together with the N atom to which they are attached form a 4-7 membered heterocycloalkyl optionally substituted with 1, 2, 3, 4 or 5 substituent(s) independently selected from D, —OH, —CN, —NH$_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl, or $C_1$-$C_4$ alkoxy-$C_1$-$C_4$ alkoxy.

In some embodiments, each $R^E$ is independently H, D.

In some embodiments, each $R^E$ is independently $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl.

In some embodiments, each $R^F$ is independently H, D.

In some embodiments, each $R^F$ is independently $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl.

In some embodiments, each $R^e$ is independently H, D.

In some embodiments, each $R^e$ is independently $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl.

In some embodiments, each $R^f$ is independently H, D.

In some embodiments, each $R^f$ is independently $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl.

In some embodiments, $R^G$, $R^H$ and $R^I$ are each independently selected from optionally substituted $C_1$-$C_4$ alkyl or optionally substituted phenyl.

In some embodiments, $R^G$ is optionally substituted $C_1$-$C_4$ alkyl (such as $C_1$ alkyl, $C_2$ alkyl, $C_3$ alkyl, $C_4$ alkyl) or phenyl. In some embodiments, $R^G$ is methyl, ethyl, propyl (such as n-propyl, i-propyl), butyl (n-butyl, i-butyl, t-butyl) or phenyl.

In some embodiments, $R^H$ is optionally substituted $C_1$-$C_4$ alkyl (such as $C_1$ alkyl, $C_2$ alkyl, $C_3$ alkyl, $C_4$ alkyl) or phenyl. In some embodiments, $R^H$ is methyl, ethyl, propyl (such as n-propyl, i-propyl), or butyl (n-butyl, i-butyl, t-butyl) or phenyl.

In some embodiments, $R^I$ is optionally substituted $C_1$-$C_4$ alkyl (such as $C_1$ alkyl, $C_2$ alkyl, $C_3$ alkyl, $C_4$ alkyl) or phenyl. In some embodiments, $R^I$ is methyl, ethyl, propyl (such as n-propyl, i-propyl), or butyl (n-butyl, i-butyl, t-butyl) or phenyl.

In some embodiments, the compound of Formula (I) is represented by compounds of Formula (IIa), (IIb) or (IIc):

(IIa)

(IIb)

(IIc)

or a pharmaceutically acceptable salt, solvate, tautomer, stereoisomer, atropisomer, isotopic variant, prodrug or deuterated compound thereof, $X^1$, $X^2$, $X^3$, $X^4$ are each independently selected from N or $CR^2$;

wherein, $R^1$, $R^2$, $R^3$ and m are defined with respect to Formula (I).

In some embodiments, the compound of Formula (I) is represented by compounds of Formula (IIIa), (IIb), (IIc), (IIId), (IIIe), (IIIf) or (IIIg):

(IIIa)

(IIIb)

(IIIc)

(IIId)

(IIIe)

(IIIf)

(IIIg)

or a pharmaceutically acceptable salt, solvate, tautomer, stereoisomer, atropisomer, isotopic variant, prodrug or deuterated compound thereof, wherein, $R^1$, $R^2$, $R^3$ and m are defined with respect to Formula (I).

In some embodiments, the compound of Formula (I) is represented by compounds of Formula (IVa), (IVb), (IVc), (IVd), (IVe), (IVf) or (IVg):

(IVa)

(IVb)

(IVc)

(IVd)

(IVe)

-continued (IVf)

(IVg)

or a pharmaceutically acceptable salt, solvate, tautomer, stereoisomer, atropisomer, isotopic variant, prodrug or deuterated compound thereof, $Y^3$ is N or $CR^1$;

wherein, $R^1$, $R^2$, $R^3$ and m are defined with respect to Formula (I).

In some embodiments, the compound of Formula (I) is:

45

46

47

-continued

48

-continued

49

-continued

50

-continued

51

-continued or a pharmaceutically acceptable salt thereof.

The present disclosure further provides a pharmaceutical composition comprising the compound of Formula (I), or pharmaceutically acceptable salt thereof and at least one pharmaceutically acceptable excipient.

The present disclosure also provides a method for treating and/or preventing a cancer characterized by overexpression of PolQ in a patient comprising administering to the patient a therapeutically effective amount of the compound of the present disclosure, or a pharmaceutical composition comprising the compound disclosed herein.

The present disclosure also provides a method of treating and/or preventing of a cancer in a patient, wherein the cancer is characterized by increased dependence upon MMEJ DSB repair, comprising administering to the patient a therapeutically effective amount of the compound of the present disclosure, or a pharmaceutical composition comprising the compound disclosed herein.

The present disclosure also provides a method of treating and/or preventing of a cancer in a patient, wherein the cancer is characterized by HR-deficiency, a reduction or absence of expression of HR-associated genes, comprising administering to the patient a therapeutically effective amount of the compound of the present disclosure, or a pharmaceutical composition comprising the compound disclosed herein.

The present disclosure also provides a method of treating and/or preventing of a cancer that is lack of 53BP1/Shieldin complex in a patient, comprising administering to the patient a therapeutically effective amount of the compound of the present disclosure, or a pharmaceutical composition comprising the compound disclosed herein.

The present disclosure also provides a method of treating and/or preventing of a cancer, following or not following exposure to PARPi medication, which are resistant to PARPi treatment, comprising administering to the patient a therapeutically effective amount of the compound of the present disclosure, or a pharmaceutical composition comprising the compound disclosed herein.

The present disclosure also provides a method of treating and/or preventing of a cancer in a patient, wherein the cancer is characterized by NHEJ deficiency, a reduction or absence of expression of NHEJ-associated genes, comprising administering to the patient a therapeutically effective amount of the compound of the present disclosure, or a pharmaceutical composition comprising the compound disclosed herein.

The present invention also provides use of the compound or the pharmaceutical composition of the present disclosure in the manufacture of a medicament for treating a disease characterized by overexpression of PolQ in a patient.

The present invention also provides use of the compound or the pharmaceutical composition of the present disclosure in the manufacture of a medicament for treating a disease in a patient, wherein the disease is characterized by increased dependence upon MIMEJ DSB repair.

The present invention also provides use of the compound or the pharmaceutical composition of the present disclosure in the manufacture of a medicament for treating a cancer in a patient, wherein the cancer is characterized by HR-deficiency, a reduction or absence of expression of HR-associated genes.

The present invention also provides use of the compound or the pharmaceutical composition of the present disclosure in the manufacture of a medicament for treating a cancer in a patient that is lack of 53BP1/Shieldin complex.

The present invention also provides use of the compound or the pharmaceutical composition of the present disclosure in the manufacture of a medicament for treating a cancer in a patient, wherein the cancer, following or not following exposure to PARPi medication, which are resistant to PARPi treatment.

The present invention also provides use of the compound or the pharmaceutical composition of the present disclosure in the manufacture of a medicament for treating a cancer in a patient, wherein the cancer is characterized by NHEJ deficiency, a reduction or absence of expression of NHEJ-associated genes.

Definitions

Unless other indicated, the following terms are intended to have the meaning set forth below. Other terms are defined elsewhere throughout the specification.

As used herein, the singular forms "a", "an", and "the" include plural referents unless the context clearly dictates otherwise. It is further noted that the claims may be drafted to exclude any optional element. As such, this statement is intended to serve as antecedent basis for use of such exclusive terminology such as "solely", "only" and the like in connection with the recitation of claim elements, or use of a "negative" limitation.

At various places in the present specification, variables defining divalent linking groups are described. It is specifically intended that each linking substituent include both the forward and backward forms of the linking substituent. For example, —NR(CR'R")— includes both —NR(CR'R")— and —(CR'R")NR— and is intended to disclose each of the forms individually. Where the structure requires a linking group, the Markush variables listed for that group are understood to be linking groups. For example, if the structure requires a linking group and the Markush group definition for that variable list "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "Cn-Cm" indicates a range which includes the endpoints, wherein n and m are integers and indicate the number of carbons. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. "$C_0$ alkyl" refers to a covalent bond or H.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

As used herein, unless otherwise indicated, the term "alkyl", by itself or as part of another substituent, is meant to refer to a saturated hydrocarbon group which is straight-chained or branched. An alkyl group can contain from 1 to about 20, from 2 to about 20, from 1 to about 10, from 1 to about 8, from 1 to about 6, from 1 to about 4, or from 1 to about 3 carbon atoms. Examples, alkyl can include any number of carbons, such as $C_{1-2}$ alkyl, $C_{1-3}$ alkyl, $C_{1-4}$ alkyl, $C_{1-5}$ alkyl, $C_{1-6}$ alkyl, $C_{1-7}$ alkyl, $C_{1-8}$ alkyl, $C_{1-9}$ alkyl, $C_{1-10}$ alkyl, $C_{2-3}$ alkyl, $C_{2-4}$ alkyl, $C_{2-5}$ alkyl, $C_{2-6}$ alkyl, $C_{3-4}$ alkyl, $C_{3-5}$ alkyl, $C_{3-6}$ alkyl, $C_{4-5}$ alkyl, $C_{4-6}$ alkyl and $C_{5-6}$ alkyl. Similarly, $C_{1-8}$, as in $C_{1-8}$ alkyl is defined to identify the group as having 1, 2, 3, 4, 5, 6, 7 or 8 carbon atoms in a linear or branched arrangement. Exemplary alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), hexyl, heptyl, octyl, and the like.

As used herein, unless otherwise indicated, "alkenyl" refers to an alkyl group having one or more double carbon-carbon bonds. Alkenyl can include any number of carbons, such as $C_{2-3}$ alkenyl, $C_{2-4}$ alkenyl, $C_{2-5}$ alkenyl, $C_{2-6}$ alkenyl, $C_{2-7}$ alkenyl, $C_{2-8}$ alkenyl, $C_{2-9}$ alkenyl, $C_{2-10}$ alkenyl, $C_{3-4}$ alkenyl, $C_{3-5}$ alkenyl, $C_{3-6}$ alkenyl, $C_{4-5}$ alkenyl, $C_{4-6}$ alkenyl and $C_{5-6}$ alkenyl. Exemplary alkenyl groups include, but are not limited to, ethenyl, propenyl, butenyl, pentenyl, hexenyl, and the like. The one or more carbon-carbon double bonds can be internal (such as in 2-butene) or terminal (such as in 1-butene).

As used herein, unless otherwise indicated, "alkynyl" refers to an alkyl group having one or more triple carbon-carbon bonds. Alkynyl can include any number of carbons, such as $C_{2-3}$ alkynyl, $C_{2-4}$ alkynyl, $C_{2-5}$ alkynyl, $C_{2-6}$ alkynyl, $C_{2-7}$ alkynyl, $C_{2-8}$ alkynyl, $C_{2-9}$ alkynyl, $C_{2-10}$ alkynyl, $C_{3-4}$ alkynyl, $C_{3-5}$ alkynyl, $C_{3-6}$ alkynyl, $C_{4-5}$ alkynyl, $C_{4-6}$ alkynyl and $C_{5-6}$ alkynyl. Exemplary alkynyl groups include, but are not limited to, ethynyl, propynyl, butynyl, pentynyl, and the like. The one or more carbon-carbon triple bonds can be internal (such as in 2-butyne) or terminal (such as in 1-butyne).

As used herein, unless otherwise indicated, "haloalkyl" refers to an alkyl group having one or more halogen substituents. Exemplary haloalkyl groups include, but are not limited to, $-CF_3$, $-C_2F_5$, $-CHF_2$, $-CH_2F$, $-CCl_3$, $-CHCl_2$, $-C_2Cl_5$, and the like.

As used herein, unless otherwise indicated, "aryl" refers to an unsubstituted or substituted monocyclic or polycyclic (e.g., having 2, 3 or 4 fused rings) aromatic hydrocarbons. In some embodiments, aryl groups have from 6 to about 20 carbon atoms. In some embodiments, aryl groups have from 6 to about 14 carbon atoms. In some embodiments, aryl groups have from 6 to about 10 carbon atoms. Exemplary aryl groups include, but are not limited to, phenyl, naphthyl, anthracenyl, phenanthrenyl, indanyl, indenyl, and the like.

As used herein, unless otherwise indicated, "cycloalkyl" refers to an unsubstituted or substituted non-aromatic carbocycles including cyclized alkyl, alkenyl, and alkynyl groups. Cycloalkyl groups can include mono- or polycyclic (e.g., having 2, 3 or 4 fused rings) ring systems, including fused rings, spirocyclic rings, and bridged rings (e.g., a bridged bicycloalkyl group). In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Cycloalkyl groups can be optionally substituted by oxo or sulfido (e.g., $-C(O)-$ or $-C(S)-$). Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. In some embodiments, the cycloalkyl is a $C_3$-$C_7$ monocyclic cycloalkyl. In some embodiments, the cycloalkyl is a $C_4$-$C_{10}$ spirocycle or bridged cycloalkyl. Exemplary cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl. In some embodiments, cycloalkyl are cyclic-containing, non-aromatic hydrocarbon groups having from 3 to 12 carbon atoms ("$C_3$-$C_{12}$"), preferably from 3 to 6 carbon atoms ("$C_3$-$C_6$"). Examples of cycloalkyl groups include, for example, cyclopropyl ($C_3$; 3-membered), cyclobutyl ($C_4$; 4-membered), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "spirocycloalkyl" when used alone or as part of a substituent group refers to a non-aromatic hydrocarbon group containing two cycloalkyl rings, and wherein the two cycloalyl rings share a single carbon atom in common.

As used herein, unless otherwise indicated, a "heteroaryl" group refers to an unsubstituted or substituted aromatic heterocycle having at least one heteroatom ring member such as boron, sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, unless otherwise indicated, "heterocycloalkyl" refers to an unsubstituted or substituted monocyclic (saturated or partially unsaturated ring) or polycyclic heterocycles having at least one non-aromatic ring (saturated or partially unsaturated ring), wherein one or more of the ring-forming carbon atoms of the heterocycloalkyl is replaced by a heteroatom selected from N, O, S, Si and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 3-10, 4-10, 3-7, 4-7, and 5-6 membered heterocycloalkyl groups. Heterocycloalkyl groups can also include spirocycles and bridged rings (e.g., a 5-10 membered bridged biheterocloalkyl ring having one or more of the ring-forming carbon atoms replaced by a heteroatom independently selected from N, O, S, Si and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Exemplary heterocycloalkyl groups include, but are not limited to, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, diazabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, oxaazaspiro[3.5]nonanyl, azaspiro[2.5]octanyl, diazaspiro[2.5]octanyl, azaspiro[4.4]nonanyl, diazaspiro[4.4]nonanyl, oxaazaspiro[4.4]nonanyl, azaspiro[4.5]decanyl, diazaspiro[4.5]decanyl, diazaspiro[4.4]nonanyl, oxa-diazaspiro[4.4]nonanyl, octahydropyrrolo[3,4-c]pyrrolyl and the like.

In some embodiments, heterocycloalkyl refers to any three to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

In some embodiments, the term "spiroheterocycloalkyl" when used alone or as part of a substituent group refers to a non-aromatic group containing two rings, at least one of which is a heterocycloalkyl ring, and wherein the two rings share a single carbon atom in common.

As used herein, "halo" or "halogen" includes fluoro, chloro, bromo, and iodo.

As used herein, unless otherwise indicated, "alkoxy" refers to an —O-alkyl group.

Exemplary alkoxy groups include methoxy, ethoxy, propoxy (e.g., n-propoxy and isopropoxy), t-butoxy, and the like.

As used herein, unless otherwise indicated, "hydroxylalkyl" refers to an alkyl group substituted by OH.

As used herein, unless otherwise indicated, "cyanoalkyl" refers to an alkyl group substituted by CN.

As used herein, unless otherwise indicated, "alkoxyalkyl" refers to an alkyl group substituted by an alkoxy group.

As used herein, unless otherwise indicated, "haloalkoxy" refers to an —O-(haloalkyl) group.

As used herein, unless otherwise indicated, "arylalkylene" refers to alkyl substituted by aryl and "cycloalkylalkylene" refers to alkyl substituted by cycloalkyl. An exemplary arylalkyl enegroup is benzyl.

As used herein, unless otherwise indicated, "heteroarylalkylene" refers to alkyl substituted by heteroaryl and "heterocycloalkylalkylene" refers to alkyl substituted by heterocycloalkyl.

As used herein, unless otherwise indicated, "oxo" refers to an oxygen substituent that is connected by a double bond (i.e., =O).

As used herein, unless otherwise indicated, the phrase "optionally substituted" means unsubstituted or substituted.

As used herein, unless otherwise indicated, the term "substituted" refers to a group in which one or more hydrogen atoms are each independently replaced with the same or different substituent(s).

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. Furthermore, atropisomers and mixtures thereof such as those resulting from restricted rotation about two aromatic or heteroaromatic rings bonded to one another are intended to be encompassed within the scope of the invention. For example, when Cy is a phenyl group and is substituted with two groups bonded to the C atoms adjacent to the point of attachment to the C atom of the pyridine, then rotation of the phenyl may be restricted. In some instances, the barrier of rotation is high enough that the different atropisomers may be separated and isolated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole; certain hydroxy substituted compounds may exist as tautomers as shown below:

etc. Tautomeric forms can be in equilibrium or sterically locked into one form by appropriate substitution.

In some cases, the compounds of the present disclosure may exist as rotational isomers. Descriptions of a compound of the invention that do not indicate a particular rotational isomer are intended to encompass any individual rotational isomers, as well as mixtures of rotational isomers in any proportion. Depiction of a particular rotational isomer is meant to refer to the depicted rotational isomer, substantially free of other rotational isomers.

Compounds of the invention can also include all isotopes of atoms occurring in the intermediates or final compounds. Isotopes include those atoms having the same atomic number but different mass numbers. For example, isotopes of hydrogen include tritium and deuterium.

As used herein, unless otherwise indicated, the phrase "optionally substituted" means unsubstituted or substituted.

As used herein, unless otherwise indicated, the term "substituted" refers to a group in which one or more hydrogen atoms are each independently replaced with the same or different substituent(s). Typical substituents include, but are not limited to, D, halo, oxo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl-$NR^cR^d$, —$(CH_2CH_2O)_oC_1$-$C_6$alkyl wherein o is 1-10; $C_{2-6}$ alkenyl-$NR^cR^d$, $C_{2-6}$ alkynyl-$NR^cR^d$, —$OC_{2-6}$ alkyl-$NR^cR^d$, —CN, —$NO_2$, —$N_3$, —$OR^a$, —$SR^a$, —$C(O)R^b$, —$C(O)NR^cR^d$, —$CH_2C(O)NR^cR^d$, —$C(O)OR^a$, —$OC(O)R^b$, —$OC(O)$$NR^cR^d$, —$NR^cR^d$, —$NR^cC(O)R^b$, —$NR^cC(O)NR^cR^d$, —$NR^cC(O)OR^a$, —$C(=NR^c)NR^cR^d$, —$NR^cC(=NR^c)$$NR^cR^d$, —$P(R^f)_2$, —$P(OR^e)_2$, —$P(O)R^eR^f$, —$P(O)OR^eOR^f$, —$S(O)R^b$, —$SO(=NR)$; —$S(O)NR^cR^d$, —$S(O)_2R^b$, —$NR^cS(O)_2R^b$, —$S(O)_2NR^cR^d$; aryl, heteroaryl, spirocycloalkyl, spiroheterocycloalkyl, cycloalkyl, or heterocycloalkyl, wherein the aryl, heteroaryl, spirocycloalkyl, spiroheterocycloalkyl, cycloalkyl, or heterocycloalkyl are optionally substituted with D, halo, oxo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl-$NR^cR^d$, $C_{2-6}$ alkenyl-$NR^cR^d$, $C_{2-6}$ alkynyl-$NR^cR^d$, $OC_{2-6}$ alkyl-$NR^cR^d$, —CN, —$NO_2$, —$N_3$, —$OR^a$, —$SR^a$, —$C(O)$$R^b$, —$C(O)NR^cR^d$, —$CH_2C(O)NR^cR^d$, —$C(O)OR^a$, —$OC$$(O)R^b$, —$OC(O)NR^cR^d$, —$NR^cR^d$, —$NR^cC(O)R^b$, —$NR^cC$$(O)NR^cR^d$, —$NR^cC(O)OR^a$, —$C(=NR^c)NR^cR^d$, —$NR^cC$$(=NR^c)NR^cR^d$, —$P(R)_2$, —$P(OR^e)_2$, —$P(O)R^eR^f$, —$P(O)$$OR^eOR^f$, —$S(O)R^b$, —$S(O)NR^cR^d$, —$S(O)_2R^b$, —$NR^c$$S(O)_2R^b$, —$S(O)_2NR^cR^d$.

In some embodiments, the compounds of the invention, and salts thereof, are substantially isolated. By "substantially isolated" is meant that the compound is at least partially or substantially separated from the environment in which was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceu-*

59

*tical Sciences,* 17*th* ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure" and equivalent expressions, are meant to embrace compounds of Formula (I) as described herein, as well as its subgenera, which expression includes the stereoisomers (e.g., enantiomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

Pharmaceutical Compositions

The pharmaceutical compositions of the present invention comprise a compound represented by Formula (I) (or a pharmaceutically acceptable salt thereof) as an active ingredient, and pharmaceutically acceptable excipients.

The compositions may be in a form suitable for oral use (for example as tablets, lozenges, hard or soft capsules, aqueous or oily suspensions, emulsions, dispersible powders or granules, syrups or elixirs), for injection use (for example as aqueous or oil suspensions, or emulsions, with sesame oil, corn oil, cottonseed oil, or peanut oil, as well as elixirs, mannitol, dextrose, or a sterile aqueous solution, and similar pharmaceutical vehicles), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions.

The pharmaceutical carrier employed can be, for example, a solid, liquid, or gas. Examples of solid carriers include such as lactose, terra alba, sucrose, talc, gelatin, agar, pectin, acacia, magnesium stearate, and stearic acid. Examples of liquid carriers include such as sugar syrup, peanut oil, olive oil, and water. Examples of gaseous carriers include such as carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, e.g., lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g., swellable crosslinked polymers such as crosslinked carboxymethylcellulose), lubricating agents (e.g., stearates), preservatives (e.g., parabens), antioxidants (e.g., BHT), buffering agents (for example phosphate or citrate buffers), and effervescent agents such as citrate/bicarbonate mixtures. Such excipients are well known and do not need to be discussed in detail here. The table compositions may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropyl cellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

The compositions may be obtained by conventional procedures using conventional pharmaceutical excipients, well known in the art. Thus, compositions intended for oral use may contain, for example, one or more coloring, sweetening, flavoring and/or preservative agents.

An effective amount of a compound of Formula (I) or a pharmaceutically salt thereof for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.1 mg to 1000 mg of Formula (I) or a pharmaceutically salt thereof with an appropriate and convenient amount of excipients which may vary from about 5 to about 98 percent by weight of the total composition.

The size of the dose for therapeutic or prophylactic purposes of a compound of the Formula (I) will naturally vary according to the nature and severity of the conditions, the age and sex of the animal or patient and the route of administration, according to well-known principles of medicine.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, or lung cancer, may be effectively treated by the administration of from about 0.01 to 50 mg of the compound per kilogram of body weight per day, or alternatively about 0.5 mg to about 3.5 g per patient per day.

It is understood, however, that lower or higher doses than those recited above may be required. Specific dose level and treatment regimens for any particular subject will depend upon a variety of factors, including the activity of the specific compound employed, the age, body weight, general health, sex, diet, time of administration, route of administration, rate of excretion, drug combination, the severity and course of the particular disease undergoing therapy, the subject disposition to the disease, and the judgment of the treating physician.

These and other aspects will become apparent from the following written description of the invention.

Described below are non-limiting exemplary pharmaceutical compositions and methods for preparing the same.

Methods of Administration

The compounds of Formula (I) or a pharmaceutically salt thereof or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrastemal; by implant of a depot or reservoir, for example, subcutaneously or intramuscularly.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The subject methods are useful for treating a disease condition associated with PolQ. Any disease condition that results directly or indirectly from an abnormal activity or expression level of PolQ can be an intended disease condition.

Compounds of the present disclosure can be used in the treatment and/or prevention of a disease in a patient, wherein the disease is characterized by overexpression of PolQ.

The term "PolQ overexpression" refers to the increased expression or activity of PolQ enzyme in a diseased cell e.g., cancer cell, relative to expression or activity of PolQ enzyme in a control cell (e.g., non-diseased cell of the same type). The amount of the amount of PolQ overexpression can be at least 2-fold, at least 3-fold, at least 4-fold, at least 5-fold, PolQ overexpression can be at least 2-fold, at least 3-fold, at least 4-fold, at least 5-fold, at least 6-fold, at least 10-fold, at least 20-fold, at least 50-fold, relative to PolQ expression in a control cell. Examples of PolQ overexpressing cancers include, but are not limited to, certain ovarian, breast, cervical, uterine, pancreatic, lung, colorectal, gastric, bladder, and prostate cancers.

Compounds of the present disclosure can be used in the treatment and/or prevention of a disease in a patient, wherein the disease is characterized by increased dependence upon MMEJ DSB repair.

Compounds of the present disclosure can be used in the treatment and/or prevention of a cancer in a patient, wherein the cancer is characterized by HR-deficiency, a reduction or absence of expression of HR-associated genes, including but not limited to, ATM, ATR, BARD1, BLM, BRCA1, BRCA2, BRIP1, CDK12, CHEK1, CHEK2, CtIP (BCL11A), ERCC4 (FANCQ), FANCA, FANCB, FANCC, FANCD2, FANCE, FANCF, FANCG, FANCI, FANJ (BRIP1), FANCL, FANCM, FANCN (PALB2), FANCP (SLX4), LIG1, MRE11, NBS1, NBN, PTEN, RAD50, RAD51B, RAD51C, RAD54, RECQL4, RPA1, RPA2, SMARCA2, SMARCA4, WRN, and XRCC2.

In some embodiments, said method is for use in the treatment or prevention of HR-deficient breast cancer.

In some embodiments, said method is for use in the treatment or prevention of HR-deficient ovarian cancer.

In some embodiments, said method is for use in the treatment or prevention of HR-deficient prostate cancer.

In some embodiments, said method is for use in the treatment or prevention of HR-deficient pancreatic cancer.

Compounds of the present disclosure can be used in the treatment or prevention of a cancer that is lack of 53BP1/ Shieldin complex in a patient.

Compounds of the present disclosure can be used in the treatment or prevention of a cancer, following or not following exposure to PARPi medication, which are resistant to PARPi treatment.

Compounds of the present disclosure can be used in the treatment and/or prevention of a cancer in a patient, wherein the cancer is characterized by NHEJ deficiency, a reduction or absence of expression of NHEJ-associated genes, including but not limited to, 53BP1, DCLRE1C, LIG4, NHEJ1, POLL, POLM, PRKDC, RIF1, SHLD1, SHLD2, SHLD3, XRCC4, XRCC5 and XRCC6.

Compounds of the present disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other methods, compounds of the present disclosure, as well as pharmaceutical compositions comprising them, can be administered to treat any of the described diseases, alone or in combination with one or more other agents.

In other methods, the compounds of the present disclosure, as well as pharmaceutical compositions comprising them, can be administered in combination with agonists of nuclear receptors agents.

In other methods, the compounds of the present disclosure, as well as pharmaceutical compositions comprising them, can be administered in combination with antagonists of nuclear receptors agents.

In other methods, the compounds of the present disclosure, as well as pharmaceutical compositions comprising them, can be administered in combination with an antiproliferative agent.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith el ah, *March's Advanced Organic Chemistry: Reactions, Mechanisms, and Structure*, 8th Ed. (Wiley, 2019); Peturssion et al, Protecting Groups in Carbohydrate Chemistry, *J Chem. Educ.*, 1997, 74(11), 1297; and Wuts et al., *Protective Groups in Organic Synthesis*, 5th Ed., (Wiley, 2014).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature" and "r.t." as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Exemplary synthetic methods for preparing compounds of the invention are provided in the Schemes below.

The following Examples are provided to illustrate some of the concepts described within this disclosure. While the Examples are considered to provide an embodiment, it should not be considered to limit the more general embodiments described herein.

ABBREVIATIONS

| | |
|---|---|
| ADP | Adenosine diphosphate |
| ATP | Adenosine triphosphate |
| BSA | Bovine albumin |
| brine | saturated solution of sodium chloride |
| BOP | (Benzotriazol-1-yloxy)tris(dimethylamino)phosphonium hexafluorophosphate |
| CDI | N,N-Carbonyldiimidazole |
| DCM | Dichloromethane |
| DIEA | N,N-Diisopropylethylamine |
| DMAP | 4-Dimethylaminopyridine |
| DMF | N,N-dimethylformamide |
| DMSO | Dimethylsulfoxide |
| DTT | DL-Dithiothreitol |
| EDCI | N-(3-Dimethylaminopropyl)-N'-ethylcarbodiimide hydrochloride |
| EtOAc | Ethyl acetate |
| EtOH | Ethanol |
| HATU | 2-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate |
| LDA | Lithium diisopropylamide |
| MeCN | Acetonitrile |
| MeOH | Methanol |
| NaHMDS | Sodium bis(trimethylsilyl)amide |
| NMI | N-Methylimidazole |
| Pd(dppf)Cl$_2$ | [1,1'-Bis(diphenylphosphino)ferrocene]dichloropalladium(II) |
| Pd(OAc)$_2$ | Palladium (II) Acetate |
| Pd$_2$(dba)$_3$ | Bis(dibenzylideneacetone)palladium(0) |
| Pd(PPh$_3$)$_4$ | Tetrakis(triphenylphosphine)palladium |
| Pd(PPh$_3$)$_2$Cl$_2$ | Bis(triphenylphosphine)palladium(II) chloride |
| PE | Petroleum ether |
| PyBOP | (benzotriazol-1-yloxy)tripyrrolidinophosphonium hexafluorophosphate |
| T$_3$P | 1-Propanephosphonic anhydride |
| TBAF | Tetrabutylammonium fluoride |
| TCFH | Chloro-N,N,N',N'-tetramethylformamidinium hexafluorophosphate |
| TEA | Triethylamine |
| TFA | Trifluoroacetic acid |
| THF | Tetrahydrofuran |
| aq. | Aqueous |
| r.t. | Room temperature |
| $^1$HNMR | Hydrogen-1 nuclear magnetic resonance spectroscopy |
| LCMS | liquid chromatography-mass spectrometry |

1M or 1N = 1 mol/L, 2M or 2N = 2 mol/L etc.

General Synthetic Schemes

A series of heterocyclic amide derivatives of formula (I) can be prepared as the methods described in Scheme 1. Formula (I) can be prepared by reactions of carboxylic acids 1-1 with a substituted 5-amino-1,3,4-thiadiazol-2(3H)-one derivatives 1-2 under standard amide coupling conditions (e.g., in the presence of an activating reagent such as BOP, PyBOP, HATU, HBTU, EDCI, or T$_3$P and a base, such as Hunig's base, Et$_3$N, pyridine or DMAP). Alternatively, treatment of the carboxylic acids 1-1 with the chlorine reagent such as oxalyl dichloride, thionyl chloride, POCl$_3$ or TCFH can provide the corresponding acid chlorides 1-3 which is subsequently coupled with the appropriate amine 1-2 under a base, such as Hunig's base, Et$_3$N, pyridine or DMAP to afford the corresponding compounds of formula (I).

Scheme 1

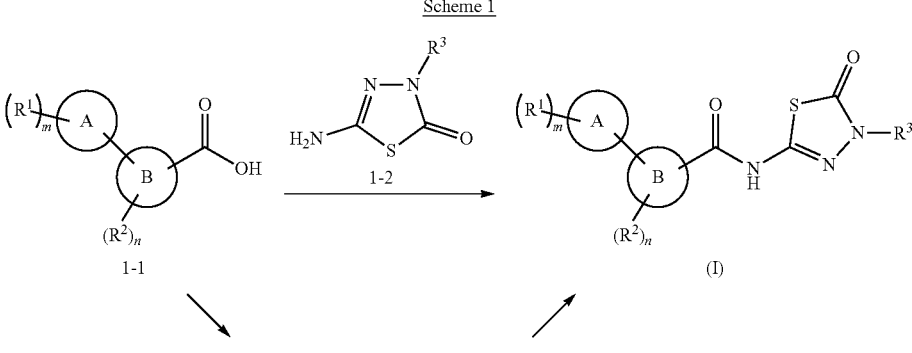

1-1

1-2

(I)

1-3

30

A series of carboxylic acid derivatives of formula 2-4 can be prepared as the methods outlined in Scheme 2. Suzuki coupling of suitable carboxylic ester derivatives 2-1 where 1) W is halogen (e.g., Cl, Br, or I) or pseudohalogen (e.g., OTf or OMs) or 2) W is boronic acid or boronic ester, with suitable formula 2-2 where 1) M is boronic acid or boronic ester or 2) M is halogen (e.g., Cl, Br, or I) or pseudohalogen (e.g., OTf or OMs) under standard Suzuki coupling conditions (e.g., in the presence of a palladium catalyst, such as $Pd(OAc)_2$, $Pd(dppf)Cl_2$, $Pd_2(dba)_3$, $Pd(PPh_3)_4$ and a base, such as t-BuOK, t-BuONa, $Cs_2CO_3$, $K_2CO_3$, or $Na_2CO_3$) can afford the carboxylic esters 2-3.

Alternatively, Stille coupling of carboxylic ester derivatives 2-1 where W is halogen (e.g., Cl, Br, or I) or pseudohalogen (e.g., OTf, OMs or $OPO(OR)_2$, each R is independently methyl, ethyl, propyl, $CH_2CF_3$) with compounds 2-2 where M is ZnBr, $SnMe_3$, or $SnBu_3$ under standard Stille coupling conditions (e.g., in the presence of a palladium catalyst, such as $Pd_2(dba)_3$, $Pd(PPh_3)_4$ or $Pd(PPh_3)_2Cl_2$ and an additive such as CuCl or LiCl) can also afford the carboxylic esters 2-3.

Saponification of the carboxylic esters 2-3 can yield the corresponding carboxylic acid derivatives 2-4 in the presence of a base such as LiOH, NaOH, KOH or $Me_3SnOH$.

Scheme 2

W

COOMe 2-1

2-2

-continued 2-3

2-4

Similarly, a series of heterocyclic acid intermediates of formula 3-5 can be prepared as the methods outlined in Scheme 3. C—C coupling of suitable compounds 3-1 with appropriate compounds 3-3 can provide ester compounds 3-4 by Suzuki coupling or Stille coupling as described in Scheme 2. Saponification of the compounds 3-4 can yield the corresponding acid 3-5 in the presence of a base such as LiOH, NaOH, KOH or $Me_3SnOH$.

Alternatively, coupling of suitable carboxylic acids 3-2 and appropriate compounds 3-3 can directly provide the corresponding acid 3-5 under standard Suzuki coupling conditions or Stille coupling conditions as described in Scheme 2.

Scheme 3

3-1

3-3

3-4

Scheme 4

4-1

4-2

4-3

4-5

4-4

4-2

Formula (IIa)

-continued 3-5

3-3

3-2

A series of heterocyclic amide derivatives of formula (IIa) can be prepared as the methods outlined in Scheme 4. Amide derivatives 4-3 can be prepared by reactions of carboxylic acids 4-1 with suitable 5-amino-1,3,4-thiadiazol-2(3H)-one derivatives 4-2 in a similar manner as those described in the Scheme 1. Coupling of the amide derivatives 4-3 where W is halogen (e.g., Cl, Br, or I) or pseudohalogen (e.g., OTf or OMs) with compounds 4-5 where M is boronic acid, boronic acid ester, trimethylstannyl or tributylstannyl under standard Suzuki coupling conditions or Stille coupling conditions (e.g., in the presence of a palladium catalyst, such as $Pd(OAc)_2$, $Pd(dppf)Cl_2$, $Pd_2(dba)_3$, $Pd(PPh_3)_4$ and a base, such as t-BuOK, t-BuONa, $Cs_2CO_3$, $K_2CO_3$, or $Na_2CO_3$) can provide compounds (IIa).

Alternatively, coupling of the amide derivatives 4-3 where W is boronic acid, boronic acid ester, trimethylstannyl or tributylstannyl with compounds 4-5 where M is halogen (e.g., Cl, Br, or I) or pseudohalogen (e.g., OTf or OMs) under standard Suzuki coupling conditions or Stille coupling conditions (e.g., in the presence of a palladium catalyst, such as $Pd(OAc)_2$, $Pd(dppf)Cl_2$, $Pd_2(dba)_3$, $Pd(PPh_3)_4$ and a base, such as t-BuOK, t-BuONa, $Cs_2CO_3$, $K_2CO_3$, or $Na_2CO_3$) can also provide compounds of formula (IIa).

A series of substituted 5-amino-1,3,4-thiadiazol-2(3H)-one derivatives of formula 5-4 can be prepared as the methods outlined in Scheme 5. Alkylation of hydrazinecarbothioamide 5-1 with $R^3$—$W^1$ 5-2 where $W^1$ is halogen (e.g., Cl, Br, or I) or pseudohalogen (e.g., OTf or OMs) in presence of a base such as $K_2CO_3$, $Cs_2CO_3$, TEA or Hunig's base can afford the hydrazinecarbothioamide derivatives 5-3. Alternatively hydrazinecarbothioamide derivatives 5-3 can be obtained by reductive amination of with $R^3$—$W^1$ 5-2 where $W^1$ is —CHO under standard reductive amination's conditions (e.g., in the presence of a reductive reagent, such as $NaBH(OAc)_3$ or $NaBH_3CN$). Treatment of hydrazinecarbothioamide derivatives 5-3 in the presence of a condensation reagent such as CDI, 4-nitrophenylchloroformate or triphosgene and a base (e.g., $K_2CO_3$ or TEA) can afford the desired 5-amino-1,3,4-thiadiazol-2(3H)-one derivatives 5-4.

Scheme 5

A series of substituted 5-amino-1,3,4-thiadiazol-2(3H)-one derivatives of formula 6-8 can be prepared as the methods outlined in Scheme 6. Substitution reaction of 5-bromo-1,3,4-thiadiazol-2-amine 6-2 with alcohols $R^A OH$ 6-1 can provide 1,3,4-thiadiazol-2-amine derivatives 6-5 in the presence of a base such as t-BuOK, t-BuONa, $Cs_2CO_3$, $K_2CO_3$, $Na_2CO_3$, NaH, NaHMDS, or LDA in a suitable solvent such as THF, DMF or DMSO.

Alternatively, 1,3,4-thiadiazol-2-amine derivatives 6-5 can be prepared from dithiocarbonate 6-3 which can be obtained by reaction of alcohols 6-1 with $CS_2$ and iodomethane in the presence of a base such as NaH, t-BuOK, t-BuONa or NaHMDS in THF. Hydrazinolysis of dithiocarbonate 6-3 with hydrazinium hydroxide solution can afford compounds 6-4 which can be transformed into 1,3,4-thiadiazol-2-amine derivatives 6-5 by treatment of BrCN in the presence of a base such as Hunig's base or TEA. Dealkylation of 1,3,4-thiadiazol-2-amine derivatives 6-5 to yield 5-amino-1,3,4-thiadiazol-2(3H)-one 6-6 can be achieved in the presence of an acid such as HBr, HCl, $H_2SO_4$, $BCl_3$ or $BBr_3$. N-alkylation of 5-amino-1,3,4-thiadiazol-2(3H)-one 6-6 with $R^3$—$W^2$ where $W^2$ is halogen (e.g., Cl, Br, or I) or pseudohalogen (e.g., OTf or OMs) in presence of a base such as NaH, NaHMDS, t-BuOK, or t-BuONa can afford the 5-amino-1,3,4-thiadiazol-2(3H)-one derivatives of formula 6-8.

Scheme 6

Alternatively, 5-amino-1,3,4-thiadiazol-2(3H)-one of formula 7-3 can be prepared as the methods outlined in Scheme 7. Treatment of hydrazinecarbothioamide 7-1 with a reagent such as CDI, 4-nitrophenylchloroformate or triphosgene in the presence of a base (e.g., $K_2CO_3$ or TEA) can provide 5-amino-1,3,4-thiadiazol-2(3H)-one 7-3. Alternatively, diazotization hydrolysis of 1,3,4-thiadiazole-2,5-diamine 7-2 with nitrite (e.g., $NaNO_2$ or isoamyl nitrite etc.) in aq. $H_2SO_4$ solution in the presence of a catalyst such as $CuSO_4$, CuO or $Cu(NO_3)_2$ can also afford the desired product 5-amino-1,3,4-thiadiazol-2(3H)-one formula 7-3.

Scheme 7

73

Int-1: 4-(3-Chloro-2-fluoro-6-methoxyphenyl)-6-methylnicotinic acid

Step 1: (3-chloro-2-fluoro-6-methoxyphenyl)boronic acid

To a solution of 1-chloro-2-fluoro-4-methoxybenzene (2.0 g, 12.5 mmol) in dry THF (20 mL) was added LDA (2.0 M in THF, 12.5 mL) at –70° C. under $N_2$ atmosphere. The mixture was stirred at –70° C. for 1 h., and then triisopropyl borate (4.70 g, 25.0 mmol) was added at –70° C. The resulting mixture was stirred at –70° C. for 2 h. The reaction mixture was quenched with sat. $NH_4Cl$ aq. solution (50 mL) at 0° C. The aqueous layer was adjusted to pH~2-3 with HCl aq. (1.0 M) and extracted with EtOAc (40 mL×5). The combined organic layers were washed with brine, dried over $Na_2SO_4$, filtered and concentrated under reduced pressure. The residue was purified by flash chromatography on a silica gel column eluting with EtOAc/PE (0-10%) to afford (3-chloro-2-fluoro-6-methoxyphenyl)boronic acid (1.6 g) as an off-white solid.

Step 2: methyl 4-(3-chloro-2-fluoro-6-methoxyphenyl)-6-methylnicotinate

A mixture of 4-chloro-6-methylnicotinate (3.0 g, 16 mmol), (3-chloro-2-fluoro-6-methoxyphenyl)boronic acid (3.2 g, 16 mmol), $K_2CO_3$ (4.4 g, 32 mmol) and Pd(dppf)Cl$_2$ (1.1 g, 1.6 mmol) in 1,4-dioxane (24 mL) and $H_2O$ (3 mL) was degassed and recharged with nitrogen for 3 cycles, and stirred at 80° C. for 16 h. The mixture was diluted with EtOAc, washed with water and brine, dried over anhydrous $Na_2SO_4$, filtered and concentrated under reduced pressure. The residue was purified by flash chromatography on a silica gel column eluting with EtOAc/PE (0-20%) to give the title compound (2.8 g) as a yellow solid. LCMS calc. for $C_{15}H_{14}FClNO_3$ $[M+H]^+$: m/z=310.1; Found: 310.0.

Step 3: 4-(3-chloro-2-fluoro-6-methoxyphenyl)-6-methylnicotinic acid

To a solution of methyl 4-(3-chloro-2-fluoro-6-methoxyphenyl)-6-methylnicotinate (70 mg, 0.23 mmol) in MeOH (2 mL) and $H_2O$ (2 mL) was added LiOH·$H_2O$ (28 mg, 1.0 mmol). After it was stirred at r.t. overnight, the reaction mixture was diluted with water and adjusted to pH~3-4 with HCl aq. (2 M), extracted with DCM (20 mL×5). The combined organic layers were washed with brine, dried over $Na_2SO_4$, filtered and concentrated under reduced pressure to afford the crude product (50 mg) as yellow oil which was used in the next step without further purification. LCMS calc. for $C_{14}H_{12}FClNO_3$ $[M+H]^+$: m/z=296.0; Found: 296.0.

Int-2: 4-(2-Fluoro-6-methoxy-3-(trifluoromethyl)phenyl)-6-methylnicotinic acid

Step 1: 2-(3-fluoro-4-(trifluoromethyl)phenyl)-4,4,5,5-tetramethyl-1,3,2-dioxaborolane

A mixture of 4-bromo-2-fluoro-1-(trifluoromethyl)benzene (9.7 g, 40 mmol), bis(pinacolato)diboron (12.7 g, 50 mmol), KOAc (9.8 g, 100 mmol) and Pd(dppf)Cl$_2$ (0.87 g, 1.2 mmol) in 1,4-dioxane (120 mL) was degassed and recharged with nitrogen for 3 cycles. The reaction mixture was stirred at 100° C. for 16 h., and concentrated under reduced pressure. The residue was diluted with EtOAc (150 mL), washed with water and brine. The organic layer was dried over anhydrous Na$_2$SO$_4$, filtered and concentrated under reduced pressure. The residue was dissolved in PE (100 mL), filtered under a pad of a silica gel and concentrated under reduced pressure to afford the title compound (11.5 g, 99% yield) as a yellow oil. TLC R$_f$=0.4 (EtOAc/PE=1/50, UV 254 nm).

Step 2: 3-fluoro-4-(trifluoromethyl)phenol

To a cooled (ice-water bath) mixture of 2-(3-fluoro-4-(trifluoromethyl)phenyl)-4,4,5,5-tetramethyl-1,3,2-dioxaborolane (11.5 g, 40 mmol), NaOH (6.4 g, 160 mmol) in THF (400 mL) and water (20 mL) was added H$_2$O$_2$ (16 mL, 33%). The reaction mixture was stirred at 0° C. for 4 h., and concentrated under reduced pressure. The residue was diluted with PE (300 mL) and filtered. The filtrate was washed with water (100 mL) and brine (100 mL). The organic layer was dried over anhydrous Na$_2$SO$_4$, filtered and concentrated to dryness under reduced pressure to afforded the title compound (7.0 g, 97% yield) as a yellow oil. LCMS calc. for C$_7$H$_3$F$_4$O [M–H]$^-$: m/z=179.0; Found: 179.0. TLC R$_f$=0.45 (EtOAc/PE=1/25, UV 254 nm)

Step 3: 2-fluoro-4-methoxy-1-(trifluoromethyl)benzene

To a mixture of 3-fluoro-4-(trifluoromethyl)phenol (7.0 g, 38.9 mmol), K$_2$CO$_3$ (13.8 g, 100 mmol) in MeCN (40 mL) was added MeI (8.5 g, 60 mmol). The reaction mixture was stirred at 40° C. for 4 h., and concentrated under reduced pressure. The residue was diluted with PE (200 mL) and filtered. The filtrate was washed with water and brine. The organic layer was dried over anhydrous Na$_2$SO$_4$, filtered and concentrated under reduced pressure. The residue was purified by flash chromatography on a silica gel column eluting with EtOAc/PE (0-5%) to afforded the title compound (4.2 g, 56% yield) as a colorless oil. TLC R$_f$=0.55 (EtOAc/PE=1/25, UV 254 nm)

Step 4: (2-fluoro-6-methoxy-3-(trifluoromethyl)phenyl)boronic acid

To a solution of 2-fluoro-4-methoxy-1-(trifluoromethyl)benzene (3.9 g, 20 mmol) in THF (40 mL) was added n-BuLi (10 mL, 2.5 M in hexane) at –60° C. After being stirred for 1 h., 2-isopropoxy-4,4,5,5-tetramethyl-1,3,2-dioxaborolane (4.6 g, 25 mmol) was added at –60° C. The reaction mixture was stirred at r.t. for 1 h. The reaction mixture was quenched with HCl aq. (2.0 M, 20 mL) at 0° C., stirred for 30 min., and extracted with EtOAc (40 mL×5). The combined organic layers were washed with brine, dried over Na$_2$SO$_4$, filtered and concentrated under reduced pressure to afford the title compound (2.0 g, 42%) as a yellow oil without further purification.

Step 5: methyl 4-(2-fluoro-6-methoxy-3-(trifluoromethyl)phenyl)-6-methylnicotinate This compound was prepared as a yellow solid by procedures analogous to those described for Int-1 Step 2 using (2-fluoro-6-methoxy-3-(trifluoromethyl)phenyl)boronic acid to replace (3-chloro-2-fluoro-6-methoxyphenyl)boronic acid. LCMS calc. for C$_{16}$H$_{14}$F$_4$NO$_3$ [M+H]$^+$: m/z=344.1; Found: 344.1.

Step 6: 4-(2-fluoro-6-methoxy-3-(trifluoromethyl)phenyl)-6-methylnicotinic acid This compound was prepared as an white solid by procedures analogous to those described for Int-1 Step 3 using methyl 4-(2-fluoro-6-methoxy-3-(trifluoromethyl)phenyl)-6-methylnicotinate. LCMS calc. for C$_{15}$H$_{12}$F$_4$NO$_3$ [M+H]$^+$: m/z=330.1; Found: 330.1.

Example 1: 4-(3-Chloro-2-fluoro-6-methoxyphe-
nyl)-N-(4-(2-methoxyethyl)-5-oxo-4,5-dihydro-1,3,
4-thiadiazol-2-yl)-6-methylnicotinamide Step 1: 5-amino-3-(2-methoxyethyl)-1,3,4-thiadi-
azol-2(3H)-one To a solution of 5-amino-1,3,4-thiadiazol-2(3H)-one (100
mg, 0.85 mmol) in DMF (1 mL) was added NaH (40 mg, 1.0
mmol, 60% dispersion in mineral oil) at 0° C. The reaction
mixture was stirred at 25° C. for 1 h. To the above mixture
was added 1-iodo-2-methoxyethane (167 mg, 0.9 mmol),
and then stirred at 90° C. overnight. The reaction mixture
was quenched with water at 0° C., and then concentrated
under reduced pressure. The residue was purified by flash
chromatography on a C18 column eluting with MeCN/water
(0-5%) to afford the title compound (37 mg) as an off-white
solid. LCMS calc. for $C_5H_{10}N_3O_2S$ $[M+H]^+$: m/z=176.0;
Found: 176.0.

Step 2: 4-(3-chloro-2-fluoro-6-methoxyphenyl)-N-
(4-(2-methoxyethyl)-5-oxo-4,5-dihydro-1,3,4-thiadi-
azol-2-yl)-6-methylnicotinamide To a mixture of 5-amino-3-(2-methoxyethyl)-1,3,4-thia-
diazol-2(3H)-one (37 mg, 0.21 mmol) and 4-(3-chloro-2-
fluoro-6-methoxyphenyl)-6-methylnicotinic acid (62 mg,
0.21 mmol, Int-1) in DMF (0.5 mL) was added NMI (87 mg,
1.1 mmol) and TCFH (77 mg, 0.28 mmol). The reaction
mixture was stirred at 50° C. overnight. The mixture was
concentrated under reduced pressure, and purified by prep-
HPLC on a C18 column eluting with MeCN/water (20-59%)
to afford the title compound (17.7 mg) as an off-white solid.
LCMS calc. for $C_{19}H_{19}ClFN_4O_4S$ $[M+H]^+$: m/z=453.1;
Found: 453.1.

Example 2: 4-(3-Chloro-2-fluoro-6-methoxyphe-
nyl)-6-methyl-N-(5-oxo-4-(2,2,2-trifluoroethyl)-4,5-
dihydro-1,3,4-thiadiazol-2-yl)nicotinamide This compound was prepared by procedures analogous to
those described for Example 1 Step 1-2 using 2,2,2-trifluo-
roethyl trifluoromethanesulfonate to replace 1-iodo-2-
methoxyethane in Step 1. LCMS calc. for
$C_{18}H_{14}ClF_4N_4O_3S$ $[M+H]^+$: m/z=477.0; Found: 477.0.

Example 3: 4-(3-Chloro-2-fluoro-6-methoxyphe-
nyl)-N-(4-ethyl-5-oxo-4,5-dihydro-1,3,4-thiadiazol-
2-yl)-6-methylnicotinamide This compound was prepared by procedures analogous to
those described for Example 1 Step 1-2 using iodoethane to
replace 1-iodo-2-methoxyethane in Step 1. LCMS calc. for
$C_{18}H_{17}ClFN_4O_3S$ $[M+H]^+$: m/z=423.1; Found: 423.1.

Example 4: 4-(3-Chloro-2-fluoro-6-methoxyphe-
nyl)-N-(4-(3-methoxypropyl)-5-oxo-4,5-dihydro-1,3,
4-thiadiazol-2-yl)-6-methylnicotinamide This compound was prepared by procedures analogous to
those described for Example 1 Step 1-2 using 1-iodo-3-
methoxypropane to replace 1-iodo-2-methoxyethane in Step
1. LCMS calc. for $C_{20}H_{21}ClFN_4O_4S$ $[M+H]^+$: m/z=467.1;
Found: 467.1.

Example 5: 4-(3-Chloro-2-fluoro-6-methoxyphenyl)-N-(4-(4-methoxybutyl)-5-oxo-4,5-dihydro-1,3,4-thiadiazol-2-yl)-6-methylnicotinamide This compound was prepared by procedures analogous to those described for Example 1 Step 1-2 using 1-bromo-4-methoxybutane to replace 1-iodo-2-methoxyethane in Step 1. LCMS calc. for $C_{21}H_{23}ClFN_4O_4S$ [M+H]$^+$: m/z=481.1; Found: 481.1.

Example 6: 4-(3-Chloro-2-fluoro-6-methoxyphenyl)-N-(4-(2-hydroxyethyl)-5-oxo-4,5-dihydro-1,3,4-thiadiazol-2-yl)-6-methylnicotinamide

Step 1: 5-amino-3-(2-((tert-butyldimethylsilyl)oxy)ethyl)-1,3,4-thiadiazol-2(3H)-one To a solution of 5-amino-1,3,4-thiadiazol-2(3H)-one (120 mg, 1.0 mmol) in DMF (1 mL) was added NaH (60 mg, 1.5 mmol, 60% dispersion in mineral oil) at 0° C. The reaction mixture was stirred at 25° C. for 1 h., and tert-butyl(2-iodoethoxy)dimethylsilane (290 mg, 1.0 mmol) was added. The mixture was stirred at 90° C. overnight. The reaction mixture was quenched with water at 0° C., and concentrated under reduced pressure. The residue was purified by flash chromatography on a C18 column eluting with MeCN/water (30-55%) to afford the title compound (65 mg) as off-white solid. LCMS calc. for $C_{10}H_{22}N_3O_2SSi$ [M+H]$^+$: m/z=276.1; Found: 276.0.

Step 2: N-(4-(2-((tert-butyldimethylsilyl)oxy)ethyl)-5-oxo-4,5-dihydro-1,3,4-thiadiazol-2-yl)-4-(3-chloro-2-fluoro-6-methoxyphenyl)-6-methylnicotinamide To a mixture of 5-amino-3-(2-((tert-butyldimethylsilyl)oxy)ethyl)-1,3,4-thiadiazol-2(3H)-one (55 mg, 0.2 mmol) and 4-(3-chloro-2-fluoro-6-methoxyphenyl)-6-methylnicotinic acid (61 mg, 0.20 mmol, Int-1) in MeCN (0.5 mL) was added NMI (87 mg, 1.1 mmol) and TCFH (75 mg, 0.26 mmol). The reaction mixture was stirred at 40° C. overnight. The reaction mixture was concentrated under reduced pressure. The residue was purified by prep-HPLC on a C18 column eluting with MeCN/water (40-59%) to afford the title compound (24.2 mg) as an off-white solid. LCMS calc. for $C_{24}H_{31}ClFN_4O_4SSi$ [M+H]$^+$: m/z=553.1; Found: 553.1.

Step 3: 4-(3-chloro-2-fluoro-6-methoxyphenyl)-N-(4-(2-hydroxyethyl)-5-oxo-4,5-dihydro-1,3,4-thiadiazol-2-yl)-6-methylnicotinamide To a solution of N-(4-(2-((tert-butyldimethylsilyl)oxy)ethyl)-5-oxo-4,5-dihydro-1,3,4-thiadiazol-2-yl)-4-(3-chloro-2-fluoro-6-methoxyphenyl)-6-methylnicotinamide (24.2 mg, 0.044 mmol) in THF (0.5 mL) was added TBAF (0.1 mL, 0.1 mmol, 1.0 M in THF). The reaction mixture was stirred at r.t. overnight, and concentrated under reduced pressure. The residue was purified by prep-HPLC on a C18 column eluting with MeCN/water (10-40%) to afford the title compound (4.0 mg) as a white solid. LCMS calc. for $C_{18}H_{17}ClFN_4O_4S$ [M+H]$^+$: m/z=439.1; Found: 439.1.

Example 7: 4-(3-Chloro-2-fluoro-6-methoxyphenyl)-N-(4-(3-hydroxypropyl)-5-oxo-4,5-dihydro-1,3,4-thiadiazol-2-yl)-6-methylnicotinamide

81

Step 1: 5-amino-3-(3-((tert-butyldimethylsilyl)oxy)propyl)-1,3,4-thiadiazol-2(3H)-one To a solution of 5-amino-1,3,4-thiadiazol-2(3H)-one (120 mg, 1.0 mmol) in DMF (1 mL) was added NaH (60 mg, 1.5 mmol, 60% dispersion in mineral oil) at 0° C. The reaction mixture was stirred at 25° C. for 1 h., and then (3-bromopropoxy)(tert-butyl)dimethylsilane (252 mg, 1.0 mmol) was added. The mixture was stirred at 90° C. overnight. The reaction mixture was quenched with water at 0° C., and concentrated under reduced pressure. The residue was purified by flash chromatography on a C18 column eluting with MeCN/water (30-55%) to afford the title compound (100 mg) as an off-white solid. LCMS calc. for $C_{11}H_{24}N_3O_2SSi$ [M+H]$^+$: m/z=290.1; Found: 290.1.

Step 2: N-(4-(3-((tert-butyldimethylsilyl)oxy)propyl)-5-oxo-4,5-dihydro-1,3,4-thiadiazol-2-yl)-4-(3-chloro-2-fluoro-6-methoxyphenyl)-6-methylnicotinamide To a mixture of 5-amino-3-(3-((tert-butyldimethylsilyl)oxy)propyl)-1,3,4-thiadiazol-2(3H)-one (58 mg, 0.2 mmol) and 4-(3-chloro-2-fluoro-6-methoxyphenyl)-6-methylnicotinic acid (61 mg, 0.2 mmol, Int-1) in MeCN (0.5 mL) was added NMI (87 mg, 1.1 mmol) and TCFH (75 mg, 0.26 mmol). The reaction mixture was stirred at 40° C. overnight. The reaction mixture was concentrated under reduced pressure. The residue was purified by prep-HPLC on a C18 column eluting with MeCN/water (40-59%) to afford the title compound (56 mg) as an off-white solid. LCMS calc. for $C_{25}H_{33}ClFN_4O_4SSi$ [M+H]$^+$: m/z=567.2; Found: 567.2.

Step 3: 4-(3-chloro-2-fluoro-6-methoxyphenyl)-N-(4-(3-hydroxypropyl)-5-oxo-4,5-dihydro-1,3,4-thiadiazol-2-yl)-6-methylnicotinamide To a solution of N-(4-(3-((tert-butyldimethylsilyl)oxy)propyl)-5-oxo-4,5-dihydro-1,3,4-thiadiazol-2-yl)-4-(3-chloro-2-fluoro-6-methoxyphenyl)-6-methylnicotinamide (56 mg, 0.1 mmol) in THF (0.5 mL) was added TBAF (0.3 mL, 0.3 mmol, 1.0 M in THF). The reaction mixture was stirred at r.t. overnight and concentrated under reduced pressure. The residue was purified by prep-HPLC on a C18 column eluting with MeCN/water (10-40%) to afford the title compound (9.4 mg) as a white solid. $^1$H NMR (600

82

MHz, DMSO-d$_6$) δ 12.57 (s, 1H), 8.81 (s, 1H), 7.60 (t, J=9.0 Hz, 1H), 7.38 (s, 1H), 6.96 (d, J=9.0 Hz, 1H), 4.56 (s, 1H), 3.90-3.78 (m, 2H), 3.64 (s, 3H), 3.48-3.40 (m, 2H), 2.51 (s, 3H), 1.84-1.75 (m, 2H). LCMS calc. for $C_{19}H_{19}ClFN_4O_4S$ [M+H]$^+$: m/z=453.1; Found: 453.1.

Example 8: 2-(5-(4-(3-Chloro-2-fluoro-6-methoxyphenyl)-6-methylnicotinamido)-2-oxo-1,3,4-thiadiazol-3(2H)-yl)acetic acid

Step 1: methyl 2-(5-amino-2-oxo-1,3,4-thiadiazol-3(2H)-yl)acetate

To a solution of 5-amino-1,3,4-thiadiazol-2(3H)-one (700 mg, 6.0 mmol) in DMF (10 mL) was added NaH (264 mg, 6.6 mmol, 60% dispersion in mineral oil) at 0° C. The reaction mixture was stirred at 25° C. for 1 h., and then methyl 2-bromoacetate (1.1 mg, 7.2 mmol) was added. The mixture was stirred at 90° C. overnight. The reaction mixture was quenched with water at 0° C., and then concentrated under reduced pressure. The residue was purified by flash chromatography on a C18 column eluting with MeCN/water (10-30%) to afford the title compound (540 mg) as an off-white solid. LCMS calc. for $C_5H_8N_3O_3S$ [M+H]$^+$: m/z=190.0; Found: 190.0.

Step 2: methyl 2-(5-(4-(3-chloro-2-fluoro-6-methoxyphenyl)-6-methylnicotinamido)-2-oxo-1,3,4-thiadiazol-3(2H)-yl)acetate A mixture of methyl 2-(5-amino-2-oxo-1,3,4-thiadiazol-3(2H)-yl)acetate (540 mg, 2.84 mmol), 4-(3-chloro-2-fluoro-6-methoxyphenyl)-6-methylnicotinic acid (888 mg, 3.0 mmol, Int-1), NMI (1.0 g 12 mmol) and TCFH (841 mg, 3.0 mmol) in DMF (8 mL) was stirred at 40° C. overnight. The reaction mixture was concentrated under reduced pressure. The residue was purified by prep-HPLC on a C18 column eluting with MeCN/water (20-45%) to afford the title compound (370 mg) as an off-white solid. LCMS calc. for $C_{19}H_{17}ClFN_4O_5S$ [M+H]$^+$: m/z=467.1; Found: 467.1.

Step 3: 2-(5-(4-(3-chloro-2-fluoro-6-methoxyphenyl)-6-methylnicotinamido)-2-oxo-1,3,4-thiadiazol-3(2H)-yl)acetic acid To a solution of methyl 2-(5-(4-(3-chloro-2-fluoro-6-methoxyphenyl)-6-methylnicotinamido)-2-oxo-1,3,4-thiadiazol-3(2H)-yl)acetate (47 mg, 0.1 mmol) in THF (0.5 mL) and $H_2O$ (0.5 mL) was added LiOH—$H_2O$ (17 mg, 0.4 mmol). The reaction mixture was stirred at r.t. overnight, and concentrated under reduced pressure. The residue was purified by prep-HPLC on a C18 column eluting with MeCN/water (10-25% with 0.1% TFA) to afford the title compound (20.8 mg) as a white solid. LCMS calc. for $C_{18}H_{15}ClFN_4O_5S$ [M+H]$^+$: m/z=453.0; Found: 453.0.

Example 9: 4-(3-Chloro-2-fluoro-6-methoxyphenyl)-N-(4-(2-((R)-3-(dimethylamino)pyrrolidin-1-yl)-2-oxoethyl)-5-oxo-4,5-dihydro-1,3,4-thiadiazol-2-yl)-6-methylnicotinamide To a mixture of (R)—N,N-dimethylpyrrolidin-3-amine (23 mg, 0.2 mmol), 2-(5-(4-(3-chloro-2-fluoro-6-methoxyphenyl)-6-methylnicotinamido)-2-oxo-1,3,4-thiadiazol-3(2H)-yl)acetic acid (46 mg, 0.1 mmol, Example 8) and DIEA (40 mg, 0.3 mmol) in DMF (5 mL) was added HATU (76 mg, 0.2 mmol). The mixture was stirred at 50° C. overnight. The reaction mixture was quenched with water at 0° C., and concentrated under reduced pressure. The residue was purified by flash chromatography on a C18 column eluting with MeCN/water (10-30% with 0.05% TFA) to afford the title compound (11.6 mg) as a white solid. LCMS calc. for $C_{24}H_{27}ClFN_6O_4S$ [M+H]$^+$: m/z=549.1; Found: 549.1.

Example 10: 4-(3-Chloro-2-fluoro-6-methoxyphenyl)-N-(4-(2-((S)-3-(dimethylamino)pyrrolidin-1-yl)-2-oxoethyl)-5-oxo-4,5-dihydro-1,3,4-thiadiazol-2-yl)-6-methylnicotinamide This compound was prepared by procedures analogous to those described for Example 9 using (S)—N,N-dimethylpyrrolidin-3-amine to replace (R)—N,N-dimethylpyrrolidin-3-amine. LCMS calc. for $C_{24}H_{27}ClFN_6O_4S$ [M+H]$^+$: m/z=549.1; Found: 549.1.

Example 11: 4-(3-Chloro-2-fluoro-6-methoxyphenyl)-N-(4-(2-cyanoethyl)-5-oxo-4,5-dihydro-1,3,4-thiadiazol-2-yl)-6-methylnicotinamide

Step 1: 3-(5-amino-2-oxo-1,3,4-thiadiazol-3(2H)-yl)propanenitrile

To a solution of 5-amino-1,3,4-thiadiazol-2(3H)-one (100 mg, 0.85 mmol) in DMF (1 mL) was added NaH (40 mg, 1.0 mmol, 60% dispersion in mineral oil) at 0° C. The reaction mixture was stirred at 25° C. for 1 h. To the above mixture was added 3-bromopropanenitrile (120 mg, 0.9 mmol), and then stirred at r.t. for 36 h. The reaction mixture was quenched with water at 0° C., and then concentrated under reduced pressure. The residue was purified by flash chromatography on a C18 column eluting with MeCN/water (20-35%) to afford the title compound (78 mg) as an off-white solid. LCMS calc. for $C_5H_7N_4OS$ [M+H]$^+$: m/z=171.0; Found: 171.0.

Step 2: 4-(3-chloro-2-fluoro-6-methoxyphenyl)-N-(4-(2-cyanoethyl)-5-oxo-4,5-dihydro-1,3,4-thiadi-azol-2-yl)-6-methylnicotinamide To a mixture of 3-(5-amino-2-oxo-1,3,4-thiadiazol-3 (2H)-yl)propanenitrile (68 mg, 0.4 mmol) and 4-(3-chloro-2-fluoro-6-methoxyphenyl)-6-methylnicotinic acid (120 mg, 0.4 mmol, Int-1) in DMF (1 mL) was added NMI (124 mg, 1.6 mmol) and TCFH (170 mg, 0.6 mmol). The reaction mixture was stirred at 40° C. overnight. The mixture was concentrated under reduced pressure, and purified by prep-HPLC on a C18 column eluting with MeCN/water (30-55%) to afford the title compound (53 mg) as a white solid. LCMS calc. for $C_{19}H_{16}ClFN_5O_3S$ [M+H]$^+$: m/z=448.1; Found: 448.1.

Example 12: 4-(3-Chloro-2-fluoro-6-methoxyphenyl)-N-(4-(3-cyanopropyl)-5-oxo-4,5-dihydro-1,3,4-thiadiazol-2-yl)-6-methylnicotinamide This compound was prepared by procedures analogous to those described for Example 11 Step 1-2 using 4-bromobutanenitrile to replace 3-bromopropionitrile in Step 1. LCMS calc. for $C_{20}H_{18}ClFN_5O_3S$ [M+H]$^+$: m/z=462.1; Found: 462.1.

Example 13: 4-(2-Fluoro-6-methoxy-3-(trifluoromethyl)phenyl)-N-(4-(3-hydroxypropyl)-5-oxo-4,5-dihydro-1,3,4-thiadiazol-2-yl)-6-methylnicotinamide This compound was prepared by procedures analogous to those described for Example 7 Step 2-3 using 5-amino-3-(3-((tert-butyldimethylsilyl)oxy)propyl)-1,3,4-thiadiazol-2 (3H)-one (Example 7 Step 1) and Int-2 as the starting material. LCMS calc. for $C_{20}H_{19}F_4N_4O_4S$ [M+H]$^+$: m/z=487.1; Found: 487.1.

Example 14: 4-(3-Chloro-2-fluoro-6-methoxyphenyl)-N-(4-(4-hydroxybutyl)-5-oxo-4,5-dihydro-1,3,4-thiadiazol-2-yl)-6-methylnicotinamide

Step 1: 5-amino-3-(4-((tert-butyldimethylsilyl)oxy)butyl)-1,3,4-thiadiazol-2(3H)-one To a solution of 5-amino-1,3,4-thiadiazol-2(3H)-one (120 mg, 1.0 mmol) in DMF (1 mL) was added NaH (60 mg, 1.5 mmol, 60% dispersion in mineral oil) at 0° C. The reaction mixture was stirred at 25° C. for 1 h., and then (4-bromobutoxy)(tert-butyl)dimethylsilane (270 mg, 1.0 mmol) was added. The mixture was stirred at 90° C. overnight, quenched with water at 0° C., and diluted with EtOAc (30 mL). The organic layer was washed with water and brine, dried over $Na_2SO_4$, filtered and concentrated under reduced pressure. The residue was purified by flash chromatography on a silica gel column eluting with EA/PE (50-80%) to afford the title compound (160 mg) as a yellow oil. LCMS calc. for $C_{12}H_{26}N_3O_2SSi$ [M+H]$^+$: m/z=304.1; Found: 304.0.

Step 2: N-(4-(4-((tert-butyldimethylsilyl)oxy)butyl)-5-oxo-4,5-dihydro-1,3,4-thiadiazol-2-yl)-4-(3-chloro-2-fluoro-6-methoxyphenyl)-6-methylnicotinamide To a mixture of 5-amino-3-(4-((tert-butyldimethylsilyl)oxy)butyl)-1,3,4-thiadiazol-2(3H)-one (91 mg, 0.3 mmol) and 4-(3-chloro-2-fluoro-6-methoxyphenyl)-6-methylnicotinic acid (60 mg, 0.2 mmol, Int-1) in DMF (1 mL) was added NMI (62 mg, 0.8 mmol) and TCFH (70 mg, 0.25 mmol). The reaction mixture was stirred at r.t. overnight, and concentrated under reduced pressure. The residue was purified by prep-HPLC on a C18 column eluting with MeCN/water (40-60%) to afford the title compound (102 mg) as a white solid. LCMS calc. for $C_{26}H_{35}ClFN_4O_4SSi$ [M+H]$^+$: m/z=581.2; Found: 581.2.

Step 3: 4-(3-chloro-2-fluoro-6-methoxyphenyl)-N-(4-(4-hydroxybutyl)-5-oxo-4,5-dihydro-1,3,4-thiadiazol-2-yl)-6-methylnicotinamide To a solution of N-(4-(3-((tert-butyldimethylsilyl)oxy)propyl)-5-oxo-4,5-dihydro-1,3,4-thiadiazol-2-yl)-4-(3-chloro-2-fluoro-6-methoxyphenyl)-6-methylnicotinamide (102 mg, 0.17 mmol) in THF (0.5 mL) was added TBAF (0.5 mL, 0.5 mmol, 1.0 M in THF). The reaction mixture was stirred at r.t. overnight, and concentrated under reduced pressure. The residue was purified by prep-HPLC on a C18 column eluting with MeCN/water (10-40%) to afford the title compound (34 mg) as a white solid. $^1$H NMR (600 MHz, DMSO-d$_6$) δ 9.09 (s, 1H), 7.46 (t, J=9.0 Hz, 1H), 7.00 (s, 1H), 6.90 (d, J=9.0 Hz, 1H), 4.91 (t, J=5.4 Hz, 1H), 3.70-3.60 (m, 5H), 3.40 (t, J=5.4 Hz, 2H), 2.51 (s, 3H), 1.66-1.60 (m, 2H), 1.40-1.30 (m, 2H). LCMS calc. for $C_{20}H_{21}ClFN_4O_4S$ [M+H]$^+$: m/z=467.1; Found: 467.1.

Example 15: 4-(3-Chloro-2-fluoro-6-methoxyphenyl)-N-(4-(3-hydroxy-3-methylbutyl)-5-oxo-4,5-dihydro-1,3,4-thiadiazol-2-yl)-6-methylnicotinamide

Step 1: 5-amino-3-(3-hydroxy-3-methylbutyl)-1,3,4-thiadiazol-2(3H)-one

To a solution of 5-amino-1,3,4-thiadiazol-2(3H)-one (120 mg, 1.0 mmol) in DMF (1 mL) was added NaH (80 mg, 2.0 mmol, 60% dispersion in mineral oil) at 0° C. The reaction mixture was stirred at 25° C. for 1 h., and then 4-bromo-2-methylbutan-2-ol (203 mg, 1.0 mmol) was added. The mixture was stirred at 40° C. overnight. The reaction mixture was quenched with water at 0° C., and then concentrated under reduced pressure. The residue was purified by flash chromatography on a C18 column eluting with MeCN/water (20-35%) to afford the title compound (100 mg) as an off-white solid. LCMS calc. for $C_7H_{14}N_3O_2S$ [M+H]$^+$: m/z=204.1; Found: 204.0.

Step 2: 4-(3-chloro-2-fluoro-6-methoxyphenyl)-N-(4-(3-hydroxy-3-methylbutyl)-5-oxo-4,5-dihydro-1,3,4-thiadiazol-2-yl)-6-methylnicotinamide This compound was prepared by procedures analogous to those described for Example 14 Step 2 using 5-amino-3-(3-hydroxy-3-methylbutyl)-1,3,4-thiadiazol-2(3H)-one and 4-(3-chloro-2-fluoro-6-methoxyphenyl)-6-methylnicotinic acid (Int-1) as the starting material. LCMS calc. for $C_{21}H_{23}ClFN_4O_4S$ [M+H]$^+$: m/z=481.1; Found: 481.1.

Example 16: 4-(3-Chloro-2-fluoro-6-methoxyphenyl)-N-(4-(3-hydroxybutyl)-5-oxo-4,5-dihydro-1,3,4-thiadiazol-2-yl)-6-methylnicotinamide

Step 1: 5-amino-3-(2-(2-methyl-1,3-dioxolan-2-yl)ethyl)-1,3,4-thiadiazol-2(3H)-one To a solution of 5-amino-1,3,4-thiadiazol-2(3H)-one (120 mg, 1.0 mmol) in DMF (1 mL) was added NaH (60 mg, 1.5 mmol, 60% dispersion in mineral oil) at 0° C. The reaction mixture was stirred at 25° C. for 1 h., and then 2-(2-bromoethyl)-2-methyl-1,3-dioxolane (194 mg, 1.0 mmol) was added. The mixture was stirred at 40° C. overnight, quenched with water at 0° C., and then concentrated under reduced pressure. The residue was purified by flash chromatography on a C18 column eluting with MeCN/water (40-45%) to afford the title compound (90 mg) as an off-white solid. LCMS calc. for $C_8H_{14}N_3O_3S$ [M+H]$^+$: m/z=232.1; Found: 232.1.

Step 2: 4-(3-chloro-2-fluoro-6-methoxyphenyl)-6-methyl-N-(4-(2-(2-methyl-1,3-dioxolan-2-yl)ethyl)-5-oxo-4,5-dihydro-1,3,4-thiadiazol-2-yl)nicotinamide This compound was prepared by procedures analogous to those described for Example 14 Step 2 using 5-amino-3-(2-(2-methyl-1,3-dioxolan-2-yl)ethyl)-1,3,4-thiadiazol-2(3H)-one and 4-(3-chloro-2-fluoro-6-methoxyphenyl)-6-methyl-nicotinic acid (Int-1) as the starting material. LCMS calc. for $C_{22}H_{23}ClFN_4O_5S$ [M+H]$^+$: m/z=509.1; Found: 509.0.

Step 3: 4-(3-chloro-2-fluoro-6-methoxyphenyl)-6-methyl-N-(5-oxo-4-(3-oxobutyl)-4,5-dihydro-1,3,4-thiadiazol-2-yl)nicotinamide A solution of 4-(3-chloro-2-fluoro-6-methoxyphenyl)-6-methyl-N-(4-(2-(2-methyl-1,3-dioxolan-2-yl)ethyl)-5-oxo-4,5-dihydro-1,3,4-thiadiazol-2-yl)nicotinamide (50 mg, 0.1 mmol) in THF (1 mL) and HCl aq. (1 mL, 4.0 M) was stirred at 70° C. for 2 h. The reaction mixture was concentrated under reduced pressure to afford the title compound (46 mg) as a yellow solid. LCMS calc. for $C_{20}H_{19}ClFN_4O_4S$ [M+H]$^+$: m/z=465.1; Found: 465.1.

Step 4: 4-(3-chloro-2-fluoro-6-methoxyphenyl)-6-methyl-N-(5-oxo-4-(3-oxobutyl)-4,5-dihydro-1,3,4-thiadiazol-2-yl)nicotinamide To a solution of 4-(3-chloro-2-fluoro-6-methoxyphenyl)-6-methyl-N-(5-oxo-4-(3-oxobutyl)-4,5-dihydro-1,3,4-thiadiazol-2-yl)nicotinamide (47 mg, 0.1 mmol) in MeOH (1 mL) was added NaBH$_4$ (19 mg, 0.5 mmol). The reaction mixture was stirred at r.t. for 1 h. and then concentrated under reduced pressure. The residue was purified by prep-HPLC on a C18 column eluting with MeCN/water (30-55%) to afford the title compound (34 mg) as a white solid. LCMS calc. for $C_{20}H_{21}ClFN_4O_4S$ [M+H]$^+$: m/z=467.1; Found: 467.1.

Example 17: 4-(3-Chloro-2-fluoro-6-methoxyphenyl)-N-(4-((3-hydroxycyclobutyl)methyl)-5-oxo-4,5-dihydro-1,3,4-thiadiazol-2-yl)-6-methylnicotinamide Step 1: 5-amino-3-((3-hydroxycyclobutyl)methyl)-1,3,4-thiadiazol-2(3H)-one To a solution of 5-amino-1,3,4-thiadiazol-2(3H)-one (120 mg, 1.0 mmol) in DMF (1 mL) was added NaH (80 mg, 2.0 mmol, 60% dispersion in mineral oil) at 0° C. The reaction mixture was stirred at 25° C. for 1 h., and 3-(bromomethyl)cyclobutan-1-ol (164 mg, 1.0 mmol) was added. The mixture was stirred at 40° C. overnight. The reaction mixture was quenched with water at 0° C., and then concentrated under reduced pressure. The residue was purified by flash chromatography on a C18 column eluting with MeCN/water (20-35%) to afford the title compound (70 mg) as an off-white solid. LCMS calc. for $C_7H_{12}N_3O_2S$ [M+H]$^+$: m/z=202.1; Found: 202.1.

Step 2: 3-((5-(4-(3-chloro-2-fluoro-6-methoxyphenyl)-6-methylnicotinamido)-2-oxo-1,3,4-thiadiazol-3(2H)-yl)methyl)cyclobutyl-4-(3-chloro-2-fluoro-6-methoxyphenyl)-6-methylnicotinate To a mixture of 5-amino-3-((3-hydroxycyclobutyl)methyl)-1,3,4-thiadiazol-2(3H)-one (40 mg, 0.2 mmol), 4-(3-chloro-2-fluoro-6-methoxyphenyl)-6-methylnicotinic acid (150 mg, 0.5 mmol, Int-1) and pyridine (80 mg, 2.0 mmol) in DCM (3 mL) was added POCl$_3$ (153 mg, 1.0 mmol). The reaction mixture was stirred at r.t. for 1 h. and diluted with MeOH (5 mL). The resulting mixture was concentrated under reduced pressure. The residue was purified by flash chromatography on a C18 column eluting with MeCN/H$_2$O (70-90%) to afford the title compound (52 mg) as a white solid. LCMS calc. for C$_{35}$H$_{30}$Cl$_2$F$_2$N$_5$O$_6$S [M+H]$^+$: m/z=756.1; Found: 756.3.

Step 3: 4-(3-chloro-2-fluoro-6-methoxyphenyl)-N-(4-((3-hydroxycyclobutyl)methyl-5-oxo-4,5-dihydro-1,3,4-thiadiazol-2-yl)-6-methylnicotinamide To a solution of 3-((5-(4-(3-chloro-2-fluoro-6-methoxyphenyl)-6-methylnicotinamido)-2-oxo-1,3,4-thiadiazol-3(2H)-yl)methyl)cyclobutyl-4-(3-chloro-2-fluoro-6-methoxyphenyl)-6-methylnicotinate (52 mg, 0.07 mmol) in THF (0.5 mL) and water (0.5 mL) was added LiOH—H$_2$O (10 mg, 0.25 mmol). The mixture was stirred at r.t. overnight. The reaction mixture was quenched with TFA (0.1 mL) and then concentrated under reduced pressure. The residue was purified by flash chromatography on a C18 column eluting with MeCN/H$_2$O (10-20% with 0.1% TFA) to afford the title compound (24.5 mg) as a white solid. LCMS calc. for C$_{21}$H$_{21}$ClFN$_4$O$_4$S [M+H]$^+$: m/z=479.1; Found: 479.1.

Example 18: N-(4-(2-(1H-pyrazol-1-yl)ethyl)-5-oxo-4,5-dihydro-1,3,4-thiadiazol-2-yl)-4-(3-chloro-2-fluoro-6-methoxyphenyl)-6-methylnicotinamide

Step 1: 3-(2-(1H-pyrazol-1-yl)ethyl)-5-amino-1,3,4-thiadiazol-2(3H)-one

To a solution of 5-amino-1,3,4-thiadiazol-2(3H)-one (120 mg, 1.0 mmol) in DMF (1 mL) was added NaH (60 mg, 1.5 mmol, 60% dispersion in mineral oil) at 0° C. The reaction mixture was stirred at 25° C. for 1 h., and 1-(2-chloroethyl)-1H-pyrazole (130 mg, 1.0 mmol) was added. The mixture was stirred at 40° C. overnight, quenched with water at 0° C., and then concentrated under reduced pressure. The residue was purified by flash chromatography on a C18 column eluting with MeCN/water (15-20%) to afford the title compound (90 mg) as a yellow oil. LCMS calc. for C$_7$H$_{10}$N$_5$OS [M+H]$^+$: m/z=212.1; Found: 212.0.

Step 2: N-(4-(2-(1H-pyrazol-1-yl)ethyl)-5-oxo-4,5-dihydro-1,3,4-thiadiazol-2-yl)-4-(3-chloro-2-fluoro-6-methoxyphenyl)-6-methylnicotinamide This compound was prepared by procedures analogous to those described for Example 14 Step 2 using 3-(2-(1H-pyrazol-1-yl)ethyl)-5-amino-1,3,4-thiadiazol-2(3H)-one and 4-(3-chloro-2-fluoro-6-methoxyphenyl)-6-methylnicotinic acid (Int-1) as the starting material. LCMS calc. for C$_{21}$H$_{19}$ClFN$_6$O$_3$S [M+H]$^+$: m/z=489.1; Found: 489.1.

Example 19: N-(4-(2-(1H-imidazol-1-yl)ethyl)-5-oxo-4,5-dihydro-1,3,4-thiadiazol-2-yl)-4-(3-chloro-2-fluoro-6-methoxyphenyl)-6-methylnicotinamide

Step 1: 3-(2-(1H-imidazol-1-yl)ethyl)-5-amino-1,3,4-thiadiazol-2(3H)-one

This compound was prepared by procedures analogous to those described for Example 18 Step 1 using 5-amino-1,3,4-thiadiazol-2(3H)-one and 1-(2-chloroethyl)-1H-imidazole to afford the title compound as a yellow oil. LCMS calc. for C$_7$H$_{10}$N$_5$OS [M+H]$^+$: m/z=212.1; Found: 212.0.

Step 2: N-(4-(2-(1H-imidazol-1-yl)ethyl)-5-oxo-4,5-dihydro-1,3,4-thiadiazol-2-yl)-4-(3-chloro-2-fluoro-6-methoxyphenyl)-6-methylnicotinamide This compound was prepared by procedures analogous to those described for Example 14 Step 2 using 3-(2-(1H-imidazol-1-yl)ethyl)-5-amino-1,3,4-thiadiazol-2(3H)-one and 4-(3-chloro-2-fluoro-6-methoxyphenyl)-6-methylnicotinic acid (Int-1) as the starting material. LCMS calc. for C$_{21}$H$_{19}$ClFN$_6$O$_3$S [M+H]$^+$: m/z=489.1; Found: 489.1.

Example 20: 4-(3-Chloro-2-fluoro-6-methoxyphe-nyl)-N-(4-(2-hydroxypropyl)-5-oxo-4,5-dihydro-1,3,4-thiadiazol-2-yl)-6-methylnicotinamide Step 1: 5-amino-3-(2-hydroxypropyl)-1,3,4-thiadi-azol-2(3H)-one To a solution of 5-amino-1,3,4-thiadiazol-2(3H)-one (120 mg, 1.0 mmol) in DMF (1 mL) was added NaH (80 mg, 2.0 mmol, 60% dispersion in mineral oil) at 0° C. The reaction mixture was stirred at 25° C. for 1 h., and then 1-bromopro-pan-2-ol (140 mg, 1.0 mmol) was added. The mixture was stirred at 40° C. overnight. The reaction mixture was quenched with water at 0° C. and concentrated under reduced pressure. The residue was purified by flash chro-matography on a C18 column eluting with MeCN/water (10-15%) to afford the title compound (50 mg) as an off-white solid. LCMS calc. for $C_5H_{10}N_3O_2S$ [M+H]$^+$: m/z=176.0; Found: 176.0.

Step 2: 1-(5-(4-(3-chloro-2-fluoro-6-methoxyphe-nyl)-6-methylnicotinamido)-2-oxo-1,3,4-thiadiazol-3(2H)-yl)propan-2-yl 4-(3-chloro-2-fluoro-6-methoxyphenyl)-6-methylnicotinate To a mixture of 5-amino-3-(2-hydroxypropyl)-1,3,4-thia-diazol-2(3H)-one (35 mg, 0.2 mmol), 4-(3-chloro-2-fluoro-6-methoxyphenyl)-6-methylnicotinic acid (150 mg, 0.5 mmol, Int-1) and pyridine (80 mg, 2.0 mmol) in DCM (3 mL) was added POCl$_3$ (153 mg, 1.0 mmol). The reaction mixture was stirred at r.t. for 1 h. and diluted with MeOH (5 mL). The resulting mixture was concentrated under reduced pressure. The residue was purified by flash chromatography on a C18 column eluting with MeCN/H$_2$O (70-90%) to afford the title compound (38 mg) as a white solid. LCMS calc. for $C_{33}H_{28}Cl_2F_2N_5O_6S$ [M+H]$^+$: m/z=730.1; Found: 730.2.

Step 3: 4-(3-chloro-2-fluoro-6-methoxyphenyl)-N-(4-((3-hydroxycyclobutyl)methyl)-5-oxo-4,5-di-hydro-1,3,4-thiadiazol-2-yl)-6-methylnicotinamide To a solution of 1-(5-(4-(3-chloro-2-fluoro-6-methoxy-phenyl)-6-methylnicotinamido)-2-oxo-1,3,4-thiadiazol-3(2H)-yl)propan-2-yl 4-(3-chloro-2-fluoro-6-methoxyphe-nyl)-6-methylnicotinate (36.5 mg, 0.05 mmol) in THF (0.5 mL) and water (0.5 mL) was added LiOH—H$_2$O (10 mg, 0.25 mmol). The mixture was stirred at r.t. overnight. The reaction mixture was quenched with TFA (0.1 mL) and then concentrated under reduced pressure. The residue was puri-fied by flash chromatography on a C18 column eluting with MeCN/H$_2$O (10-20% with 0.1% TFA) to afford the title compound (7.2 mg) as a white solid. LCMS calc. for $C_{19}H_{19}ClFN_4O_4S$ [M+H]$^+$: m/z=453.1; Found: 453.1.

Example 21: 4-(3-Chloro-2-fluoro-6-methoxyphe-nyl)-N-(4-(2-hydroxybutyl)-5-oxo-4,5-dihydro-1,3,4-thiadiazol-2-yl)-6-methylnicotinamide Step 1: 5-amino-3-(2-hydroxybutyl)-1,3,4-thiadi-azol-2(3H)-one This compound was prepared by procedures analogous to those described for Example 20 Step 1 using 1-bromobutan-2-ol to replace 1-bromopropan-2-ol to afford the title com-pound as a colorless oil. LCMS calc. for $C_6H_{12}N_3O_2S$ [M+H]$^+$: m/z=190.1; Found: 190.0.

Step 2: 4-(3-chloro-2-fluoro-6-methoxyphenyl)-N-(4-(2-hydroxybutyl)-5-oxo-4,5-dihydro-1,3,4-thiadi-azol-2-yl)-6-methylnicotinamide This compound was prepared by procedures analogous to those described for Example 21 step 2-3 using 5-amino-3-(2-hydroxybutyl)-1,3,4-thiadiazol-2(3H)-one and 4-(3-chloro-2-fluoro-6-methoxyphenyl)-6-methylnicotinic acid (Int-1) as the starting material. LCMS calc. for $C_{20}H_{21}ClFN_4O_4S$ [M+H]$^+$: m/z=467.1; Found: 467.1.

Example 22: 3-(3-Chloro-2-fluoro-6-methoxyphenyl)-N-(4-(4-hydroxybutyl)-5-oxo-4,5-dihydro-1,3,4-thiadiazol-2-yl)isonicotinamide

Step 1: methyl 3-(3-chloro-2-fluoro-6-methoxyphenyl)isonicotinate

A mixture of methyl 3-chloroisonicotinate (1.0 g, 6 mmol), (3-chloro-2-fluoro-6-methoxyphenyl)boronic acid (0.94 g, 5 mmol, Int-1 Step 1), $K_2CO_3$ (1.66 g, 12 mmol) and Pd(dppf)Cl$_2$ (0.34 g, 0.5 mmol) in 1,4-dioxane (24 mL) and H$_2$O (3 mL) was degassed and recharged with nitrogen for 3 cycles, and then stirred at 80° C. overnight. The mixture was diluted with EtOAc, washed with water and brine, dried over anhydrous Na$_2$SO$_4$, filtered and concentrated under reduced pressure. The residue was purified by flash chromatography on a silica gel column eluting with EtOAc/PE (60-70%) to afford the title compound (0.9 g) as a yellow solid. LCMS calc. for $C_{14}H_{12}ClFNO_3$ [M+H]$^+$: m/z=296.0; Found: 296.0.

Step 2: 3-(3-chloro-2-fluoro-6-methoxyphenyl)isonicotinic acid

To a solution of methyl 3-(3-chloro-2-fluoro-6-methoxyphenyl)isonicotinate (0.9 g, 3.0 mmol) in THF (4 mL) and H$_2$O (4 mL) was added LiOH—H$_2$O (380 mg, 9.0 mmol). After it was stirred at r.t. overnight, the reaction mixture was diluted with water and adjusted to pH~2-3 with HCl aq. (2 M), and then concentrated under reduced pressure. The residue was purified by flash chromatography on a C18 column eluting with MeCN/water (10-15%) to afford the title compound (0.78 g) as a white solid. LCMS calc. for $C_{13}H_{10}ClFNO_3$ [M+H]$^+$: m/z=282.0; Found: 282.0.

Step 3: 3-(3-chloro-2-fluoro-6-methoxyphenyl)-N-(4-(4-hydroxybutyl)-5-oxo-4,5-dihydro-1,3,4-thiadiazol-2-yl)isonicotinamide This compound was prepared by procedures analogous to those described for Example 14 Step 2-3 using 3-(3-chloro-2-fluoro-6-methoxyphenyl)isonicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{19}H_{19}ClFN_4O_4S$ [M+H]$^+$: m/z=453.1; Found: 453.1.

Example 23: N-(4-(4-Hydroxybutyl)-5-oxo-4,5-dihydro-1,3,4-thiadiazol-2-yl)-1-(2-methoxyphenyl)-1H-imidazole-5-carboxamide

Step 1: ethyl 1-(2-methoxyphenyl)-1H-imidazole-5-carboxylate

A mixture of ethyl glyoxylate (3.32 g, 50% purity in toluene), o-anisidine (2.0 g, 16.2 mmol) and Na$_2$SO$_4$ (13.8 g, 97.4 mmol) in toluene (20 mL) was degassed and purged with N$_2$ for three cycles, and then stirred at 110° C. for 1 h. The reaction mixture was filtered and concentrated under reduced pressure. A mixture of the above residue, K$_2$CO$_3$ (1.48 g, 10.7 mmol) and TosMIC (1.59 g, 8.1 mmol) in EtOH (20 mL) was degassed and purged with N$_2$ for three cycles, and then stirred at 50° C. for 12 h. The reaction mixture was diluted with H$_2$O (30 mL) and extracted with EtOAc (30 mL×3). The combined organic layers were washed with water and brine, dried over Na$_2$SO$_4$, filtered and concentrated under reduced pressure. The residue was purified by column chromatography on a silica gel column eluting with EtOAc/PE (10-50%) to afford the title compound (1.1 g) as a brown solid. LCMS calc. for $C_{13}H_{15}N_2O_3$ [M+H]$^+$: m/z=247.1; Found: 247.1.

Step 2: 1-(2-methoxyphenyl)-1H-imidazole-5-carboxylic acid

A mixture of ethyl 1-(2-methoxyphenyl)-1H-imidazole-5-carboxylate (500 mg, 2.0 mmol), and LiOH·$H_2O$ (170 mg, 4.1 mmol) in MeOH (5 mL) and $H_2O$ (4 mL) was stirred at r.t. overnight. The resulting mixture was diluted with water (20 mL), adjusted to pH~4-5 with HCl aq. (2 M) and extracted with DCM (20 mL×3). The combined organic layers were washed with water and brine, dried over $Na_2SO_4$, filtered and concentrated under reduced pressure to afford the title compound (200 mg) as a yellow solid. LCMS calc. for $C_{11}H_{11}N_2O_3$ [M+H]$^+$: m/z=219.1; Found: 219.1.

Step 3: N-(4-(4-hydroxybutyl)-5-oxo-4,5-dihydro-1, 3,4-thiadiazol-2-yl)-1-(2-methoxyphenyl)-1H-imida-zole-5-carboxamide This compound was prepared by procedures analogous to those described for Example 14 Step 2-3 using 1-(2-methoxyphenyl)-1H-imidazole-5-carboxylic acid and 5-amino-3-(4-((tert-butyldimethylsilyl)oxy)butyl)-1,3,4-thiadiazol-2(3H)-one (Example 14 Step 1) in Step 2. LCMS calc. for $C_{17}H_{20}N_5O_4S$ [M+H]$^+$: m/z=390.1; Found: 390.1.

Example 24: N-(4-(4-Hydroxybutyl)-5-oxo-4,5-dihydro-1,3,4-thiadiazol-2-yl)-4-(2-methoxyphenyl)-6-methylnicotinamide

Step 1: 4-(2-methoxyphenyl)-6-methylnicotinic acid

This compound was prepared by procedures analogous to those described for Example 22 Step 1-2 using methyl 4-chloro-6-methylnicotinate and (2-methoxyphenyl)boronic acid in Step 1 to afford the title compound (3.3 g) as a yellow solid. LCMS calc. for $C_{14}H_{14}NO_3$ [M+H]$^+$: m/z=244.1; Found: 244.0.

Step 2: N-(4-(4-hydroxybutyl)-5-oxo-4,5-dihydro-1, 3,4-thiadiazol-2-yl)-4-(2-methoxyphenyl)-6-methyl-nicotinamide This compound was prepared by procedures analogous to those described for Example 14 Step 2-3 using 4-(2-methoxyphenyl)-6-methylnicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{20}H_{23}N_4O_4S$ [M+H]$^+$: m/z=415.1; Found: 415.1.

Example 25: 4-(5-Chloro-2-methoxyphenyl)-N-(4-(4-hydroxybutyl)-5-oxo-4,5-dihydro-1,3,4-thiadi-azol-2-yl)-6-methylnicotinamide

Step 1: 4-(5-chloro-2-methoxyphenyl)-6-methylnicotinic acid

This compound was prepared using procedures analogous to those described for Example 22 Step 1-2 using (5-chloro- 2-methoxyphenyl)boronic acid to replace (3-chloro-2-fluoro-6-methoxyphenyl)boronic acid in Step 1. LCMS calc. for $C_{14}H_{13}ClNO_3$ [M+H]$^+$: m/z=278.1; Found: 278.0.

Step 2: 4-(5-chloro-2-methoxyphenyl)-N-(4-(4-hydroxybutyl)-5-oxo-4,5-dihydro-1,3,4-thiadiazol-2-yl)-6-methylnicotinamide This compound was prepared by procedures analogous to those described for Example 14 Step 2-3 using 4-(5-chloro-2-methoxyphenyl)-6-methylnicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{20}H_{22}ClN_4O_4S$ [M+H]$^+$: m/z=449.1; Found: 449.1.

Example 26: 6-Cyano-N-(4-(4-hydroxybutyl)-5-oxo-4,5-dihydro-1,3,4-thiadiazol-2-yl)-2-(2-methoxyphenyl)nicotinamide

Step 1: 2-chloro-3-(methoxycarbonyl)pyridine 1-oxide

To a mixture of methyl 2-chloronicotinate (3.0 g, 17.5 mmol) and trifluoroacetic anhydride (3.7 g, 17.5 mmol) in DCM (12 mL) was added hydrogen peroxide urea (3.3 g, 35.0 mmol) dropwise at 0° C. The mixture was stirred at r.t. overnight. The mixture was added to a cooled saturated $Na_2CO_3$ solution (30 mL) to adjust pH=8~9. The mixture was extracted with DCM (20 mL×3). The combined organic layers were dried over with $Na_2SO_4$, filtered, and concentrated under reduced pressure to afford the title compound (2.0 g) as a white solid. LCMS calc. for $C_7H_7ClNO_3$ [M+H]$^+$: m/z=188.0; Found: 187.9.

Step 2: methyl 2-chloro-6-cyanonicotinate

To a solution of 2-chloro-3-(methoxycarbonyl)pyridine 1-oxide (2.0 g, 10.7 mmol) and TMSCN (1.59 g, 16 mmol) in DCM (30 mL) was added acetyl chloride (1.67 g, 21.3 mmol). The resulting mixture was stirred at r.t. overnight, and quenched with saturated $Na_2CO_3$ solution (40 mL). The organic layer was washed with brine, dried over $Na_2SO_4$, filtered and concentrated under reduced pressure. The residue was purified by flash chromatography on a silica gel column eluting with EtOAc/PE (5-35%) to afford the title compound (1.5 g) as a white solid. LCMS calc. for $C_8H_7ClN_2O_2$[M+H]$^+$: m/z=197.0; Found: 196.9.

Step 3: methyl 6-cyano-2-(2-methoxyphenyl)nicotinate

This compound was prepared using procedures analogous to those described for Example 22 Step 1 using methyl 2-chloro-6-cyanonicotinate and (2-methoxyphenyl)boronic acid. LCMS calc. for $C_{15}H_{13}N_2O_3$ [M+H]$^+$: m/z=269.1; Found: 269.0.

Step 4: 6-cyano-2-(2-methoxyphenyl)nicotinic acid

A mixture of methyl 6-cyano-2-(2-methoxyphenyl)nicotinate (200 mg, 0.75 mmol) and LiOH·H$_2$O (47 mg, 1.12 mmol) in THF (3 mL) and H$_2$O (3 mL) was stirred at r.t. overnight. The mixture was adjusted to pH~2-3 with HCl aq. (2 M), filtered and concentrated under reduced pressure. The residue was triturated with CH$_3$CN (50 mL) and MeOH (10 mL) and filtered. The filtrate was concentrated under reduced pressure to afford the title compound (100 mg) as a yellow solid. LCMS calc. for $C_{14}H_{11}N_2O_3$ [M+H]$^+$: m/z=255.1; Found: 255.1.

Step 5: 6-cyano-N-(4-(4-hydroxybutyl)-5-oxo-4,5-dihydro-1,3,4-thiadiazol-2-yl)-2-(2-methoxyphenyl)nicotinamide This compound was prepared by procedures analogous to those described for Example 14 Step 2-3 using 6-cyano-2-(2-methoxyphenyl)nicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{20}H_{20}N_5O_4S$ [M+H]$^+$: m/z=426.1; Found: 426.1.

Example 27: 4-(2-Fluoro-6-methoxy-3-(trifluoromethyl)phenyl)-N-(4-(4-hydroxybutyl)-5-oxo-4,5-dihydro-1,3,4-thiadiazol-2-yl)-6-methylnicotinamide This compound was prepared by procedures analogous to those described for Example 14 Step 2-3 using 4-(2-fluoro-6-methoxy-3-(trifluoromethyl)phenyl)-6-methylnicotinic acid (Int-2) and 5-amino-3-(4-((tert-butyldimethylsilyl)oxy)butyl)-1,3,4-thiadiazol-2(3H)-one (Example 14 Step 1) in Step 2. LCMS calc. for $C_{21}H_{21}F_4N_4O_4S$ [M+H]$^+$: m/z=501.1; Found: 501.1.

Example 28: 4-(2-Fluoro-6-methoxy-3-methylphenyl)-N-(4-(4-hydroxybutyl)-5-oxo-4,5-dihydro-1,3,4-thiadiazol-2-yl)-6-methylnicotinamide

Step 1: 4-(2-fluoro-6-methoxy-3-methylphenyl)-6-methylnicotinic acid

This compound was prepared using procedures analogous to those described for Example 22 Step 1-2 using 2-fluoro-6-methoxy-3-methylphenylboronic acid and 4-chloro-6-methylnicotinate in Step 1. LCMS calc. for $C_{15}H_{15}FNO_3$ [M+H]$^+$: m/z=276.1; Found: 276.1.

Step 2: 4-(2-fluoro-6-methoxy-3-methylphenyl)-N-(4-(4-hydroxybutyl)-5-oxo-4,5-dihydro-1,3,4-thiadiazol-2-yl)-6-methylnicotinamide This compound was prepared by procedures analogous to those described for Example 14 Step 2-3 using 4-(2-fluoro-6-methoxy-3-methylphenyl)-6-methylnicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{21}H_{24}FClN_4O_4S$ [M+H]$^+$: m/z=447.1; Found: 447.1.

Example 29: 2'-Chloro-N-(4-(4-hydroxybutyl)-5-oxo-4,5-dihydro-1,3,4-thiadiazol-2-yl)-5'-methoxy-6-methyl-[4,4'-bipyridine]-3-carboxamide

Step 1: methyl 2'-chloro-5'-methoxy-6-methyl-[4,4'-bipyridine]-3-carboxylate This compound was prepared using procedures analogous to those described for Example 22 Step 1 using 4-chloro-6-methylnicotinate and (2-chloro-5-methoxypyridin-4-yl)boronic acid to afford the title compound as a yellow solid. LCMS calc. for $C_{14}H_{14}ClN_2O_3$ [M+H]$^+$: m/z=293.1; Found: 293.1.

Step 2: 2'-chloro-5'-methoxy-6-methyl-[4,4'-bipyridine]-3-carboxylic acid

To a solution of methyl 2'-chloro-5'-methoxy-6-methyl-[4,4'-bipyridine]-3-carboxylate (0.3 g, 1.0 mmol) in THF (2 mL) and $H_2O$ (2 mL) was added $LiOH$—$H_2O$ (0.13 g, 3.0 mmol). After it was stirred at r.t. overnight, the reaction mixture was diluted with water and adjusted to pH~2-3 with HCl aq. (2 M), and then concentrated under reduced pressure. The residue was purified by flash chromatography on a C18 column eluting with MeCN/water (10-15%) to afford the title compound as a yellow oil. LCMS calc. for $C_{13}H_{12}ClN_2O_3[M+H]^+$: m/z=279.1; Found: 279.1.

Step 3: 2'-chloro-N-(4-(4-hydroxybutyl)-5-oxo-4,5-dihydro-1,3,4-thiadiazol-2-yl)-5'-methoxy-6-methyl-[4,4'-bipyridine]-3-carboxamide This compound was prepared by procedures analogous to those described for Example 14 Step 2-3 using 2'-chloro-5'-methoxy-6-methyl-[4,4'-bipyridine]-3-carboxylic acid and 5-amino-3-(4-((tert-butyldimethylsilyl)oxy)butyl)-1,3,4-thiadiazol-2(3H)-one (Example 14 Step 1) in Step 2. LCMS calc. for $C_{19}H_{21}ClN_5O_4S$ $[M+H]^+$: m/z=450.1; Found: 450.1.

Example 30: 4-(3-Chloro-2-fluoro-6-methoxyphenyl)-N-(4-(4-hydroxybutyl)-5-oxo-4,5-dihydro-1,3,4-thiadiazol-2-yl)-6-(1-methyl-1H-pyrazol-3-yl)nicotinamide

Step 1: methyl 6-chloro-4-(3-chloro-2-fluoro-6-methoxyphenyl)nicotinate

This compound was prepared using procedures analogous to those described for Example 22 Step 1 using methyl 4,6-dichloronicotinate and (3-chloro-2-fluoro-6-methoxyphenyl)boronic acid (Int-1 Step 1) to afford the title compound as a yellow solid. LCMS calc. for $C_{14}H_{11}Cl_2FNO_3$ $[M+H]^+$: m/z=330.0; Found: 330.0.

Step 2: methyl 4-(3-chloro-2-fluoro-6-methoxyphenyl)-6-(1-methyl-1H-pyrazol-3-yl)nicotinate A mixture of methyl 6-chloro-4-(3-chloro-2-fluoro-6-methoxyphenyl)nicotinate (0.3 g, 1 mmol), 1-methyl-3-(4,4,5,5-tetramethyl-1,3,2-dioxaborolan-2-yl)-1H-pyrazole (0.42 g, 2 mmol), $K_2CO_3$ (0.41 g, 3 mmol) and $Pd(dppf)Cl_2$ (73 mg, 0.1 mmol) in 1,4-dioxane (4 mL) and $H_2O$ (0.4 mL) was degassed and recharged with nitrogen for 3 cycles, and then stirred at 80° C. overnight. The mixture was diluted with EtOAc, washed with water and brine, dried over anhydrous $Na_2SO_4$, filtered and concentrated under reduced pressure. The residue was purified by flash chromatography on a silica gel column eluting with MeOH/DCM (0-7%) to afford the title compound (120 mg) as a yellow solid. LCMS calc. for $C_{18}H_{16}ClFN_3O_3[M+H]^+$: m/z=376.1; Found: 376.1.

Step 3: 4-(3-chloro-2-fluoro-6-methoxyphenyl)-6-(1-methyl-1H-pyrazol-3-yl)nicotinic acid To a solution of methyl 4-(3-chloro-2-fluoro-6-methoxyphenyl)-6-(1-methyl-1H-pyrazol-3-yl)nicotinate (120 mg, 0.32 mmol) in THF (2 mL) and $H_2O$ (2 mL) was added $LiOH\cdot H_2O$ (42 mg, 1.0 mmol). After it was stirred at r.t. overnight, the reaction mixture was diluted with water and adjusted to pH~2-3 with HCl aq. (2 M), and then concentrated under reduced pressure. The residue was purified by flash chromatography on a C18 column eluting with MeCN/water (0-10%) to afford the title compound (100 mg) as a white solid. LCMS calc. for $C_{17}H_{14}ClFN_3O_3[M+H]^+$: m/z=362.1; Found: 362.1.

Step 4: 4-(3-chloro-2-fluoro-6-methoxyphenyl)-N-(4-(4-hydroxybutyl)-5-oxo-4,5-dihydro-1,3,4-thiadiazol-2-yl)-6-(1-methyl-1H-pyrazol-3-yl)nicotinamide This compound was prepared by procedures analogous to those described for Example 14 Step 2-3 using 4-(3-chloro- 2-fluoro-6-methoxyphenyl)-6-(1-methyl-1H-pyrazol-3-yl) nicotinic acid and 5-amino-3-(4-((tert-butyldimethylsilyl) oxy)butyl)-1,3,4-thiadiazol-2(3H)-one (Example 14 Step 1) in Step 2. LCMS calc. for $C_{23}H_{23}FClN_6O_4S$ [M+H]$^+$: m/z=533.1; Found: 533.1.

Example 31: 4-(3-Chloro-2-fluoro-6-methoxyphenyl)-6-cyano-N-(4-(4-hydroxybutyl)-5-oxo-4,5-dihydro-1,3,4-thiadiazol-2-yl)nicotinamide

Step 1: methyl 4-(3-chloro-2-fluoro-6-methoxyphenyl)-6-cyanonicotinate

A mixture of methyl 4-chloro-6-cyanonicotinate (0.4 g, 2.0 mmol), (3-chloro-2-fluoro-6-methoxyphenyl)boronic acid (0.49 g, 2.4 mmol, Int-1 Step 1), $Na_2CO_3$ (0.64 g, 6 mmol) and Pd(dppf)Cl$_2$ (146 mg, 0.25 mmol) in 1,4-dioxane (20 mL) and H$_2$O (5 mL) was degassed and recharged with N$_2$ for three cycles and stirred at 80° C. overnight. The resulting mixture was diluted with water (20 mL) and extracted with EtOAc (20 mL×3). The combined organic layers were washed with water and brine, dried over Na$_2$SO$_4$, filtered and concentrated under reduced pressure. The residue was purified by flash chromatography on a silica gel column eluting with EtOAc/PE (30-50%) to afford the title compound (0.44 g) as a light yellow solid. LCMS calc. for $C_{15}H_{10}ClFN_2O_3$[M+H]$^+$: m/z=320.0; Found: 320.0.

Step 2: 4-(3-chloro-2-fluoro-6-methoxyphenyl)-6-cyanonicotinic acid

A mixture of methyl 4-(3-chloro-2-fluoro-6-methoxyphenyl)-6-cyanonicotinate (0.42 g, 1.31 mmol) and LiOH·H$_2$O (168 mg, 4 mmol) in THF (3 mL) and H$_2$O (3 mL) was stirred at r.t. overnight. After it was stirred at r.t. overnight, the reaction mixture was diluted with water and adjusted to pH~3-4 with HCl aq. (2 M), extracted with DCM (20 mL×5). The combined organic layers were washed with brine, dried over Na$_2$SO$_4$, filtered and concentrated under reduced pressure to afford the crude product (210 mg) as a yellow oil. LCMS calc. for $C_{14}H_9ClFN_2O_3$[M+H]$^+$: m/z=307.0; Found: 307.0.

Step 3: 4-(3-chloro-2-fluoro-6-methoxyphenyl)-6-cyano-N-(4-(4-hydroxybutyl)-5-oxo-4,5-dihydro-1,3,4-thiadiazol-2-yl)nicotinamide This compound was prepared by procedures analogous to those described for Example 14 Step 2-3 using 4-(3-chloro-2-fluoro-6-methoxyphenyl)-6-cyanonicotinic acid and 5-amino-3-(4-((tert-butyldimethylsilyl)oxy)butyl)-1,3,4-thiadiazol-2(3H)-one (Example 14 Step 1) in Step 2. LCMS calc. for $C_{20}H_{18}FClN_5O_4S$ [M+H]$^+$: m/z=478.1; Found: 478.1.

Example A: Biological Evaluation

The ability of the compounds of the present disclosure to inhibit ATPase activity of PolQ (1-899) was determined using the assay described below.

PolQ ATPase activity was determined by ADP-Glo assay. 10-point dilution series of compounds were used in a 384 well format for the inhibition assays. PolQ (1-899) (1 nM) in assay buffer (20 mM Tris HCl (pH 8.0), 80 mM KCl, 10 mM MgCl$_2$, 1 mM DTT, 0.01% BSA, 0.01% Tween, 5% glycerol) was transferred to the test wells (20 uL), except the low control wells (20 μL of assay buffer was added to the low control wells). The plate was then incubated at room temperature for 30 min. An equal volume (20 μL) of 100 μM ATP, 150 nM ssDNA containing 50 thymine bases in assay buffer was added to all the test wells. The plates were covered and left to incubate for 60 min. at room temperature before the addition of the ADP Glo detection reagents. After 60 min. incubation, transfer 5 μL reaction mix to another 384-well plate and add 5 μL ADP Glo and plates incubated for 60 min. before addition of 10 μL kinase detection reagent. After the addition of the kinase detection reagent, the plates were covered and incubated for 60 min. and read luminescence on Envision Percent inhibition was calculated as follows:

$$\% \text{ Inhibition} = (\text{Signal}_{Max} - \text{Signal}_{Compound})/(\text{Signal}_{Max} - \text{Signal}_{Min}) * 100\%),$$

where "Max" is the high control (DMSO) and "Min" is the no enzyme control.

IC$_{50}$ values were calculated using a four-parameter logistic curve fit using the following formula:

$$Y = \text{LowerBound} + ((\text{UpperBound} - \text{LowerBound})/(1 + ((IC_{50}/x)^{\wedge}\text{Hill}))).$$

IC$_{50}$ values were determined by fitting the data to the standard 4 parameters with Hill Slope using GraphPad Prism software. IC$_{50}$: *≤10 nM, 10 nM<**≤100 nM, 100 nM<*≤500 nM, **>500 nM. The experimental results of the compounds are described in Table 1.

TABLE 1

| | | PolQ ATPase assay | | | |
|---|---|---|---|---|---|
| Example | IC$_{50}$ (nM) | Example | IC$_{50}$ (nM) | Example | IC$_{50}$ (nM) |
| 1 | * | 2 | * | 3 | * |
| 4 | * | 5 | * | 6 | * |
| 7 | * | 8 | * | 9 | ** |
| 10 | ** | 11 | * | 12 | * |
| 13 | * | 14 | * | 15 | * |
| 16 | * | 17 | * | 18 | * |
| 19 | * | 20 | * | 21 | * |
| 22 | * | 23 | **** | 24 | ** |
| 25 | * | 26 | *** | 27 | * |
| 28 | * | 29 | ** | 30 | * |
| 31 | * | | | | |

Although the present invention has been comprehensively described through its embodiments, it is worth noting that various changes and modifications are obvious to those skilled in the art. Such changes and modifications should be included in the scope of the appended claims of the present invention.

What is claimed:

1. A compound of Formula (I), or a pharmaceutically acceptable salt, solvate, tautomer, stereoisomer, atropisomer, isotopic variant, or deuterated compound thereof; wherein:

ring A is C$_3$-C$_{14}$ cycloalkylene, 4-14 membered heterocycloalkylene, C$_6$-C$_{14}$ arylene or 5-14 membered heteroarylene;

ring B is partially unsaturated 5-14 membered heterocycloalkylene, C$_6$-C$_{14}$ arylene or 5-14 membered heteroarylene;

m is 0, 1, 2, 3, 4 or 5;

n is 0, 1, 2, 3, 4 or 5;

each R$^1$ is independently H, D, halogen, —CN, —NO$_2$, —N$_3$, —SF$_5$, oxo, C$_1$-C$_6$ alkyl, C$_2$-C$_6$ alkenyl, C$_2$-C$_6$ alkynyl, C$_3$-C$_6$ cycloalkyl, 4-6 membered heterocycloalkyl, phenyl or 5-6 membered heteroaryl, —NR$^C$R$^D$, —OR$^A$, —SR$^A$, —NR$^C$OR$^A$, —C(O)R$^B$, —C(O)NR$^C$R$^D$, —C(O)OR$^A$, —OC(O)R$^B$, —NR$^C$C (O)R$^B$, —S(O)R$^B$, —S(O)$_2$R$^B$, —S(O)NR$^C$R$^D$, —NR$^C$S(O)$_2$R$^D$, —S(O)$_2$NR$^C$R$^D$, —NR$^C$S(O)$_2$ NR$^C$R$^D$, —NR$^C$S(O)(=NR$^B$)R$^B$, —SiR$^G$R$^H$R$^I$, —B(OR$^C$)(OR$^D$), —P(O)R$^E$R$^F$, —P(O)OR$^E$OR$^F$, —OP(O)OR$^E$OR$^F$; wherein, the C$_1$-C$_6$ alkyl, C$_2$-C$_6$ alkenyl, C$_2$-C$_6$ alkynyl, C$_3$-C$_6$ cycloalkyl, 4-6 membered heterocycloalkyl, phenyl or 5-6 membered heteroaryl is optionally substituted with 1, 2, 3, 4 or 5 substituent(s) independently selected from R$^{1A}$, or two R$^1$ together with the atom(s) to which they are attached form oxo, C$_3$-C$_7$ cycloalkyl or 4-7 membered heterocycloalkyl; wherein, the C$_3$-C$_7$ cycloalkyl or 4-7 membered heterocycloalkyl is optionally substituted with 1, 2, 3, 4 or 5 substituent(s) independently selected from R$^{1A}$;

each R$^{1A}$ is independently D, halogen, CN, —NO$_2$, N$_3$, oxo, OR$^a$, NR$^C$R$^d$, C(O)NR$^C$R$^d$, C$_1$-C$_6$ alkyl, C$_2$-C$_6$ alkenyl, C$_2$-C$_6$ alkynyl, C$_3$-C$_6$ cycloalkyl, 4-6 membered heterocycloalkyl, phenyl, or 5-6 membered heteroaryl; wherein, the C$_1$-C$_6$ alkyl, C$_2$-C$_6$ alkenyl, C$_2$-C$_6$ alkynyl, C$_3$-C$_6$ cycloalkyl, 4-6 membered heterocycloalkyl, phenyl, or 5-6 membered heteroaryl is optionally substituted with D, halogen, —CN, —OH, —NH$_2$, oxo, —NR$^C$R$^d$, —OR$^a$, —SR$^a$, C$_1$-C$_6$ alkyl, C$_1$-C$_6$ haloalkyl;

each R$^2$ is independently H, D, —CN, —NO$_2$, —N$_3$, oxo, —SF$_5$, halogen, C$_1$-C$_6$ alkyl, C$_2$-C$_6$ alkenyl, C$_2$-C$_6$ alkynyl, C$_3$-C$_{10}$ cycloalkyl, 4-10 membered heterocycloalkyl, C$_6$-C$_{10}$ aryl, 5-10 membered heteroaryl, —NR$^C$R$^D$, —OR$^A$, —SR$^A$, —NR$^C$OR$^A$, —C(O)R$^B$, —C(O)NR$^C$R$^D$, —C(O)OR$^A$, —OC(O)R$^B$, —NR$^C$C (O)R$^B$, —S(O)R$^B$, —S(O)$_2$R$^B$, —S(O)NR$^C$R$^D$, —NR$^C$S(O)$_2$R$^D$, —S(O)$_2$NR$^C$R$^D$, —NR$^C$S(O)$_2$ NR$^C$R$^D$, —NR$^C$S(O)(=NR$^B$)R$^B$, —SiR$^G$R$^H$R$^I$, —B(OR$^C$)(OR$^D$), —P(O)R$^E$R$^F$, —P(O)OR$^E$OR$^F$, —OP(O)OR$^E$OR$^F$; wherein, the C$_1$-C$_6$ alkyl, C$_2$-C$_6$ alkenyl, C$_2$-C$_6$ alkynyl, C$_3$-C$_{10}$ cycloalkyl, 4-10 membered heterocycloalkyl, C$_6$-C$_{10}$ aryl, 5-10 membered heteroaryl is optionally substituted with 1, 2, 3, 4 or 5 substituent(s) independently selected from R$^{2A}$; or two R$^2$ together with the atom(s) to which they are attached form oxo, C$_3$-C$_7$ cycloalkyl, 4-7 membered heterocycloalkyl; wherein, the C$_3$-C$_7$ cycloalkyl, 4-7 membered heterocycloalkyl is optionally substituted by 1, 2, 3 or 4 substituents independently selected from R$^{2A}$;

each R$^{2A}$ is independently D, halogen, —CN, —OH, —NH$_2$, —NO$_2$, —SF$_5$, oxo, C$_1$-C$_4$ alkyl, C$_2$-C$_4$ alkenyl, C$_2$-C$_4$ alkynyl, C$_3$-C$_6$ cycloalkyl, 4-6 membered heterocycloalkyl, phenyl, 5-6 membered heteroaryl, —NR$^C$R$^d$, —OR$^a$, —SR$^a$, —C(O)R$^b$, —C(O)NR$^C$R$^d$, —C(O)OR$^a$, —OC(O)R$^b$, —OC(O)NR$^C$R$^d$, —NR$^C$C (O)R$^b$, —NR$^C$C(O) NR$^C$R$^d$, —NR$^C$C(O) OR$^a$, —S(O) (=NR$^b$)R$^b$, —S(O)R$^b$, —S(O)NR$^C$R$^d$, —S(O)$_2$R$^b$, —NR$^C$S(O)$_2$R$^d$, —S(O)$_2$NR$^C$R$^d$, —NR$^C$S(O)$_2$NR$^C$R$^d$, or —NR$^C$S(O)(=NR$^b$)R$^b$;

wherein, the C$_1$-C$_4$ alkyl, C$_2$-C$_4$ alkenyl, C$_2$-C$_4$ alkynyl, C$_3$-C$_6$ cycloalkyl, 4-6 membered heterocycloalkyl, phenyl, or 5-6 membered heteroaryl is optionally substituted with D, halogen, —CN, —OH, —NH$_2$, oxo, —NR$^{c1}$R$^{d1}$, —OR$^{a1}$, —SR$^{a1}$, C$_1$-C$_6$ alkyl, C$_1$-C$_6$ haloalkyl;

R$^3$ is C$_1$-C$_{10}$ alkyl, C$_2$-C$_{10}$ alkenyl, C$_2$-C$_{10}$ alkynyl, C$_3$-C$_{14}$ cycloalkyl, 4-14 membered heterocycloalkyl, C$_6$-C$_{14}$ aryl, 5-14 membered heteroaryl; wherein, the C$_1$-C$_{10}$ alkyl, C$_2$-C$_{10}$ alkenyl, C$_2$-C$_{10}$ alkynyl, C$_3$-C$_{14}$ cycloalkyl, 4-14 membered heterocycloalkyl, C$_6$-C$_{14}$ aryl, 5-14 membered heteroaryl is optionally substituted by 1, 2, 3, 4 or 5 substituent(s) independently selected from R$^4$;

each R$^4$ is independently H, D, halo, —CN, —NO$_2$, —N$_3$, oxo, —NR$^C$R$^D$, —OR$^A$, —SR$^A$, —NR$^C$OR$^A$, —C(O) R$^B$, —C(O)NR$^C$R$^D$, —C(O)OR$^A$, —OC(O)R$^B$, —OC (O)NR$^C$R$^D$, —NR$^C$C(O)R$^B$, —NR$^C$C(O)NR$^C$R$^D$, —NR$^C$C(O)OR$^A$, —S(O)R$^B$, —S(O)$_2$R$^B$, —S(O) NR$^C$R$^D$, —NR$^C$S(O)$_2$R$^D$, —S(O)$_2$NR$^C$R$^D$, —NR$^C$S (O)$_2$NR$^C$R$^D$, —NR$^C$S(O)(=NR$^B$)R$^B$, —SiR$^G$R$^H$R$^I$, —B(OR$^C$)(OR$^D$), —P(O)R$^E$R$^F$, C$_1$-C$_6$ alkyl, C$_2$-C$_6$ alkenyl, C$_2$-C$_6$ alkynyl, C$_6$-C$_{10}$ aryl, C$_3$-C$_{10}$ cycloalkyl, 5-10 membered heteroaryl, or 4-10 membered heterocycloalkyl; wherein, the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, or 4-10 membered heterocycloalkyl is optionally substituted with 1, 2, 3, 4, or 5 substituents independently selected from $R^5$; or two $R^4$ together with the atom(s) to which they are attached form oxo, $C_3$-$C_6$ cycloalkyl, 4-6 membered heterocycloalkyl; each ring is optionally substituted with 1, 2, 3, 4 or 5 substituent(s) independently selected from $R^5$;

each $R^5$ is independently D, CN, halo, $NO_2$, —$N_3$, $SF_5$, oxo, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, optionally substituted 4-6 membered heterocycloalkyl, —$OR^a$, —$SR^a$, —$C(O)R^b$, —$C(O)NR^cR^d$, —$C(O)OR^a$, —$OC(O)R^b$, —$OC(O)NR^cR^d$, —$NR^cR^d$, —$NR^cC(O)R^b$, —$NR^cC(O)NR^cR^d$, —$NR^cC(O)$ $OR^a$, —$S(O)(=NR^b)R^b$, —$S(O)R^b$, —$S(O)NR^cR^d$, —$S(O)_2R^b$, —$NR^CS(O)_2R^d$, —$S(O)_2NR^cR^d$, —$NR^CS$ $(O)_2NR^cR^d$, —$NR^CS(O)(=NR^b)R^b$, —$SiR^GR^HR^I$, or —$B(OR^C)(OR^D)$; wherein, the optionally substituted substituent is selected from D, halo, CN, OH, $C_1$-$C_4$ alkyl, $C_1$-$C_4$ haloalkyl, —O—$C_1$-$C_4$ alkyl, —$OC_1$-$C_4$ haloalkyl;

each $R^4$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene, $SiR^GR^HR^I$; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocyclalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, $C_1$-$C_4$ alkyl, $C_1$-$C_4$ haloalkyl, —$C_1$-$C_4$ alkyl-OH, —$C_1$-$C_4$ alkyl-CN, —$C_1$-$C_4$ alkyl-O—$C_1$-$C_4$ alkyl, —$C_1$-$C_4$ alkyl-O—$C_1$-$C_4$ haloalkyl, —$NO_2$, oxo, —$OR^a$, —$SR^a$, —$SF_5$, —$NHOR^a$, —$C(O)R^b$, —$C(O)NR^cR^d$, —$C(O)OR^a$, —$OC(O)R^b$, —$OC(O)NR^cR^d$, —$NR^cR^d$, —$NR^cC(O)R^b$, —$NR^cC(O)NR^cR^d$, —$NR^cC(O)$ $OR^a$, —$B(OR^c)(OR^d)$, —$C(=NR^c)NR^cR^d$, —$NR^dC(=NR^c)NR^cR^d$, —$NR^dC(=NR^c)R^b$, —$P(O)R^eR^f$, —$P(O)OR^eOR^f$, —$OP(O)OR^eOR^f$, —$S(O)R^b$, —$S(O)NR^cR^d$, —$S(O)_2R^b$, —$NR^C$ $S(O)_2R^b$, —$S(O)_2NR^cR^d$, —$NR^CS(O)_2NR^cR^d$, or —$NR^CS(O)(=NR^b)R^b$;

each $R^B$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, —CN, halo, oxo, $C_1$-$C_4$ alkyl, $C_1$-$C_4$ haloalkyl, $C_1$-$C_4$ cyanoalkyl, $C_1$-$C_4$ alkyl-O—$C_1$-$C_4$ alkyl, $C_1$-$C_4$ alkyl- O—$C_1$-$C_4$haloalkyl, —$SF_5$, —$OR^a$, —$C(O)R^b$, —$OC(O)NR^cR^d$, —$NR^cR^d$, —$NR^cC(O)R^b$, —$NR^cC(O)$ $NR^cR^d$, —$NR^cC(O)$ $OR^a$, —$S(O)R^b$, —$S(O)NR^cR^d$, —$S(O)_2R^b$, —$NR^CS(O)_2R^b$, —$S(O)_2NR^cR^d$, —$NR^CS$ $(O)_2NR^cR^d$, or —$B(OR^c)(OR^d)$;

$R^C$ and $R^D$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, CN, halo, oxo, $C_1$-$C_4$ alkyl, $C_1$-$C_4$ haloalkyl, $C_1$-$C_4$ cyanoalkyl, —$C_1$-$C_4$ alkyl-O—$C_1$-$C_4$ alkyl, —$C_1$-$C_4$ alkyl-O—$C_1$-$C_4$ haloalkyl, —$SF_5$, —$OR^a$, —$OC(O)NR^cR^d$, —$NR^cR^d$, —$NR^cC(O)R^b$, —$S(O)NR^cR^d$, —$S(O)_2R^b$, —$NR^CS(O)_2R^b$, —$S(O)_2NR^cR^d$, —$NR^CS(O)_2NR^cR^d$ or —$B(OR^c)(OR^d)$;

or $R^C$ and $R^D$ together with the N atom to which they are attached form 4-7 membered heterocycloalkyl optionally substituted with 1, 2, 3, 4 or 5 substituent(s) independently selected from D, —OH, oxo, —CN, —$NH_2$, —$NH(C_1$-$C_4$ alkyl), —$N(C_1$-$C_4$ alkyl)$_2$, halo, $C_1$-$C_4$ alkyl, $C_1$-$C_4$ haloalkyl, $C_1$-$C_4$ cyanoalkyl, —$OC_1$-$C_4$ alkyl, or —$OC_1$-$C_4$ haloalkyl;

$R^a$ and $R^{a1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, halo, —OH, —CN, —$NH_2$, —$NH(C_1$-$C_4$ alkyl), —$N(C_1$-$C_4$ alkyl)$_2$, $C_1$-$C_4$ alkyl, $OC_1$-$C_4$ alkyl, $C_1$-$C_4$ haloalkyl, or —$OC_1$-$C_4$ haloalkyl;

$R^b$ and $R^{b1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_3$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene; wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, or 4-10 membered heterocycloalkyl-$C_1$-$C_6$ alkylene is optionally substituted with 1, 2, 3, 4 or 5 substituent(s) independently selected from D, OH, CN, —$NH_2$, —$NH(C_1$-$C_4$ alkyl), —$N(C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_6$-$C_{10}$ aryl, $C_3$-$C_{10}$ cycloalkyl, 5-10 membered heteroaryl, or 4-10 membered heterocycloalkyl;

$R^c$, $R^d$, $R^{e1}$, $R^{d1}$ are each independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl); wherein, the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkylene, 5-10 membered heteroaryl-$C_1$-$C_6$ alkylene, $C_3$-$C_{10}$ cycloalkyl-$C_1$-$C_6$ alkylene, 4-10 membered heterocycloalkyl-$C_1$-$C_6$ alkylene, $C_6$-$C_{10}$ aryl-$C_3$-$C_{10}$ cycloalkylene, $C_6$-$C_{10}$ aryl-4-10 membered heterocycloalkylene, $C_6$-$C_{10}$ aryl-5-10 membered heteroarylene, bi($C_6$-$C_{10}$ aryl), 5-10 membered heteroaryl-$C_3$-$C_{10}$ cycloalkylene, 5-10 membered heteroaryl-4-10 membered heterocycloalkylene, 5-10 membered heteroaryl-$C_6$-$C_{10}$ arylene, or bi(5-10 membered heteroaryl) is optionally substituted with 1, 2, 3, 4 or 5 substituent(s) independently selected from D, OH, CN, —$NH_2$, —$NH(C_1$-$C_4$ alkyl), —$N(C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkyl-O—$C_1$-$C_4$ alkyl or $C_1$-$C_4$ alkyl-O—$C_1$-$C_4$ alkyl-O—;

or $R^c$ and $R^d$ together with the N atom to which they are attached form a 4-7 membered heterocycloalkyl optionally substituted with 1, 2, 3, 4 or 5 substituent(s) independently selected from D, OH, CN, —$NH_2$, —$NH(C_1$-$C_4$ alkyl), —$N(C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl or $C_1$-$C_4$ alkoxy-$C_1$-$C_4$ alkoxy;

or $R^{e1}$ and $R^{d1}$ together with the N atom to which they are attached form a 4-7 membered heterocycloalkyl optionally substituted with 1, 2, 3, 4 or 5 substituent(s) independently selected from D, —OH, —CN, —$NH_2$, —$NH(C_1$-$C_4$ alkyl), —$N(C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C_1$-$C_4$ alkoxy-$C_1$-$C_4$ alkyl or $C_1$-$C_4$ alkoxy-$C_1$-$C_4$ alkoxy;

$R^E$ and $R^e$ are each independently H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

$R^F$ and $R^f$ are each independently H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl; and $R^G$, $R^H$ and $R^I$ are each independently optionally substituted $C_1$-$C_4$ alkyl or optionally substituted phenyl;

wherein, the optionally substituted substituent is selected from D, halo, CN, OH, $C_1$-$C_4$ alkyl, $C_1$-$C_4$ haloalkyl, —O—$C_1$-$C_4$ alkyl, —$OC_1$-$C_4$ haloalkyl.

2. The compound of Formula (I), or a pharmaceutically acceptable solvate, tautomer, stereoisomer, atropisomer, isotopic variant, or deuterated compound thereof of claim 1, wherein, the moiety has the structure of wherein, $Y^1$, $Y^2$, $Y^3$, $Y^4$, $Y^5$ are each independently selected from N or $CR^1$.

3. The compound of Formula (I), or a pharmaceutically acceptable salt, solvate, tautomer, stereoisomer, atropisomer, isotopic variant, of deuterated compound thereof of claim 2, wherein, the moiety has the structure of

4. The compound of Formula (I), or a pharmaceutically acceptable salt solvate, tautomer, stereoisomer, atropisomer, isotopic variant, or deuterated compound thereof of claim 1, wherein, each $R^1$ is independently (i) H, D, halo, or —$OR^A$; or (ii) $C_1$-$C_6$ alkyl, $C_2$-$C_6$ alkynyl; each is optionally substituted with 1, 2, 3, 4, or 5 substituents, each of which is independently $R^{1A}$.

5. The compound of Formula (I), or a pharmaceutically acceptable salt, solvate, tautomer, stereoisomer, atropisomer, isotopic variant, or deuterated compound thereof of claim 4, wherein each $R^1$ is independently H, —F, —Cl, —$CH_3$, —$CHF_2$, —$CF_3$, —$OCH_3$, —$OCHF_2$, —$OCF_3$, or —C≡CH.

6. The compound of Formula (I) or a pharmaceutically acceptable salt solvate, tautomer, stereoisomer, atropisomer, isotopic variant, or deuterated compound thereof of claim 5, wherein one of the $R^1$ groups is —$OCH_3$ or —C≡CH.

7. The compound of Formula (I), or a pharmaceutically acceptable salt, solvate, tautomer, stereoisomer, atropisomer, isotopic variant, or deuterated compound thereof of claim 5, wherein one of the $R^1$ groups is —F, —Cl, —$CH_3$, —$CHF_2$, —$CF_3$, —$OCH_3$, —$OCHF_2$, or —$OCF_3$.

8. The compound of Formula (I) or a pharmaceutically acceptable salt, solvate, tautomer, stereoisomer, atropisomer, isotopic variant, or deuterated compound thereof of claim 1, wherein, the moiety has the structure of

9. The compound of Formula (I), or pharmaceutically acceptable salt, solvate, tautomer, stereoisomer, atropisomer, isotopic variant, or deuterated compound thereof of claim 8, wherein, the moiety has the structure of -continued has the structure of

10. The compound of Formula (I), or a pharmaceutically acceptable salt, solvate, tautomer, stereoisomer, atropisomer, isotopic variant, or deuterated compound thereof of claim 1, wherein, the moiety has the structure of wherein, the position * is attached to ring A, the position ** is attached to C═O;

$X^1$, $X^2$, $X^3$, $X^4$ are each independently selected from N or $CR^2$;

$X^5$ is $NR^1$, O or S.

11. The compound of Formula (I), or a pharmaceutically acceptable salt, solvate, tautomer, stereoisomer, atropisomer, isotopic variant, or deuterated compound thereof of claim 10, wherein, the moiety

12. The compound of Formula (I), or a pharmaceutically acceptable salt, solvate, tautomer, stereoisomer, atropisomer, isotopic variant, or deuterated compound thereof of claim 11, wherein, the moiety has the structure of

13. The compound of Formula (I), or a pharmaceutically acceptable salt, solvate, tautomer, stereoisomer, atropisomer, isotopic variant, or deuterated compound thereof of claim 12, wherein, the moiety has the structure of -continued

14. The compound of Formula (I), or a pharmaceutically acceptable salt, solvate, tautomer, stereoisomer, atropisomer, isotopic variant, or deuterated compound thereof of claim 13, wherein, the moiety has the structure of

15. The compound of Formula (I), or a pharmaceutically acceptable salt, solvate, tautomer, stereoisomer, atropisomer, isotopic variant, or deuterated compound thereof of claim 1, wherein, each $R^2$ is independently (i) H, D, —CN, or halo; or (ii) $C_1$-$C_6$ alkyl or 5-10 membered heteroaryl, each optionally substituted with 1, 2, 3, 4, or 5 substituents, each of which is independently $R^{2A}$.

16. The compound of (I), or a pharmaceutically acceptable salt, solvate, tautomer, stereoisomer, atropisomer, isotopic variant, or deuterated compound thereof of claim 15, wherein, each $R^2$ is independently H, D, —CN, methyl, or 1-methylpyrazolyl.

17. The compound of Formula (I), or a pharmaceutically acceptable salt, solvate, tautomer, stereoisomer, atropisomer, isotopic variant, or deuterated compound thereof of claim 1, wherein, the moiety has the structure of

18. The compound of Formula (I), or a pharmaceutically acceptable salt, solvate, tautomer, stereoisomer, atropisomer, isotopic variant, or deuterated compound thereof of claim 1, wherein, $R^3$ is $C_1$-$C_8$alkyl optionally substituted by 1, 2, 3, 4 or 5 substituent(s) independently selected from $R^4$.

19. The compound of Formula (I), or a pharmaceutically acceptable salt, solvate, tautomer, stereoisomer, atropisomer, isotopic variant, or deuterated compound thereof of claim 18, wherein, $R^3$ is $C_1$-$C_6$ alkyl optionally substituted by 1, 2, 3, 4 or 5 substituent(s) independently selected from $R^4$.

20. The compound of Formula (I), or a pharmaceutically acceptable salt, solvate, tautomer, stereoisomer, atropisomer, isotopic variant, or deuterated compound thereof of claim 19, wherein, $R^3$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2F$, —$CH_2CHF_2$, —$CH_2CF_3$, —$CF_2CH_3$, —$CH_2CH_2OH$, —$CH_2CH_2CH_2OH$, —$CH_2CH(OH)$ $CH_3$, —$CH_2CH(OH)$ $CH_2CH_3$, —$CH_2CH_2CH(CH_3)$ OH, —$CH_2CH_2$ $C(CH_3)_2OH$, —$CH_2CH_2CH_2CH_2OH$, —$CH_2CH_2OCH_3$, —$CH_2CH_2CH_2OCH_3$, —$CH_2COOH$, —$CH_2CN$, —$CH_2CH_2CN$, —$CH_2CH_2CH_2CN$, -continued

21. The compound of Formula (I), or a pharmaceutically acceptable salt, solvate, tautomer, stereoisomer, atropisomer, isotopic variant, or deuterated compound thereof of claim 1, wherein, each $R^4$ is independently H, D, halo, —CN, —$N_3$, oxo, —$NR^CR^D$, —$OR^A$, —$SR^A$, —$C(O)R^B$, —$C(O)NR^CR^D$, —$C(O)OR^A$, —$OC(O)R^B$, —$NR^CC(O)R^B$, —$S(O)R^B$, —$S(O)_2R^B$, —$S(O)NR^CR^D$, —$NR^CS(O)_2R^D$, —$S(O)_2NR^CR^D$, $C_6$-$C_{10}$ aryl, $C_3$-$C_{10}$ cycloalkyl, 5-10 membered heteroaryl, or 4-10 membered heterocycloalkyl; wherein, the $C_6$-$C_{10}$ aryl, $C_3$-$C_{10}$ cycloalkyl, 5-10 membered heteroaryl, or 4-10 membered heterocycloalkyl is optionally substituted with 1, 2, 3, 4, or 5 substituents independently selected from $R^5$.

22. The compound of Formula (I), or pharmaceutically acceptable salt, solvate, tautomer, stereoisomer, atropisomer, isotopic variant, or deuterated compound thereof of claim 21, wherein, each $R^4$ is independently H, D, halo, —CN, —$NO_2$, —$N_3$, oxo, —$NH_2$, —$NHCH_3$, —$N(CH_3)_2$, —$NHCH_2CH_3$, —$N(CH_2CH_3)_2$, —OH, —$OCH_3$, —$OCH_2CH_3$, —$OCH_2CH_2CH_3$, —$OCH(CH_3)_2$, —$OCH_2F$, —$OCHF_2$, —$OCF_3$, —$OCH_2CH_2F$, —$OCH_2CHF_2$, —$OCH_2CF_3$, —$OCF_2CF_3$, —$OCH_2CH_2OH$, —$OCH_2CH_2OCH_3$, —$C(O)NH_2$, —$C(O)NHCH_3$, —$C(O)$ $N(CH_3)_2$,

—$C(O)CH_3$, —$C(O)CH_2CH_3$, —$C(O)CH_2CH_2CH_3$, —$C(O)CH(CH_3)_2$, —OTMS,

-continued (IIa)

(IIb)

(IIc)

or a pharmaceutically acceptable salt, solvate, tautomer, stereoisomer, atropisomer, isotopic variant or deuterated compound thereof;

$X^1$, $X^2$, $X^3$, $X^4$ are each independently selected from N or $CR^2$; wherein, $R^1$, $R^2$, $R^3$ and m are defined with respect to Formula (I).

24. The compound of claim 23, wherein, the compound of Formula (I) is represented by compounds of Formula (IIIa), (IIIb), (IIIc), (IIId), (IIIe), (IIIf) or (IIIg):

(IIIa)

(IIIb)

(IIIc)

cyclopropyl, cyclobutyl, cyclopentyl, cyclohexyl, pyrrolyl, imidazolyl, oxazolyl, isoxazolyl, thiazolyl, pyrazolyl, 1,2,4-triazolyl, 1,2,3-triazolyl, thiadiazolyl, oxadiazolyl, pyridinyl, pyrimidinyl, pyrazinyl, pyridazinyl, indolyl, azetidinyl, oxetanyl, pyrrolidinyl, tetrahydrofuranyl, tetrahydrothiophenyl, piperidinyl, dioxanyl, tetrahydropyranyl, tetrahydrothiopyranyl, piperazinyl, morpholinyl, azepanyl, diazocanyl, 1,4-diazepanyl; each is optionally substituted with 1, 2, 3, 4, or 5 substituents independently selected from $R^5$; or two $R^4$ together with the atom(s) to which they are attached form oxo; or two $R^4$ together with the atom(s) to which they are attached form

23. The compound of claim 1, wherein, the compound of Formula (I) is represented by compounds of Formula (IIa), (IIb) or (IIc):

-continued

-continued (IIId)

(IVb)

(IIIe)

(IVc)

(IIIf)

(IVd)

(IIIg)

(IVe)

or a pharmaceutically acceptable salt, solvate, tautomer, stereoisomer, atropisomer, isotopic variant, or deuterated compound thereof;

wherein, $R^1$, $R^2$, $R^3$ and m are defined with respect to Formula (I).

25. The compound of Formula (I), or a pharmaceutically acceptable salt, solvate, tautomer, stereoisomer, atropisomer, isotopic variant, or deuterated compound thereof of claim 24, wherein, the compound of Formula (I) is represented by compounds of Formula (IVa), (IVb), (IVc), (IVd), (IVe), (IVf) or (IVg):

(IVa)

(IVf)

125

-continued (IVg)

Y³ is N or CR¹;

wherein, R¹, R², R³ and m are defined with respect to Formula (I).

26. The compound of claim 1, wherein, the compound is:

126

-continued

127

-continued

128

-continued

129

130 or a pharmaceutically acceptable salt, solvate, tautomer, stereoisomer, atropisomer, isotopic variant, or deuterated compound thereof.

27. A pharmaceutical composition comprising the compound of claim 1, or pharmaceutically acceptable salt, solvate, tautomer, stereoisomer, atropisomer, isotopic variant, or deuterated compound thereof and at least one pharmaceutically acceptable excipient.

28. A method for treating a cancer in a patient comprising administering to the patient a therapeutically effective amount of the compound of Formula (I), or a pharmaceutically acceptable salt, solvate, tautomer, stereoisomer, atropisomer, isotopic variant, or deuterated compound thereof of claim 1, wherein the cancer is characterized by overexpression of PolQ, the cancer is characterized by increased dependence upon MMEJ DSB repair, the cancer is characterized by HR-deficiency, a reduction or absence of expression of HR-associated genes, the cancer is lack of 53BP1/Shieldin complex, the cancer is following or not following exposure to PARPi medication, which are resistant to PARPi treatment, the cancer is characterized by NHEJ deficiency, a reduction or absence of expression of NHEJ-associated genes.

29. A method for treating a cancer in a patient comprising administering to the patient a therapeutically effective amount of the pharmaceutical composition of claim 27, wherein the cancer is characterized by overexpression of PolQ, the cancer is characterized by increased dependence upon MMEJ DSB repair, the cancer is characterized by HR-deficiency, a reduction or absence of expression of HR-associated genes, the cancer is lack of 53BP1/Shieldin complex, the cancer is following or not following exposure to PARPi medication, which are resistant to PARPi treatment, the cancer is characterized by NHEJ deficiency, a reduction or absence of expression of NHEJ-associated genes.

30. A method for treating a cancer in a patient comprising administering to the patient a therapeutically effective amount of the compound of Formula (I), or a pharmaceutically acceptable salt, solvate, tautomer, stereoisomer, atropisomer, isotopic variant, or deuterated compound thereof of claim 1, wherein the cancer is ovarian, breast, cervical, uterine, pancreatic, lung, colorectal, gastric, bladder, or prostate cancer.

\* \* \* \* \*